United States Patent
Inghardt et al.

(10) Patent No.: US 6,599,894 B1
(45) Date of Patent: Jul. 29, 2003

(54) AMIDINOBENZYLAMINE DERIVATIVES AND THEIR USE AS THROMBIN INHIBITORS

(75) Inventors: Tord Inghardt, Frillesås (SE); Jan-Erik Nyström, Rönninge (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/508,742

(22) PCT Filed: Jan. 13, 2000

(86) PCT No.: PCT/SE00/00052

§ 371 (c)(1),
(2), (4) Date: Mar. 16, 2000

(87) PCT Pub. No.: WO00/42059

PCT Pub. Date: Jul. 20, 2000

(30) Foreign Application Priority Data

Jan. 13, 1999 (SE) .............................................. 9900071
Nov. 22, 1999 (SE) .............................................. 9904228

(51) Int. Cl.[7] .................... A61K 31/395; C07D 205/04; A61P 43/00
(52) U.S. Cl. ............................ 514/210.02; 514/210.17; 514/210.18; 514/422; 548/523; 548/952; 548/953
(58) Field of Search .................. 548/523, 953, 548/952; 514/422, 210.17, 210.02, 210.18

(56) References Cited

U.S. PATENT DOCUMENTS

| | | | |
|---|---|---|---|
| 4,346,078 A | 8/1982 | Bajusz et al. | 424/177 |
| 5,705,487 A | 1/1998 | Schacht et al. | 514/19 |
| 5,707,966 A | 1/1998 | Schacht et al. | 514/19 |
| 5,710,130 A | 1/1998 | Schacht et al. | 514/19 |
| 5,744,487 A | 4/1998 | Ohshima et al. | 514/326 |
| 6,265,397 B1 | 7/2001 | Karlsson et al. | |

FOREIGN PATENT DOCUMENTS

| | | |
|---|---|---|
| EP | 0 185 390 | 6/1986 |
| EP | 0 195 212 A2 | 9/1986 |
| EP | 0 293 881 | 12/1988 |
| EP | 0 362 002 A1 | 4/1990 |
| EP | 0 364 344 | 4/1990 |
| EP | 0 468 231 A3 | 1/1992 |
| EP | 0 468 231 A2 | 1/1992 |
| EP | 0 526 877 A3 | 2/1993 |
| EP | 0 526 877 A2 | 2/1993 |
| EP | 0 530 167 A1 | 3/1993 |
| EP | 0 542 525 A2 | 5/1993 |
| EP | 0 559 046 | 9/1993 |
| EP | 0 641 779 A1 | 3/1995 |
| EP | 0 648 780 A1 | 4/1995 |
| EP | 0 669 317 A1 | 8/1995 |
| WO | 97/46577 | 12/1977 |
| WO | 93/11152 | 6/1993 |
| WO | 93/18060 | 9/1993 |
| WO | 94/29336 | 12/1994 |
| WO | 95/23609 | 8/1995 |
| WO | 95/35309 | 12/1995 |
| WO | 96/03374 | 2/1996 |
| WO | 96/25426 | 8/1996 |
| WO | 96/31504 | 10/1996 |
| WO | 96/32110 | 10/1996 |
| WO | 97/02284 | 1/1997 |
| WO | 97/23499 | 7/1997 |
| WO | WO 97/33576 | 9/1997 |
| WO | 97/49404 | 12/1997 |
| WO | 98/06740 | 2/1998 |

OTHER PUBLICATIONS

Blood Coagul. Fibrin. 5, 411 (1994).
J. Clin. Lab. Invest. 24, suppl. 107, 59 (1969).

*Primary Examiner*—Joseph K. McKane
*Assistant Examiner*—Andrea D. Small
(74) *Attorney, Agent, or Firm*—Nixon & Vanderhye

(57) ABSTRACT

There is provided compounds of formula I

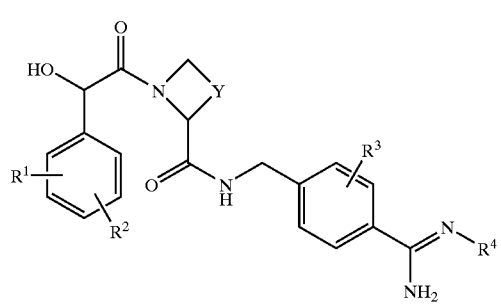

wherein $R^1$, $R^2$, Y, $R^3$ and $R^4$ have meanings given in the description which are useful as, or as prodrugs of, competitive inhibitors of trypsin-like proteases, such as thrombin, and in particular in the treatment of conditions where inhibition of thrombin is required (e.g. thrombosis) or as anticoagulants.

23 Claims, No Drawings

AMIDINOBENZYLAMINE DERIVATIVES AND THEIR USE AS THROMBIN INHIBITORS

This application is a 371 of PCT/SE00/00052 filed Jan. 13, 2000.

FIELD OF THE INVENTION

This invention relates to novel pharmaceutically useful compounds, in particular compounds that are, or are prodrugs of, competitive inhibitors of trypsin-like serine proteases, especially thrombin, their use as medicaments, pharmaceutical compositions containing them and synthetic routes to their production.

BACKGROUND

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions. One of the ultimate steps in this series of reactions is the conversion of the proenzyme prothrombin to the active enzyme thrombin.

Thrombin is known to play a central role in coagulation. It activates platelets, leading to platelet aggregation, converts fibrinogen into fibrin monomers, which polymerise spontaneously into fibrin polymers, and activates factor XIII, which in turn crosslinks the polymers to form insoluble fibrin. Furthermore, thrombin activates factor V and factor VIII leading to a "positive feedback" generation of thrombin from prothrombin.

By inhibiting the aggregation of platelets and the formation and crosslinking of fibrin, effective inhibitors of thrombin would be expected to exhibit antithrombotic activity. In addition, antithrombotic activity would be expected to be enhanced by effective inhibition of the positive feedback mechanism.

Further, it is known that administration of prodrugs of thrombin inhibitors may give rise to improvements m:

(a) certain pharmacokinetic properties after administration of; and (b) the prevalence of certain side effects associated with, those inhibitors.

PRIOR ART

The early development of low molecular weight inhibitors of thrombin has been described by Claesson in Blood Coagul. Fibrinol. (1994) 5, 411.

Blombäck et al (in J. Clin. Lab. Invest. 24, suppl. 107, 59, (1969)) reported thrombin inhibitors based on the amino acid sequence situated around the cleavage site for the fibrinogen Aa chain. Of the amino acid sequences discussed, these authors suggested the tripeptide sequence Phe-Val-Arg (P9-P2-P1, hereinafter referred to as the P3-P2-P1 sequence) would be the most effective inhibitor.

Thrombin inhibitors based on dipeptidyl derivatives with an α,ω-aminoalkyl guanidine in the P1-position are known from U.S. Pat. No. 4,346,078 and International Patent Application WO 93/11152. Similar, structurally related, dipeptidyl derivatives have also been reported. For example International Patent Application WO 94/29336 discloses compounds with, for example, aminomethyl benzamidines, cyclic aminoalkyl amidines and cyclic aminoalkyl guanidines in the P1-position (International Patent Application WO 97/23499 discloses prodrugs of certain of these compounds); European Patent Application 0 648 780, discloses compounds with, for example, cyclic aminoalkyl guanidines in the P1-position.

Thrombin inhibitors based on peptidyl derivatives, also having cyclic aminoalkyl guanidines (e.g. either 3- or 4-aminomethyl-1-amidino-piperidine) in the P1-position are known from European Patent Applications 0 468 231, 0 559 046 and 0 641 779.

Thrombin inhibitors based on tripeptidyl derivatives with arginine aldehyde in the P1-position were first disclosed in European Patent Application 0 185 390.

More recently, arginine aldehyde-based peptidyl derivatives, modified in the P3-position, have been reported. For example, International Patent Application WO 93/18060 discloses hydroxy acids, European Patent Application 0 526 877 des-amino acids, and European Patent Application 0 542 525 O-methyl mandelic acids in the P3-position.

Inhibitors of serine proteases (e.g. thrombin) based on electrophilic ketones in the P1-position are also known. For example, European Patent Application 0 195 212 discloses peptidyl α-keto esters and amides, European Patent Application 0 362 002 fluoroalkylamide ketones, European Patent Application 0 364 344 α,β,δ-triketocompounds, and European Patent Application 0 530 167 α-alkoxy ketone derivatives of arginine in the P1-position.

Other, structurally different, inhibitors of trypsin-like serine proteases based on C-terminal boronic acid derivatives of arginine and isothiouronium analogues thereof are known from European Patent Application 0 293 881.

More recently, thrombin inhibitors based on peptidyl derivatives have been disclosed in European Patent Application 0 669 317 and International Patent Applications WO 95/35309, WO 95/23609, WO 96/25426, WO 97/02284, WO 97/46577, WO 96/32110, WO 96/31504, WO 96/03374, WO 98/06740 and WO 97/49404.

However, there remains a need for effective inhibitors of trypsin-like serine proteases, such as thrombin. There is also a need for compounds which are both orally bioavailable and selective in inhibiting thrombin over other serine proteases, in particular those involved in haemostatis. Compounds which exhibit competitive inhibitory activity towards thrombin would be expected to be especially useful as anticoagulants and therefore in the therapeutic treatment of thrombosis and related disorders.

DISCLOSURE OF THE INVENTION

According to the invention there is provided a compound of formula I,

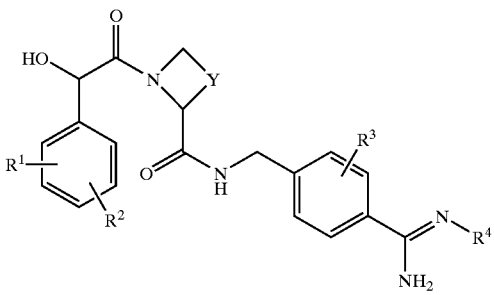

wherein
$R^1$ represents a $N(R^5)R^6$ or a $S(O)_mR^7$ substituent;
$R^2$ and $R^3$ independently represent an optional substituent selected from halo, $C_{1-4}$ alkyl or $C_{1-4}$ alkoxy (which latter two groups are optionally substituted by halo);
Y represents $C_{1-3}$ alkylene, optionally substituted by $C_{1-4}$ alkyl, methylene, =O or hydroxy);
$R^4$ represents H, OH, $OR^{8a}$, $C(O)OR^{8b}$ or $R^{8c}$;
$R^5$ represents $C_{1-6}$ alkyl (optionally substituted by halo) or, together with
$R^6$ and the nitrogen atom to which $R^5$ and $R^6$ are attached, represents a 3- to 7-membered nitrogen containing ring, which ring optionally includes an oxygen atom and/or is optionally substituted with a =O group;
$R^6$ represents $C_{1-6}$ alkyl (optionally substituted by halo), $C(O)R^9$ or, together with $R^5$ and the nitrogen atom to which $R^5$ and $R^6$ are attached, represents a 3- to 7-membered nitrogen-containing ring, which ring optionally includes an oxygen atom and/or is optionally substituted with a =O group;
or the group $N(R^5)R^6$ represents the structural fragment Ia,

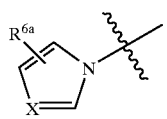

Ia $R^{6a}$ represents one or more optional substituents selected from halo, $C_{1-4}$ alkyl and $C_{1-4}$ alkoxy (which latter two groups are optionally substituted by halo);
X represents CH or N;
m represents 0, 1 or 2;
$R^7$ represents H, $NH_2$ or $C_{1-6}$ alkyl;
$R^{8a}$ and $R^{8b}$ independently represent $C_{1-10}$ alkyl, $C_{1-3}$ alkylphenyl or $C_{6-10}$ aryl, or $R^{8a}$ represents $C(R^{10a})(R^{10b})OC(O)R^{11}$, $C(R^{10a})(R^{10b})N(H)C(O)OR^{12}$ or $C(R^{10a})(R^{10b})OC(O)N(H)R^{12}$;
$R^{8c}$ represents $C(R^{10a})(R^{10b})OC(O)R^{11}$, $C(R^{10a})(R^{10b})N(H)C(O)OR^{12}$ or $C(R^{10a})(R^{10b})OC(O)N(H)R^{12}$;
$R^{10a}$ and $R^{10b}$ independently represent, at each occurrence, H or $C_{1-4}$ alkyl;
$R^{11}$ represents, at each occurrence, $C_{6-10}$ aryl, $OR^{12}$ or $C_{1-7}$ alkyl (which latter group is optionally substituted by a substituent selected from OH, $CO_2H$ and $C_{6-10}$ aryl);
$R^{12}$ represents, at each occurrence, $C_{6-10}$ aryl or $C_{1-6}$ alkyl (which latter group is optionally substituted by a substituent selected from OH, $CO_2H$ and $C_{6-10}$ aryl);
$R^9$ represents $C_{6-8}$, alkyl, $Het^1$, $C_{6-10}$ aryl or $C_{1-4}$ alkyl substituted by $C_{6-10}$ aryl; and $Het^1$ represents a 4- to 12-membered heterocyclic ring, which ring contains one or more heteroatoms selected from oxygen, nitrogen and/or sulfur, and which ring may be fully saturated, partially saturated or aromatic and/or optionally monocyclic, bicyclic and/or benzofused; wherein each aryl/phenyl group and $Het^1$ group identified above is optionally substituted by one or more halo, $C_{1-4}$ alkyl and/or $C_{1-4}$ alkoxy groups (which latter two groups are themselves optionally substituted by one or more halo groups);
or a pharmaceutically acceptable salt thereof, provided that:
(a) when m represents 1 or 2, then $R^7$ does not represent H; and
(b) when m represents 0, then $R^7$ does not represent $NH_2$;
which compounds are referred to hereinafter as "the compounds of the invention".

Pharmaceutically acceptable salts include inorganic acid (e.g. hydrogen halide), and organic acid (e.g. acetic, methanesulfonic or trifluoroacetic acid), addition salts.

The compounds of the invention may exhibit tautomerism. All tautomeric forms and mixtures thereof are included within the scope of the invention. Particular tautomeric forms that may be mentioned include those connected with the position of the double bond in the amidine functionality in the compound of formula I, and the position of the substituent $R^4$, when this does not represent H.

The compounds of formula I also contain at least two asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

As used herein, the term "aryl" includes phenyl, naphthyl and the like. Alkyl groups which $R^2$, $R^3$, $R^5$, $R^6$, $R^{6a}$, $R^7$, $R^{8a}$, $R^{8b}$, $R^9$, $R^{10a}$, $R^{10b}$, $R^{11}$, and $R^{12}$ may represent, and with which Y and aryl/phenyl and $Het^1$ groups may be substituted; alkoxy groups which $R^2$, $R^3$ and $R^{6a}$ may represent, and with which aryl/phenyl and $Het^1$ groups may be substituted; the alkyl part of alkylphenyl or alkylaryl groups which $R^{8a}$, $R^{8b}$, $R^9$, $R^{11}$ and $R^{12}$ may represent; and alkylene groups which Y may represent, may, when there is a sufficient number of carbon atoms, be linear or branched, be saturated or unsaturated, be cyclic, acyclic or part cyclic/acyclic, and/or be optionally interrupted by an O atom. The skilled person will appreciate that when alkyl groups that $R^2$, $R^3$, $R^5$, $R^6$, $R^{6a}$, $R^7$, $R^{8a}$, $R^{8b}$, $R^9$, $R^{10a}$, $R^{10b}$, $R^{11}$ and $R^{12}$ may represent, and with which Y and aryl/phenyl and $Het^1$ groups may be substituted are cyclic and interrupted by oxygen, they may then represent oxygen-containing heterocycles such as tetrahydrofuranyl or (where appropriate) tetrahydropyranyl.

Halo groups which $R^2$, $R^3$ and $R^{6a}$ may represent, and with which $R^2$, $R^3$, $R^5$, $R^6$, $R^{6a}$ and aryl/phenyl and $Het^1$ groups may be substituted, include fluoro, chloro, bromo and iodo.

Abbreviations are listed at the end of this specification.

When $R^5$ and $R^6$, together with the nitrogen atom to which they are attached, represent a 3- to 7-membered nitrogen-containing (e.g. pyrrolidine) ring, which ring optionally includes an oxygen atom and/or is substituted by a =O group, the ring is preferably substituted at a carbon atom that is α to the nitrogen atom. For the avoidance of doubt, the nitrogen atom to which $R^5$ and $R^6$ are attached is the nitrogen atom that must be present in the ring.

Compounds of the invention which may be mentioned include those in which:

$R^2$ and $R^3$ independently represent an optional substituent selected from halo or $C_{1-4}$ alkyl (optionally substituted by halo);

$R^5$ represents $C_{1-6}$ alkyl or, together with $R^6$ and the nitrogen atom to which $R^5$ and $R^6$ are attached, represents a 3- to 7-membered nitrogen containing ring, optionally substituted with a =O group;

$R^6$ represents $C_{1-6}$ alkyl, $C(O)R^9$ or, together with $R^5$ and the nitrogen atom to which $R^5$ and $R^6$ are attached, represents a 3- to 7-membered nitrogen-containing ring, optionally substituted with a =O group;

when $R^4$ represents $OR^{8a}$ or $C(O)OR^{8b}$, $R^{8a}$ and $R^{8b}$ independently represent, at each occurrence, $C_{1-10}$ alkyl, $C_{1-3}$ alkylphenyl or $C_{6-10}$ aryl, which latter two groups are optionally substituted by one or more halo, $C_{1-4}$ alkyl and/or $C_{1-4}$ alkoxy groups;

$R^9$ represents $C_{1-6}$ alkyl; and all other substituents are otherwise as defined hereinbefore.

Further compounds of the invention that may be mentioned include those in which $R^4$ does not represent $R^{8c}$.

Preferred compounds of the invention include those in which:

$R^2$, if present, represents linear or branched $C_{1-4}$ alkyl or $C_{1-4}$ alkoxy (both of which are optionally substituted by halo), or halo (e.g. chloro);

$R^3$ is either absent or, if present, represents linear or branched $C_{1-4}$ alkyl, or halo;

$R^5$ represents linear, branched or cyclic $C_{1-6}$ alkyl or, together with $R^6$ and the nitrogen atom to which $R^5$ and $R^6$ are attached, represents a 4- to 6-membered nitrogen containing ring, optionally substituted with a =O group;

$R^6$ represents linear, branched or cyclic $C_{1-6}$ alkyl, $C(O)$—$C_{1-6}$ alkyl or, together with $R^5$ and the nitrogen atom to which $R^5$ and $R^6$ are attached, represents a 4- to 6-membered nitrogen-containing ring, optionally substituted with a =O group;

$R^7$ represents linear, branched or cyclic $C_{1-6}$ alkyl;

Y represents $CH_2$ or $(CH_2)_2$.

When $R^4$ represents $OR^{8a}$, preferred compounds of the invention include those in which $R^{8a}$ represents linear or branched $C_{1-6}$ alkyl, $C_{4-5}$ cyclic alkyl (which latter two groups are optionally interrupted by oxygen), or phenyl or $C_{1-2}$ alkylphenyl (e.g. benzyl) (which latter two groups are optionally substituted as specified hereinbefore), or $R^{8a}$ represents $CH_2OC(O)R^{11}$, in which $R^{11}$ represents phenyl, linear, branched or cyclic $C_{1-6}$ alkyl (which latter group is optionally substituted by a substituent selected from OH, $CO_2H$ and phenyl), or $OR^{12}$ (wherein $R^{12}$ represents phenyl or linear, branched or cyclic $C_{1-6}$ alkyl (which latter group is optionally substituted by a substituent selected from OH, $CO_2H$ and phenyl)).

When $R^4$ represents $C(O)OR^{8b}$, preferred compounds of the invention include those in which $R^{8b}$ represents linear or branched $C_{1-2}$ alkylphenyl or phenyl (which latter two groups are optionally substituted as specified hereinbefore).

Preferred compounds of the invention include those in which $R^1$ is attached to the phenyl ring at the 3-position, relative to the —CH(OH)— group to which the phenyl ring is also attached. The optional substituent $R^2$ is preferably attached to the phenyl ring at the 5-position, relative to the —CH(OH)— group to which the phenyl ring is also attached.

When the group $N(R^5)R^6$ represents a structural fragment Ia, the fragment is preferably unsubstituted.

More preferred compounds of the invention include those in which:

$R^1$ represents $N(R^5)R^6$;

$R^3$ is either absent or, if present, represents methyl or chloro, preferably in the 2-position relative to the —$CH_2$— group to which the phenyl ring is also attached;

$R^{8a}$ represents linear or branched $C_{1-4}$ alkyl (optionally interrupted by oxygen) or $C_{4-5}$ cyclic alkyl interrupted by oxygen;

$R^5$ represents $C_{1-4}$ alkyl or, together with $R^6$ and the nitrogen atom to which $R^5$ and $R^6$ are attached, represents a 5- or 6-membered nitrogen containing ring, optionally substituted with a =O group;

$R^6$ represents $C_{1-4}$ alkyl, $C(O)$—$C_{1-6}$ alkyl (e.g. $C(O)$—$C_{1-4}$ alkyl) or, together with $R^5$ and the nitrogen atom to which $R^5$ and $R^6$ are attached, represents a 5- or 6-membered nitrogen-containing ring, optionally substituted with a =O group.

Compounds of formula I in which the fragment

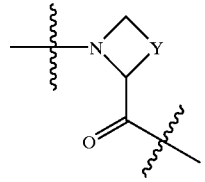

is in the S-configuration are preferred.

Compounds of formula I in which the fragment

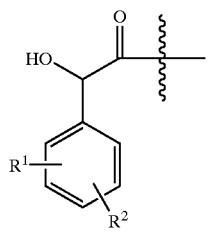

is in the R-configuration are preferred.

The wavy lines on the bonds in the above two fragments signify the bond positions of the fragments.

Preferred compounds of formula I include the compounds of the Examples described hereinafter.

Preparation

According to the invention there is also provided a process for the preparation of compounds of formula I which comprises:

(i) the coupling of a compound of formula II,

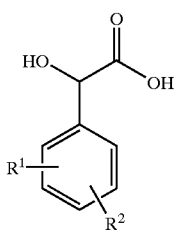

II wherein $R^1$ and $R^2$ are as hereinbefore defined with a compound of formula III,

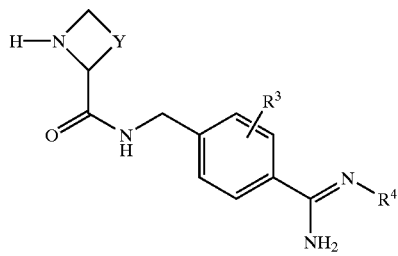

III wherein Y, $R^3$ and $R^4$ are as hereinbefore defined, for example in the presence of a coupling agent (e.g. EDC, DCC, HBTU, HATU, TBTU, PyBOP or oxalyl chloride in DMF), an appropriate base (e.g. pyridine, 2,4,6-trimethylpyridine, 2,4,6-collidine, DMAP, TEA or DIPEA) and a suitable organic solvent (e.g. dichloromethane, acetonitrile or DMF);

(ii) the coupling of a compound of formula IV,

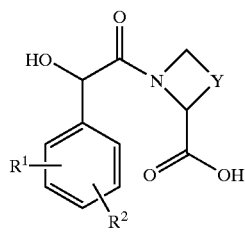

IV wherein $R^1$, $R^2$ and Y are as hereinbefore defined with a compound of formula V,

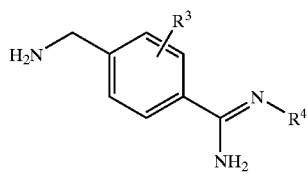

V wherein $R^3$ and $R^4$ are as hereinbefore defined, for example in the presence of a coupling agent (e.g. oxalyl chloride in DMF, EDC, DCC, HBTU, HATU, PyBOP or TBTU), an appropriate base (e.g. pyridine, 2,4,6-trimethylpyridine, DMAP, TEA, 2,4,6-collidine or DIPEA) and a suitable organic solvent (e.g. dichloromethane, acetonitrile or DMF);

(iii) for compounds of formula I in which $R^4$ represents OH or $OR^{8a}$, reaction of a compound of formula VI,

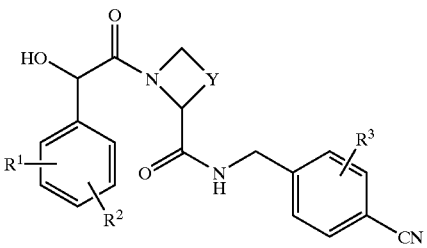

VI wherein $R^1$, $R^2$, Y and $R^3$ are as hereinbefore defined with a compound of formula VII,

VII wherein $R^1$ represents H or $R^{8a}$ and $R^{8b}$ is as hereinbefore defined, for example at between 40 and 60° C., in the presence of a suitable base (e.g. TEA) and an appropriate organic solvent (e.g. THF, $CH_3CN$, DMF or DMSO), optionally by pre-treating the compound of formula VI with gaseous HCl, in the presence of a lower alkyl (e.g. $C_{1-6}$ alkyl) alcohol (e.g. ethanol) at, for example, 0° C., to form a compound of formula VIII,

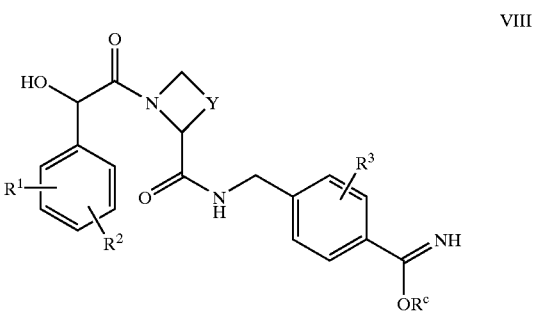

VIII wherein $R^c$ represents lower (e.g. $C_{1-6}$) alkyl, such as ethyl, and $R^1$, $R^2$, Y and $R^3$ are as hereinbefore defined, which compound may be isolated if desired;

(iv) for compounds of formula I in which $R^4$ represent OH or $OR^{8a}$, reaction of a compound corresponding to a compound of formula I, in which, in place of $R^4$, a protecting group $C(O)OR^{b1}$ is present, in which $R^{b1}$ represents a group such as 2-trimethylsilylethyl, $C_{1-6}$ alkyl or alkylphenyl (e.g. benzyl), with a compound of formula VII as hereinbefore defined, for example under similar reaction conditions to those described hereinbefore for preparation of compounds of formula I (step (iii)) (the skilled person will appreciate that in such a reaction the diprotected amidine (i.e. $C(O)OR^{b1}$ and $OR^a$ protected) derivative may, in some cases, be isolated if desired, and the $C(O)OR^{b1}$ group then removed using conventional techniques);

(v) for compounds of formula I in which $R^4$ represents $C(O)OR^{8b}$, reaction of a compound of formula I in which $R^4$ represents H with a compound of formula IX, $L^1$—$C(O)OR^{8b}$      IX wherein $L^1$ represents a suitable leaving group, such as halo or p-nitrophenoxy, and $R^{8b}$ is as hereinbefore defined, for example 0° C. in the presence of a suitable base (e.g. NaOH) and an appropriate organic solvent (e.g. THF) and/or water;

(vi) for compounds of formula I in which $R^4$ represents $OR^{8a}$, reaction of a corresponding compound of formula I in which $R^4$ represents OH with a compound of formula IXA,

  IXA wherein $R^{8a}$ and $L^1$ are as hereinbefore defined, for example at between 0° C. and reflux temperature, optionally in the presence of an appropriate solvent (e.g. DCM, THF, MeCN or DMF) and a suitable base (e.g. $Et_3N$ or pyridine);

(vii) for compounds of formula I in which $R^4$ represents $R^{8c}$, wherein $R^{8c}$ represents $C(R^{10a})(R^{10b})OC(O)R^{11}$ or $C(R^{10a})(R^{10b})OC(O)N(H)R^{12}$, reaction of a corresponding compound of formula IXB,

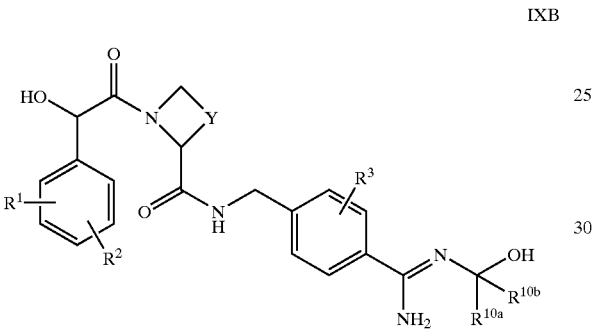  IXB wherein $R^1$, $R^2$, Y, $R^3$, $R^{10a}$ and $R^{10b}$ are as hereinbefore defined with a compound of formula IXC,

  IXC wherein $R^{13}$ represents $R^{11}$ or $N(H)R^{12}$, and $L^1$, $R^{11}$ and $R^{12}$ are as hereinbefore defined, for example under conditions described hereinbefore (process step (vi));

(viii) for compounds of formula I in which $R^4$ represents $R^{8c}$, reaction of a corresponding compound of formula I in which $R^4$ represents H with a compound of formula IXD,

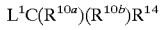  IXD wherein $R^{14}$ represents $OC(O)R^{11}$, $NHC(O)OR^{12}$ or $OC(O)N(H)R^{12}$, and $L^1$, $R^{10a}$, $R^{10b}$, $R^{11}$ and $R^{12}$ are as hereinbefore defined, for example under conditions described hereinbefore (process step (vi));

(ix) for compounds of formula I in which $R^1$ includes a S(O) or a $S(O)_2$ group, oxidation of a corresponding compound of formula I wherein $R^1$ includes a S group, in the presence of an appropriate amount of a suitable oxidising agent (e.g. mCPBA or potassium peroxymonosulfate) and an appropriate organic solvent (e.g. $CH_2Cl_2$, methanol, water or mixtures thereof (e.g. methanol/water)).

Compounds of formula II are available using known and/or standard techniques.

For example, compounds of formula II may be prepared by reaction of an aldehyde of formula X,

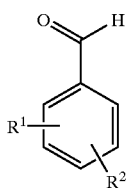  X wherein $R^1$ and $R^2$ are as hereinbefore defined, with:

(a) a compound of formula XI,

  XI wherein R" represents H or $(CH_3)_3Si$, for example at room, or elevated, temperature (e.g. below 100° C.) in the presence of a suitable organic solvent (e.g. chloroform or methylene chloride) and, if necessary, in the presence of a suitable base (e.g. TEA) and/or a suitable catalyst system (e.g. benzylammonium chloride or zinc iodide), followed by hydrolysis under conditions that are well known to those skilled in the art (e.g. as described hereinafter);

(b) NaCN or KCN, for example in the presence of $NaHSO_3$ and water, followed by hydrolysis;

(c) chloroform, for example at elevated temperature (e.g. above room temperature but below 100° C.) in the presence of a suitable organic solvent (e.g. chloroform) and, if necessary, in the presence of a suitable catalyst system (e.g. benzylammonium chloride), followed by hydrolysis;

(d) a compound of formula XII,

  XII wherein M represents Mg or Li, followed by oxidative cleavage (e.g. ozonolysis or osmium or ruthenium catalysed) under conditions which are well known to those skilled in the art; or (e) tris(methylthio)methane under conditions which are well known to those skilled in the art, followed by hydrolysis in the presence of e.g. HgO and $HBF_4$.

The enantiomeric forms of compounds of formula II (i.e. those compounds having different configurations of substituents about the C-atom α- to the $CO_2H$ group) may be separated by an enantiospecific derivatisation step. This may be achieved, for example by an enzymatic process. Such enzymatic processes include, for example, transesterification of the α-OH group at between room and reflux temperature (e.g. at between 45 and 55° C.) in the presence of a suitable enzyme (e.g. Lipase PS Amano), an appropriate ester (e.g. vinyl acetate) and a suitable solvent (e.g. methyl tert-butyl ether). The derivatised isomer may then be separated from the unreacted isomer by conventional separation techniques (e.g. chromatography).

Groups added to compounds of formula II in such a derivatisation step may be removed either before any further reactions or at any later stage in the synthesis of compounds of formula I. The additional groups may be removed using conventional techniques (e.g. for esters of the α-OH group, hydrolysis under conditions known to those skilled in the art (e.g. at between room and reflux temperature in the presence of a suitable base (e.g. NaOH) and an appropriate solvent (e.g. MeOH, water or mixtures thereof))).

Compounds of formula III may be prepared by reaction of a compound of formula XIII

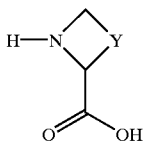

XIII wherein Y is as hereinbefore defined with a compound of formula V as hereinbefore defined, for example under conditions such as those described hereinbefore for synthesis of compounds of formula I (see, for example, process steps (i) and (ii)).

Compounds of formula IV are readily available using known techniques. For example, compounds of formula IV may be prepared by reaction of a compound of formula II as hereinbefore defined with a compound of formula XIII as hereinbefore defined, for example under conditions such as those described hereinbefore for synthesis of compounds of formula I (see, for example, process steps (i) and (ii)).

Compounds of formula V are known in the literature, and/or may be prepared using known techniques. For example compounds of formula V may be prepared by reduction of a compound of formula XIV,

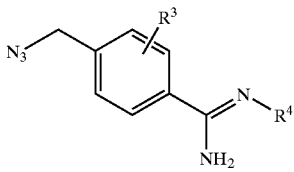

XIV wherein $R^3$ and $R^4$ are as hereinbefore defined, under conditions that are well known to those skilled in the art.

Compounds of formula VI may be prepared in accordance with peptide coupling techniques, for example in analogous fashion to the methods described hereinbefore for compounds of formula I (see, for example, process steps (i) and (ii)). If desired, compounds of formula VIII may also be prepared in this way.

Compounds of formula IXB may be prepared by reaction of a corresponding compound of formula I in which $R^4$ represents H with an excess of a compound of formula IVA,

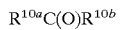

XIVA wherein $R^{10a}$ and $R^{10b}$ are as hereinbefore defined, for example under conditions known to those skilled in the art.

Compounds of formula X are commercially available, are well known in the literature, or are available using known and/or standard techniques.

For example, compounds of formula X may be prepared by reduction of a compound of formula XV,

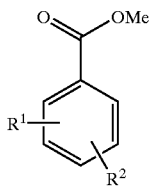

XV wherein $R^1$ and $R^2$ are as hereinbefore defined, in the presence of a suitable reducing agent (e.g. DIBAL-H).

Alternatively, compounds of formula X may be prepared by oxidation of a compound of formula XVI,

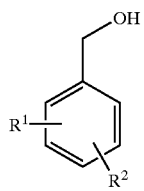

XVI wherein $R^1$ and $R^2$ are as hereinbefore defined, in the presence of a suitable oxidising agent (e.g. pyridinium chlorochromate or a combination of DMSO and oxalyl chloride).

Compounds of formulae II, IV, VI, VIII, X, XV and XVI in which $R^1$ includes a S(O) or a S(O)$_2$ group, may be prepared by oxidation of a corresponding compound of formula II, IV, VI, VIII, X, XV or XVI (as appropriate) wherein $R^1$ includes a S group, for example as described hereinbefore.

Compounds of formulae VII, IX, IXA, IXC, IXD, XI, XII, XIII, XIV, XIVA, XV and XVI, and derivatives thereof, are either commercially available, are known in the literature, or may be obtained either by analogy with the processes described herein, or by conventional synthetic procedures, in accordance with standard techniques, from readily available starting materials using appropriate reagents and reaction conditions (e.g. as described hereinafter).

Substituents on the aromatic and/or non-aromatic, carbocyclic and heterocyclic ring(s) in compounds of formulae I, II, III, IV, V, VI, VII, VIII, IX, IXA, IXB, IXC, IXD, X, XIII, XIV, XV and XVI may be introduced and/or interconverted using techniques well known to those skilled in the art. For example, nitro may be reduced to amino, amino may be alkylated or acylated to give alkyl- and/or acylamino, amino may be converted to pyrrolo (by condensation with a 2,5-dimethoxytetrahydrofuran in the presence of a catalyst, such as phosphorous pentoxide), amino may be converted (via diazotisation) to halo or (e.g. via reaction with a 1,4- or 1,5-dihaloalkyl compound or a β- or γ-haloester) to a nitrogen-containing ring (optionally substituted with a =O group), iodo may be converted to nitrogen-containing heterocycles (for example imidazolyl and piperidinyl, by treatment with imidazole or piperidine under Buchwald conditions), nitrogen hydroxy may be alkylated to give alkoxy, alkoxy may be hydrolysed to hydroxy, alkenes may be hydrogenated to alkanes, halo may be hydrogenated to H, etc. In this regard, compounds of formula XV in which $R^1$ represents —N(CH$_3$)$_2$ and $R^2$ represent chloro or methyl, may be obtained from commercially available iodo-chloro or iodo-methyl disubstituted benzoic acid methyl esters using Pd-catalysed amination, for example as described by Wolfe et al in *Tetrahedron Lett.* 38, 6367 (1997), followed by either reductive amination (for example using HCHO and a reducing agent such as Na(CN)BH$_3$ or a combination of Pt(IV) oxide and hydrogen), or alkylation (for example using MeI and an appropriate base), of the resultant aniline. Compounds of formula XV in which R$^1$ represents —S(O)$_m$CH$_3$ (in which m is as hereinbefore defined) and R$^2$ represents chloro or methyl, may be obtained from the resultant aniline described above (or from the corresponding benzoic acid) via diazotisation, followed by treatment of the diazonium salt with potassium ethyl xanthate, and then hydrolysis of the intermediate to give the corresponding thiophenol, for example as described by Tarbell et al in "*Organic Synthesis*", Coll. Vol. III, p 809–11 (1955). The resultant thiophenol may then be alkylated (for example using an appropriate alkyl iodide in the presence of a suitable base in EtOH), and then (if necessary) oxidised to form the sulfone or sulfoxide (for example using mCPBA in CH$_2$Cl$_2$ or potassium peroxymonosulfate in methanouwater).

The compounds of formula I may be isolated from their reaction mixtures using conventional techniques.

It will be appreciated by those skilled in the art that in the processes described above the functional groups of intermediate compounds may need to be protected by protecting groups.

Functional groups which it is desirable to protect include hydroxy, amino, aldehyde, 2-hydroxycarboxylic acid and carboxylic acid. Suitable protecting groups for hydroxy include trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acid include C$_{1-6}$ alkyl or benzyl esters. Suitable protecting groups for amino and amidino include t-butyloxycarbonyl, benzyloxycarbonyl or 2-trimethylsilylethoxycarbonyl (Teoc). Amidino nitrogens may also be protected by hydroxy or alkoxy groups, and may be either mono- or diprotected. Aldehydes may be protected as acetals by reacting with e.g. ethylene glycol. 2-Hydroxy carboxylic acids may be protected by condensing with e.g. acetone.

The protection and deprotection of functional groups may take place before or after coupling, or before or after any other reaction in the abovementioned schemes.

Protecting groups may be removed in accordance with techniques which are well known to those skilled in the art and as described hereinafter.

Persons skilled in the art will appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

For example, this is particularly true in respect of the synthesis of compounds of formula I in which R$^4$ does not represent H. In this case, OH, OR$^{8a}$, C(O)OR$^{8b}$ and/or R$^{8c}$ groups may be introduced at an earlier stage in the overall synthesis using the process steps described hereinbefore (see, for example, process steps (iii) to (viii)). Further, the mandelic acid OH group of compounds of formulae II and IV may need to be protected prior to the coupling steps described above.

Accordingly, the order and type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", 2nd edition, T W Greene & P G M Wutz, Wiley-Interscience (1991).

Protected derivatives of compounds of formula I may be converted chemically to compounds of formula I using standard deprotection techniques (e.g. hydrogenation). The skilled person will also appreciate that certain compounds of formula I may also be referred to as being "protected derivatives" of other compounds of formula I.

Medical and Pharmaceutical Use

Compounds of the invention may possess pharmacological activity as such. Compounds of the invention that may possess such activity include, but are not limited to, those in which R$^4$ is H.

However, other compounds of formula I (including those in which R$^4$ is not H) may not possess such activity, but may be administered parenterally or orally, and thereafter metabolised in the body to form compounds that are pharmacologically active (including, but not limited to, corresponding compounds in which R$^4$ is H). Such compounds (which also includes compounds that may possess some pharmacological activity, but that activity is appreciably lower than that of the "active" compounds to which they are metabolised), may therefore be described as "prodrugs" of the active compounds.

Thus, the compounds of the invention are useful because they possess pharmacological activity, and/or are metabolised in the body following oral or parenteral administration to form compounds which possess pharmacological activity. The compounds of the invention are therefore indicated as pharmaceuticals.

According to a further aspect of the invention there is thus provided the compounds of the invention for use as pharmaceuticals.

In particular, compounds of the invention are potent inhibitors of thrombin either as such and/or (e.g. in the case of prodrugs), are metabolised following administration to form potent inhibitors of thrombin, for example as demonstrated in the tests described below.

By "prodrug of a thrombin inhibitor", we include compounds that form a thrombin inhibitor, in an experimentally-detectable amount, and within a predetermined time (e.g. about 1 hour), following oral or parenteral administration.

The compounds of the invention are thus expected to be useful in those conditions where inhibition of thrombin is required.

The compounds of the invention are thus indicated in the treatment and/or prophylaxis of thrombosis and hypercoagulability in blood and tissues of animals including man.

It is known that hypercoagulability may lead to thrombo-embolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S or heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis. The compounds of the invention are thus indicated both in the therapeutic and/or prophylactic treatment of these conditions.

The compounds of the invention are further indicated in the treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction.

Moreover, the compounds of the invention are expected to have utility in prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis.

In addition to its effects on the coagulation process, thrombin is known to activate a large number of cells (such as neutrophils, fibroblasts, endothelial cells and smooth muscle cells). Therefore, the compounds of the invention may also be useful for the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

Compounds of the invention that inhibit trypsin and/or thrombin may also be useful in the treatment of pancreatitis.

According to a further aspect of the present invention, there is provided a method of treatment of a condition where inhibition of thrombin is required which method comprises administration of a therapeutically effective amount of a compound of the invention, or a pharmaceutically acceptable salt thereof, to a person suffering from, or susceptible to such a condition.

The compounds of the invention will normally be administered orally, intravenously, subcutaneously, buccally, rectally, dermally, nasally, tracheally, bronchially, by any other parenteral route or via inhalation, in the form of pharmaceutical preparations comprising active compound either as a free base, or a pharmaceutically acceptable non-toxic organic or inorganic acid addition salt, in a pharmaceutically acceptable dosage form. Depending upon the disorder and patient to be treated and the route of administration, the compositions may be administered at varying doses.

The compounds of the invention may also be combined and/or co-administered with any antithrombotic agent with a different mechanism of action, such as the antiplatelet agents acetylsalicylic acid, ticlopidine, clopidogrel, thromboxane receptor and/or synthetase inhibitors, fibrinogen receptor antagonists, prostacyclin mimetics and phosphodiesterase inhibitors and ADP-receptor ($P_2T$) antagonists.

The compounds of the invention may further be combined and/or co-administered with thrombolytics such as tissue plasminogen activator (natural, recombinant or modified), streptokinase, urokinase, prourokinase, anisoylated plasminogen-streptokinase activator complex (APSAC), animal salivary gland plasminogen activators, and the like, in the treatment of thrombotic diseases, in particular myocardial infarction.

According to a further aspect of the invention there is thus provided a pharmaceutical formulation including a compound of the invention, in admixture with a pharmaceutically acceptable adjuvant, diluent or carrier.

Suitable daily doses of the compounds of the invention in therapeutical treatment of humans are about 0.001–100 mg/kg body weight at peroral administration and 0.001–50 mg/kg body weight at parenteral administration.

The compounds of the invention have the advantage that they may, or may be metabolised to compounds that may, be more efficacious, be less toxic, be longer acting, have a broader range of activity, be more potent, produce fewer side effects, be more easily absorbed than, or have other useful pharmacological, physical, or chemical, properties over, compounds known in the prior art.

Biological Tests

Test A

Determination of Thrombin Clotting Time (TT)

The inhibitor solution (25 μL) was incubated with plasma (25 μL) for three minutes. Human thrombin (T 6769; Sigma Chem. Co or Hematologic Technologies) in buffer solution, pH 7.4 (25 μL, 4.0 NIH units/mL), was then added and the clotting time measured in an automatic device (KC 10; Amelung).

The thrombin clotting time (TT) is expressed as absolute values (seconds) as well as the ratio of TT without inhibitor ($TT_0$) to TT with inhibitor ($TT_i$). The latter ratios (range 1–0) were plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations were processed on a PC using the software program GraFit Version 3, setting equation equal to: Start at 0, define end=1 (Erithacus Software, Robin Leatherbarrow, Imperial College of Science, London, UK).

Test B

Determination of Thrombin Inhibition with a Chromogenic, Robotic Assay

The thrombin inhibitor potency was measured with a chromogenic substrate method, in a Plato 3300 robotic microplate processor (Rosys AG, CH-8634 Hombrechtikon, Switzerland), using 96-well, half volume microtitre plates (Costar, Cambridge, Mass., USA; Cat No 3690). Stock solutions of test substance in DMSO (72 μL), 0.1–1 mmol/L, were diluted serially 1:3 (24+48 μL) with DMSO to obtain ten different concentrations, which were analysed as samples in the assay. 2 μL of test sample was diluted with 124 μL assay buffer, 12 μL of chromogenic substrate solution (S-2366, Chromogenix, Mölndal, Sweden) in assay buffer and finally 12 μL of α-thrombin solution (Human α-thrombin, Sigma Chemical Co. or Hematologic Technologies) in assay buffer, were added, and the samples mixed. The final assay concentrations were: test substance 0.00068–13.3 μmol/L, S-2366 0.30 mmol/L, α-thrombin 0.020 NIHU/mL. The linear absorbance increment during 40 minutes incubation at 37° C. was used for calculation of percentage inhibition for the test samples, as compared to blanks without inhibitor. The $IC_{50}$-robotic value, corresponding to the inhibitor concentration which caused 50% inhibition of the thrombin activity, was calculated from a log concentration vs. % inhibition curve.

Test C
Determination of the Inhibition Constant K for Human Thrombin $K_i$-determinations were made using a chromogenic substrate method, performed at 37° C. on a Cobas Bio centrifugal analyser (Roche, Basel, Switzerland). Residual enzyme activity after incubation of human α-thrombin with various concentrations of test compound was determined at three different substrate concentrations, and was measured as the change in optical absorbance at 405 nm.

Test compound solutions (100 μL; normally in buffer or saline containing BSA 10 g/L) were mixed with 200 μL of human α-thrombin (Sigma Chemical Co) in assay buffer (0.05 mol/L Tris-HCl pH 7.4, ionic strength 0.15 adjusted with NaCl) containing BSA (10 g/L), and analysed as samples in the Cobas Bio. A 60 μL sample, together with 20 μL of water, was added to 320 μL of the substrate S-2238 (Chromogenix AB, Mölndal, Sweden) in assay buffer, and the absorbance change (ΔA/min) was monitored. The final concentrations of S-2238 were 16, 24 and 50 μmol/L and of thrombin 0.125 NIH U/mL.

The steady state reaction rate was used to construct Dixon plots, i.e. diagrams of inhibitor concentration vs. 1/(ΔA/min). For reversible, competitive inhibitors, the data points for the different substrate concentrations typically form straight lines which intercept at x=-Ki.

Test D
Determination of Activated Partial Thromboplastin Time (APTT)

APTT was determined in pooled normal human citrated plasma with the reagent PTT Automated 5 manufactured by Stago. The inhibitors were added to the plasma (10 μL inhibitor solution to 90 μL plasma) and incubated with the APTT reagent for 3 minutes followed by the addition of 100 μL of calcium chloride solution (0.025 M) and APTT was determined by use of the coagulation analyser KC10 (Amelung) according to the instructions of the reagent producer.

The clotting time is expressed as absolute values (seconds) as well as the ratio of APTT without inhibitor ($APTT_0$) to APTT with inhibitor ($APTT_i$). The latter ratios (range 1–0) were plotted against the concentration of inhibitor (log transformed) and fitted to sigmoidal dose-response curves according to the equation $$y=a/[1+(x/IC_{50})^s]$$

where: a=maximum range, i.e. 1; s=slope of the dose-response curve; and $IC_{50}$=the concentration of inhibitor that doubles the clotting time. The calculations were processed on a PC using the software program GraFit Version 3, setting equation equal to: Start at 0, define end=1 (Erithacus Software, Robin Leatherbarrow, Imperial College of Science, London, UK).

$IC_{50}$APTT is defined as the concentration of inhibitor in human plasma that doubled the Activated Partial Thromboplastin Time.

Test E
Determination of Thrombin Time Ex Vivo

The inhibition of thrombin after oral or parenteral administration of the compounds of formula I, dissolved in ethanol:Solutol™:water (5:5:90), were examined in conscious rats which, one or two days prior to the experiment, were equipped with a catheter for blood sampling from the carotid artery. On the experimental day blood samples were withdrawn at fixed times after the administration of the compound into plastic tubes containing 1 part sodium citrate solution (0.13 mol per L) and 9 parts of blood. The tubes were centrifuged to obtain platelet poor plasma. The plasma was used for determination of thrombin time or ecarin clotting time (ECT) as described below.

The citrated rat plasma, 100 μL, was diluted with a saline solution, 0.9%, 100 μL, and plasma coagulation was started by the addition of human thrombin (T 6769, Sigma Chem Co, USA or Hematologic Technologies) in a buffer solution, pH 7.4, 100 μL, or ecarin (Pentapharm). The clotting time was measured in an automatic device (KC 10, Amelung, Germany).

Where a "prodrug" compound of formula I was administered, concentrations of the appropriate active thrombin inhibitor of formula I (e.g. the free amidine compound) in the rat plasma were estimated by the use of standard curves relating the thrombin time or ecarin clotting time in the pooled citrated rat plasma to known concentrations of the corresponding "active" thrombin inhibitor dissolved in saline.

Based on the estimated plasma concentrations of the active thrombin inhibitor (which assumes that thrombin time or ECT prolongation is caused by the aforementioned compound) in the rat, the area under the curve after oral and/or parenteral administration of the corresponding prodrug compound of formula I was calculated (AUCpd) using the trapezoidal rule and extrapolation of data to infinity.

The bioavailability of the active thrombin inhibitor after oral or parenteral administration of the prodrug was calculated as below:

[(AUCpd/dose)/(AUCactive,parenteral/dose]×100 where AUCactive,parenteral represents the AUC obtained after parenteral administration of the corresponding active thrombin inhibitor to conscious rats as described above.

Test F
Determination of Thrombin Time in Urine Ex Vivo

The amount of the "active" thrombin inhibitor that was excreted in urine after oral or parenteral administration of "prodrug" compounds of the invention, dissolved in ethanol:Solutol™:water (5:5:90), was estimated by determination of the thrombin time in urine ex vivo (assuming that thrombin time prolongation is caused by the aforementioned compound).

Conscious rats were placed in metabolism cages, allowing separate collection of urine and faeces, for 24 hours following oral administration of compounds of the invention. The thrombin time was determined on the collected urine as described below.

Pooled normal citrated human plasma (100 μL) was incubated with the concentrated rat urine, or saline dilutions thereof, for one minute. Plasma coagulation was then initiated by the administration of human thrombin (T 6769, Sigma Chem Company) in buffer solution (pH 7.4; 100 μL). The clotting time was measured in an automatic device (KC 10; Amelung).

The concentrations of the active thrombin inhibitor in the rat urine were estimated by the use of standard curves relating the thrombin time in the pooled normal citrated human plasma to known concentrations of the aforementioned active thrombin inhibitor dissolved in concentrated rat urine (or saline dilutions thereof). By multiplying the total rat urine production over the 24 hour period with the estimated mean concentration of the aforementioned active inhibitor in the urine, the amount of the active inhibitor excreted in the urine (AMOUNTpd) could be calculated.

The bioavailability of the active thrombin inhibitor after oral or parenteral administration of the prodrug was calculated as below:

[(AMOUNTpd/dose)/(AMOUNTactive,parenteral/dose)]×100 where AMOUNTactive,parenteral represents the amount excreted in the urine after parenteral administration of the corresponding active thrombin inhibitor to conscious rats as described above.

Test G
Metabolic Activation of Prodrug Compounds In Vitro

Prodrug compounds of formula I were incubated at 37° C. with liver microsomes or 10,000 g (referring to the centrifuge speed) supernatant fractions (i.e. s9 fraction) prepared from human or rat liver homogenate. The total protein concentration in the incubations were 1 or 3 mg/mL dissolved in 0.05 mol/L TRIS buffer (pH 7.4), and with the cofactors NADH (2.5 mmol/L) and NADPH (0.8 mmol/L) present. The total volume of the incubate was 1.2 mL. The initial prodrug concentrations were 5 or 10 μmol/L. Samples were collected from the incubate at regular intervals more than 60 minutes after the start of the incubations. Samples (25 μL) from the incubate were mixed with an equal volume of human or rat plasma and an appropriate amount of thrombin, and the clotting time (i.e. thrombin time) was measured on a coagulometer (KC 10; Amelung). The amount of "active" thrombin inhibitor formed was estimated by the use of standard curves relating the thrombin time in pooled citrated human or rat plasma to known concentrations of the corresponding "active thrombin inhibitor".

The amount of "active" thrombin inhibitor was alternatively, or in addition to the above-mentioned method, estimated by the use of LC-MS.

EXAMPLES

The invention is illustrated by way of the following examples. The amino acids Pro and Aze are defined as the S-isomers if not otherwise specified. The examples were obtained as diastereoisomers if not otherwise specified.

Example 1

Ph(3-N(Me)$_2$)-(R)- or -(S)CH(OH)—C(O)-Aze-Pab×HOAc (i) Ph(3-N(Me)$_2$)—CHO

A mixture of Ph(3-N(Me)$_2$)—CH$_2$OH (1.9 g; 12.6 mmol) and MnO$_2$ (8.8 g; 100 mmol) in CH$_2$Cl$_2$ was stirred at room temperature for 2.5 days. The mixture was filtered through Celite® and the filtrate was evaporated. The crude product was flash chromatographed on silica gel using isopropylether:trimethylpentane (7:3) as eluent. Yield 0.93 g (50%).

$^1$H-NMR (400 MHz; CDCl$_3$): δ 9.89 (s, 1H), 7.37 (m, 1H), 7.17–7.25 (m, 2H), 7.05 (m, 1H), 2.98 (s, 6H).

(ii) Ph(3-N(Me)$_2$)-(R,S)CH(OSiMe$_3$)N TMS-CN (0.75 mL; 6.0 mmol) was added dropwise to a mixture of Ph(3-N(Me)$_2$)—CHO (0.9 g; 6.0 mmol; from step (i) above) and Et$_3$N (0.08 mL; 6.0 mmol) in CH$_2$Cl$_2$ (15 mL). The reaction mixture was stirred at room temperature for 24 hours. Additional Et$_3$N (0.08 mL; 6.1 mmol) and TMS-CN (0.75 mL; 6.0 mmol) were added and the stirring was continued for another 24 hours. The reaction mixture was evaporated yielding 1.35 g (90%) of the sub-tide compound.

$^1$H-NMR (400 MHz; CDCl$_3$): δ 7.27 (t, 1H), 6.78–6.84 (m, 2H), 6.74 (dd, 1H), 5.47 (s, 1H), 3.00 (s, 6H).

(iii) Ph(3-N(Me)$_2$)-(R,S)CH(OH)—C(O)OH

A mixture of Ph(3-N(Me)$_2$)-(R,S)CH(OSiMe$_3$)CN (1.35 g; 5.43 mmol; from step (ii) above) and HCl (20 mL; conc.) was stirred at room temperature for 10 minutes, and then at between 90° C. and 100° C. (in an oil bath) for 3 hours. The reaction mixture was evaporated and H$_2$O was added. The acidic water layer was washed with Et2O and put on a cation exchange resin (IR-120, 10–15 g; the cation exchanger was pre-prepared by suspending it in NaOH (2 M)), and then the slurry was poured into a column. The cation exchanger was subsequently washed with HCl (2 M; 2×50 mL), H$_2$O (2×50 mL), and then with H$_2$O until the pH was neutral and the product was eluted with NH$_4$OH/aq (1 M). The resultant water layer was evaporated and freeze dried yielding 0.78 g (74%) of the sub-tide compound.

LC-MS: (M–1) 194 m/z; $^1$H-NMR (500 MHz; CD$_3$OD): δ 7.15 (t, 1H), 6.94 (s, 1H), 6.84 (d, 1H), 6.69 (dd, 1H), 4.85 (s, 1H), 2.92 (s, 6H).

(iv) Ph(3-N(Me)$_2$)-(R)- or -(S)CH(OH)—C(O)OH×HCl

The enantiomers of Ph(3-N(Me)$_2$)-(R,S)CH(OH)—C(O)OH (step (iii) above) were separated by preparative HPLC using Chiralcel™ OD as a stationary phase and n-heptane:2-propanol:formic acid (80:20:1) as mobile phase. The enantiomer that eluted last was evaporated and freeze dried, then redissolved in water, and 3 eq. of 1 M HCl was added. The solution was freeze dried to yield the hydrochloride salt which gave an $[\alpha]_D^{20}$ of –63.7° (c=1.0, MeOH). The enantiomeric excess was 97% as determined by analytical chiral HPLC.

(v) Ph(3-N(Me)$_2$)-(R)- or -(S)CH(OH)—C(O)-Aze-Pab(Z)

DIPEA (1.03 mL; 6.15 mmol) was added at 0° C. to a mixture of Ph(3-N(Me)$_2$)-(R)- or -(S)CH(OH)—C(O)OH× HCl (0.36 g; 1.54 mmol; the separated/isolated product of step (iv) above), H-Aze-Pab(Z)×2 HCl (0.743 g; 1.69 mmol; see international patent application WO 97/02284) and TBTU (0.543 g; 1.69 mmol) in DMF (10 mL). The reaction mixture was stirred at room temperature for 4 days, poured onto H$_2$O (400 mL) and the pH was adjusted to 10 by adding NaHCO$_3$/aq. The water layer was extracted with EtOAc and then the organic layer was washed with NaHCO$_3$/aq, H$_2$O and NaCl/aq, dried (Na$_2$SO$_4$), and evaporated. The crude product was purified by flash chromatography on silica gel using CH$_2$Cl$_2$:MeOH (95:5) as eluent. The product was further purified by preparative HPLC to give 203 mg (24%) of the sub-title compound.

LC-MS: (M +1) 544; (M–1) 542 m/z; $^1$H-NMR (400 MHz; CDCl$_3$): δ 8.20 (t, 1H), 7.75 (d, 2H), 7.43 (d, 2H), 7.18–7.38 (m, 6H), 6.61–6.72 (m, 3H), 5.20 (s, 2H), 4.88 (s, 1H), 4.84 (dd, 1H), 4.36–4.52 (m, 2H), 4.03 (m, 1H), 3.63 (m, 1H), 2,93 (s, 6H), 2.54 (m, 1H), 2.30 (m, 1H).

(vi) Ph(3-N(Me)$_2$)-(R)- or -(S)CH(OH)—C(O)-Aze-Pab× HOAc

A mixture of Ph(3-N(Me)$_2$)-(R)- or -(S)CH(OH)—C(O)-Aze-Pab(Z) (112 mg; 0.206 mmol; from step (v) above), HOAc (0.41 mL) and Pd/C 10% in EtOH (7 mL) was hydrogenated at atmospheric pressure and room temperature for 3 hours. The reaction mixture was filtered through Celite® and the filtrate was evaporated and freeze dried (×2) yielding 90 mg (93%) of white crystals.

LC-MS: (M +1) 410; (M−1) 408 m/z; $^1$H-NMR (500 MHz; CD$_3$OD): δ 7.74 (d, 2H), 7.54 (d, 2H), 7.21 (t, 1H), 6.85 (s, 1H), 6.73–6.77 (m, 2H), 5.11 (s, 1H), 4.77 (dd, 1H), 4.52 (dd, 2H), 4.30 (m, 1H), 3.92 (m, 1H), 2.92 (s, 6H), 2.46 (m, 1H), 2.27 (m, 1H). $^{13}$C-NMR (125 MHz; CDCl$_3$): (carbonyl and/or amidine carbons): δ 173.3, 171.9, 167.0.

Example 2

Ph(3-N(Me)$_2$)-(R)- or -(S)CH(OH)—CO-Aze-Pab (OMe)

(i) 4-(Amino, Methoxyiminomethyl)benzyl Azide

A mixture of O-methylhydroxylamine hydrochloride (10.5 g; 125 mmol), triethylamine (56 mL) and methanol (200 mL) was added to 4-ethylimidatobenzyl azide hydrochloride (22.5 g; 110 mmol; prepared according to the method described in WO 94/29336) in diethyl ether. The reaction mixture was stirred at room temperature for 3 to 4 days. Most of the methanol was removed in vacuo and replaced with ethyl acetate. The organic layer was washed with H$_2$O, HOAc/aq (1.5%; pH 4), NaHCO$_3$/aq and dried (Na$_2$SO$_4$). The resultant solution was diluted with ethyl acetate to 500 mL, and 25 mL of the diluted solution was concentrated to estimate the yield. The total yield was about 20 g.

$^1$H-NMR (400 MHz; CD$_3$OD): δ 7.66 (d, 2H), 7.36 (d, 2H), 4.37 (s, 2H), 3.83 (s, 3H).

(ii) H-Pab(OMe)

Platinum oxide (200 mg) was added to a solution of 4-(amino, methoxyiminomethyl)benzyl azide (10 g; 0.049 mol; from step (i) above) in 200 mL of ethanol. The mixture was hydrogenated at atmospheric pressure for 8 hours, filtered through Celite™ and concentrated. The crude product was used directly in the following step.

$^1$H-NMR (400 MHz; CD$_3$OD): δ 7.60 (d, 2H), 7.37 (d, 2H), 3.81 (s, 3H), 3.80 (s, 2H).

(iii) Boc-Aze-Pab(OMe)

DIPEA (17.5 mL; 105 mmol) was added to an ice-cold solution of Boc-Aze-OH (9.7 g; 48 mmol; see international patent application WO 97/02284) and H-Pab(OMe) (9.4 g; 52 mmol; from step (ii) above) and TBTU (18.5 g; 58 mmol) in DMF (100 mL), and the mixture was stirred overnight at RT. The resulting mixture was poured onto water (50 mL), the pH was adjusted to ca. 9, and the mixture was extracted three times with EtOAc. The combined organic layer was washed with NaHCO$_3$(aq.), water and brine, dried (Na$_2$SO$_4$), and concentrated. The crude product was purified with flash chromatography (Si-gel; EtOAc). The yield was 11.9 g (69%).

$^1$H-NMR (400 MHz; CDCl$_3$): δ 7.60 (d, 2H); 7.31 (d, 2H); 4.78 (b, 2H); 4.69 (t, 1H); 4.50 (b, 2H); 3.92 (s+m, 4H); 3.79 (m, 1H); 2.46 (b, 2H); 2.04 (s, 3H).

(iv) Aze-Pab(OMe)×2HCl

A solution of Boc-Aze-Pab(OMe) (9.4 g; 26 mmol; from step (iii) above) in EtOAc (250 mL) was saturated with HCl(g). EtOH (abs.; 125 mL) was added to the resultant emulsion and the mixture was sonicated for 10 minutes. EtOAc was added until the solution became turbid, whereafter the sub-title product soon crystallized. Yield 6.7 g (77%).

LC-MS: (M+1) 263 (m/z); $^1$H-NMR (400 MHz; CD$_3$OD): δ 7.74 (d, 2H); 7.58 (d, 2H); 5.13 (t, 1H); 4.57 (m, 2H); 4.15 (m, 2H); 3.97 (s+m, 4H); 2.87 (m, 1H); 2.57 (m, 1H). $^{13}$C-NMR (75 MHz; CDCl$_3$): (carbonyl and/or amidine carbons): δ 168.9; 168.8; 161.9.

(v) Ph(3-N(Me)$_2$)-(R) or -(S)CH(OH)—C(O)-Aze-Pab (OMe)

A mixture of Ph(3-N(Me)$_2$)-(R)- or -(S)CH(OH)—C(O) OH×HCl (118 mg; 0.51 mmol; see Example 1(iv) above) and HATU (214 mg; 0.56 mmol) in DMF (3 mL) was stirred at 0° C. for 1.5 hours. H-Aze-Pab(OMe)×2 HCl (189 mg, 0.56 mmol; from step (iv) above), 2,4,6-trimethylpyridine (0.3 mL, 2.25 mmol) and DMF (3 mL) were mixed separately before being added dropwise to the first mixture at 0° C. The reaction mixture was stirred at 0° C. for 3 hours, put in the refrigerator for 3 days and evaporated. The crude product was purified by preparative HPLC to give 140 mg (62%) of the title compound.

LC-MS: (M+1) 440; (M−1) 438 m/z; $^1$H-NMR (500 MHz; CD$_3$OD): δ 8.60 (t, 1H), 7.61 (d, 2H), 7.37 (d, 2H), 7.22 (t, 1H), 6.87 (s, 1H), 6.77 (d, 2H), 5.08 (s, 1H), 4.75 (dd, 1H), 4.46 (dd, 2H), 4.26 (m, 1H), 3.90 (m, 1H), 3.84 (s, 3H), 2.94 (s, 6H), 2.44 (m, 1H), 2.26 (m, 1H). $^{13}$C-NMR (125 MHz; CD$_3$OD): (carbonyl and/or amidine carbons): δ 173.3, 171.8, 154.9.

Example 3

Ph(3-SMe)-(R)- or -(S)CH(OH)C(O)-Aze-Pab×TFA (i) Ph(3-SMe)-(R,S)CH(OTMS)CN

To a solution of Ph(3-SMe)—CHO (19.8 g, 130 mmol) and ZnI$_2$ (2.1 g, 6.50 mmol) in CH$_2$Cl$_2$ (450 mL) at 0° C. under nitrogen there was added dropwise trimethylsilyl cyanide (14.2 g, 143 mmol). After stirring overnight at 25° C., the orange mixture was quenched with H$_2$O (450 mL). The organic layer was separated and washed with saturated brine (300 mL), dried (Na$_2$SO$_4$), filtered and concentrated in vacuo to give 32.0 g (98% crude) of the sub-title compound as an orange oil which was used without purification.

$^1$H NMR (300 MHz; CDCl$_3$): δ 7.20–7.41 (m, 4H), 5.50 (s, 1H), 2.51 (s, 3H), 0.23 (s, 9H).

(ii) Ph(3-SMe)-(R,S)CH(OH)C(O)OH

A solution of Ph(3-SMe)-(R,S)CH(OTMS)CN (32.0 g, 130 mmol; see step (i) above) in concentrated HCl (250 mL) was refluxed for 2.5 h. The mixture was made basic with 6 N NaOH (450 mL) and washed with Et$_2$O (3×300 mL) to remove organic impurities. The aqueous layer was acidified with 6 N HCl (150 mL) and extracted with EtOAc (4×500 mL). The combined extracts were dried (Na$_2$SO$_4$), filtered and concentrated in vacuo to yield 22.6 g (90% crude yield) of the sub-title compound as an orange oil which crystallized to a yellow-tan solid on standing.

$^1$H NMR (300 MHz; CD$_3$OD): δ 7.20–7.40 (m, 4H), 5.12 (s, 1H), 2.50 (s, 3H).

(iii) Ph(3-SMe)-(R) or -(S)CH(OH)C(O)OH (a) and Ph(3-SMe)-(S) or -(R)CH(OAc)C(O)OH (b)

A mixture of Ph(3-SMe)-(R,S)CH(OH)C(O)OH (2.0 g, 10.1 mmol; see step (ii) above), Lipase PS Amano (1.0 g), vinyl acetate (5.0 mL) and MTBE (5.0 mL) was heated at 45° C. for 24 h. The reaction was filtered and the filter cake washed with EtOAc (100 μL). The filtrate was concentrated in vacuo and chromatographed on silica gel, eluting with a mixture of CHCl$_3$:MeOH:NH$_3$ (aq., sat.) (6:3:1), to afford 630 mg, (32%) of sub-title compound (a) as a yellow oil and 850 mg (35%) of sub-title compound (b) as a tan solid.

For sub-title compound (a): $^1$H NMR (300 MHz; CD$_3$OD): δ 7.38 (s, 1H), 7.10–7.25 (m, 3H), 5.08 (s, 1H), 2.40 (s, 3H). $^{13}$C NMR (75 MHz; CD$_3$OD): δ 178.4, 142.6, 140.2, 130.0, 127.3, 126.4, 125.2, 75.5, 15.8. HPLC Analysis: 98.9%, 96.0% ee; $[\alpha]_D^{25}$=−119.8° (c=1.0, MeOH); CI-MS: (M+1) 199 m/z; For sub-title compound (b): $^1$H NMR (300 MHz; CD$_3$OD): δ 7.62 (s, 1H), 7.32–7.44 (m, 3H), 5.82 (s, 1H), 2.62 (s, 3H), 2.30 (s, 3H).

(iv) Boc-Aze-Pab×HCOOH

Ammonium formate (3.0 g; 50 mmol) and Pd/C (5%; 1.0 g) were added to a solution of Boc-Aze-Pab(Z) (4.7 g; 10 mmol; see international patent application WO 94/29336) in 50 mL of MeOH. Formic acid (1.0 g; 22 mmol) was added and the mixture was stirred for 30 minutes. The reaction mixture was filtered through Hyflo and the solution was concentrated. The crude product was suspended in $CH_2Cl_2$ (50 mL), filtered and washed with more $CH_2Cl_2$. The solid material was dried and used in the following step without further purification.

(v) Boc-Aze-Pab(Teoc)

Teoc-p-nitrophenyl carbonate (3.5 g; 12.3 mmol) was added to a solution of Boc-Aze-Pab×HCOOH (3.7 g; 10 mmol; see step (iv) above) in THF (100 mL) whereafter a solution of $K_2CO_3$ (1.8 g; 13 mmol) in water (20 mL) was added over 2 minutes. The resultant solution was stirred for 3 days, concentrated, and the remainder was taken up in EtOAc (150 mL) and NaOH (aq.; 0.5M; 50 mL). The organic layer was washed with brine (2×50 mL), dried ($Na_2SO_4$) and concentrated. The crude product was purified using flash chromatography (Si-gel; methylene chloride:acetone; 4:1). Yield 4.6 g (96%).

$^1$H-NMR (500 MHz; $CDCl_3$): δ 7.86 (d, 2H), 7.39 (d, 2H), 4.72 (bt, 1H), 4.7–4.5 (br, 2H), 3.93 (m, 1H), 3.81 (m, 1H), 2.48 (br, 2H), 1.43 (s, 9H), 0.09 (s, 9H).

(vi) H-Aze-Pab(Teoc)×HCl

A solution of Boc-Aze-Pab(Teoc) (4.6 g; 9.6 mmol; see step (v) above) in methylene chloride (150 mL) was saturated with dry HCl. The solution was kept at RT in a stoppered flask for 10 minutes, whereafter it was concentrated. Yield 4.2 g (97%).

$^1$H-NMR (400 MHz; $CD_3OD$): δ 7.80 (d, 2H), 7.60 (d, 2H), 5.10 (m, 1H), 4.60 (bs, 2H), 4.15 (m, 1H), 3.97 (q, 1H), 2.86 (m, 1H), 2.57 (m, 1H), 0.11 (s, 9H).

(vii) Ph(3-SMe)-(R) or -(S)CH(OH)C(O)-Aze-Pab(Teoc)

A mixture of Ph(3-SMe)-(R) or -(S)CH(OH)C(O)OH (300 mg, 1.51 mmol; see step (iii)(a) above), H-Aze-Pab (Teoc) (627 mg, 1.66 mmol; see step (vi) above), TBTU (632 mg, 1.66 mmol), and DIPEA (391 mg, 3.03 mmol) in DMF (8.0 mL) was stirred at 0° C. and then at 25° C. overnight. The reaction was quenched with $H_2O$ (50 mL) and extracted with EtOAc (3×50 mL). The combined extracts were dried ($Na_2SO_4$), filtered and concentrated in vacuo. The residue was chromatographed on silica gel, eluting with $CH_2Cl_2$:MeOH (9:1), to afford 150 mg (18%) of the sub-title compound as a white solid.

$^1$H NMR (300 MHz; $CD_3OD$): δ 7.74–7.86 (m, 2H), 7.10–7.45 (m, 6H), 5.10–5.15 (m, 2H), 4.70–4.81 (m, 1H), 3.90–4.44 (m, 6H), 2.50 (s, 3H), 2.10–2.32 (m, 2H), 1.02–1.18 (m, 2H), 0.10 (s, 9H). API-MS: (M+1) 557 m/z.

(viii) Ph(3-SMe)-(R) or -(S)CH(OH)C(O)-Aze-Pab×TFA

A mixture of Ph(3-SMe)-(R) or -(S)CH(OH)C(O)-Aze-Pab(Teoc) (80 mg, 0.19 mmol; see step (vii) above) and TFA (2.0 mL) in $CH_2Cl_2$ (2 mL) was stirred at 0° C. for 3 hours. The solution was concentrated in vacuo and the residue was dissolved in water and freeze-dried to afford 90 mg (87%) of the title compound.

LC-MS: (M+1) 413; (M−1) 411 m/z; $^1$H NMR (400 MHz; $CD_3OD$; mixture of rotamers): δ 7.74 (m, 2H), 7.52 (m, 2H), 7.38–7.13 (m, 4H), 5.2–5.0 (m, 1H), 4.79 (m, 1H), 4.62–3.94 (m, 4H), 2.68, 2.49 (2m, 1H), 2.28, 2.14 (2m, 1H), 2.45 (s, 3H). $^{13}$C NMR (100 MHz): δ 185.0, 172.8, 171.8, 167.0.

Example 4

Ph(3-$SO_2$Me)-(R) or -(S)CH(OH)C(O)-Aze-Pab× TFA (i) Ph(3-$SO_2$Me)-(R) or -(S)CH(OH)C(O)OH

A mixture of Ph(3-SMe)-(R) or -(S)CH(OH)C(O)OH (890 mg, 4.49 mmol; see Example 3(iii)(a) above) and Oxone® (8.3 g, 13.5 mmol) in MeOH (40 mL) and $H_2O$ (25 mL) was stirred at 0° C. and then at 25° C. overnight. The solids were filtered and washed with EtOAc (200 mL). The filtrate was concentrated in vacuo, diluted with $H_2O$ (50 mL), and then extracted with EtOAc (4×60 mL). The combined organic extracts were dried ($Na_2SO_4$), filtered and then concentrated in vacuo. The residue was chromatographed on silica gel, eluting with $CHCl_3$:MeOH:$NH_3$ (aq., sat.) (6:3:1), to afford 150 mg (15%) of the sub-title compound as a white solid.

$^1$H NMR (300 MHz; $CD_3OD$): δ 8.10 (s, 1H), 7.80–7.88 (m, 2H), 7.55 (t, J=7.5 Hz, 1H), 5.02 (s, 1H), 3.10 (s, 3H). $^{13}$C NMR (75 MHz; $CD_3OD$): δ 178.4, 145.6, 142.2, 133.2, 130.3, 127.4, 126.2, 75.5, 42.4. HPLC Analysis: 94.8%, >99% ee; $[α]_D^{25}$=−86.20 (c=1.0, MeOH); API-MS: (M−1) 229 m/z.

(ii) Ph(3-$SO_2$Me)-(R) or -(S)CH(OH)C(O)-Aze-Pab(Teoc)

A mixture of Ph(3-$SO_2$Me)-(R) or -(S)CH(OH)C(O)OH (400 mg, 1.74 mmol; see step (i) above), H-Aze-Pab(Teoc) (720 mg, 1.91 mmol; see Example 3(vi) above), PyBOP (995 mg, 1.91 mmol), and 2,4,6-collidine (463 mg, 3.83 mmol) in DMF (10 mL) was stirred at 0° C. and then at 25° C. overnight. The mixture was quenched with $H_2O$ (50 mL) and extracted with EtOAc (3×50 mL). The combined extracts were dried ($Na_2SO_4$), filtered and then concentrated in vacuo. The residue was chromatographed on silica gel, eluting with $CHCl_3$:MeOH (15:1), to afford 570 mg (57%) of the sub-title compound as a white solid.

$^1$H NMR (300 MHz; $CD_3OD$): δ 7.58–8.10 (m, 6H), 7.40–7.50 (m, 2H), 5.32 (s, 1H), 5.25 (s, 1H), 4.70–4.81 (m, 1H), 3.97–4.54 (m, 6H), 3.20 (s, 3H), 2.10–2.82 (m, 2H), 1.02–1.18 (m, 2H), 0.10 (s, 9H). API-MS: (M+1) 589 m/z.

(iii) Ph(3-$SO_2$Me)-(R) or -(S)CH(OH)C(O)-Aze-Pab×TFA

To a cold solution of Ph(3-$SO_2$Me)-(R) or -(S)CH(OH)C(O)-Aze-Pab(Teoc) (65 mg, 0.11 mmol; see step (ii) above) in methylene chloride (0.5 mL) was added TFA (3 mL), and the solution was stirred for 100 min. The resultant solution was concentrated, water was added, and the aqueous solution was freeze-dried, yielding 60 mg (96%) of the title compound.

LC-MS: (M+1) 445; (M−1) 443 m/z; $^1$H NMR (400 MHz; $CD_3OD$): δ 8.10–7.45 (m, 8H), 5.34, 5.25 (2m, 1H), 4.81 (m, 1H), 4.62–3.93 (m, 4H), 3.10 (s, 3H), 2.70, 2.54 (m, 1H), 2.28, 2.17 (m, 1H). $^{13}$C NMR (carbonyl and/or amidine carbons; 100 MHz): δ 172.2, 171.7, 167.0, 161.0.

Example 5

Ph(3-Cl,5-NMeAc)-(R) or -(S)CH(OH)C(O)-Aze-Pab×TFA (i) Ph(3-Cl,5-$NO_2$)-(R,S)CH(OTMS)CN

To a solution of 3-chloro-5-nitrobenzaldehyde (24.1 g, 0.13 mol) in $CH_2Cl_2$ (1.0 L) was added $ZnI_2$ (2.1 g, 6.5 mmol). The resulting suspension was cooled to 0° C. and trimethylsilyl cyanide (13.9 g, 0.14 mol) was added over 5 min. The solution was stirred at 0° C. for 3 h, warmed to 25° C. and stirred for 18 h. The reaction was diluted with $H_2O$ and the organics were separated, dried ($Na_2SO_4$), filtered and then concentrated in vacuo to afford 36.8 g (99%) of the sub-title compound as an oil.

$^1$H NMR (300 MHz; $CDCl_3$): δ 8.21–8.29 (m, 2H), 7.83 (s, 1H), 5.59 (s, 1H), 0.36 (s, 9H).

(ii) Ph(3-Cl,5-$NO_2$)-(R,S)CH(OH)C(O)OH

A solution of Ph(3-Cl,5-$NO_2$)(R,S)CH(OTMS)CN (59.0 g, 0.209 mol; see step (i) above) in concentrated HCl (600 mL) was heated to reflux for 3 h. The solution was cooled and concentrated in vacuo to 500 mL. The acidic solution was extracted with Et₂O (4x), the organics were washed with brine (2x), dried (Na₂SO₄), filtered and then concentrated in vacuo to afford 48.4 g (93%) of the sub-title compound as a solid that was used without further purification.

¹H NMR (300 MHz; CD₃OD): δ 8.33 (m, 1H), 8.23 (m, 1H), 7.94 (m, 1H), 5.34 (s, 1H).

(iii) Ph(3-Cl,5-NO₂)-(R) or -(S)CH(OH)C(O)OH (a) and Ph(3-Cl, 5-NO₂)-(S) or -(R)CH(OAc)C(O)OH (b)

A mixture of Ph(3-Cl,5-NO₂)-(R,S)CH(OH)C(O)OH (17.1 g, 73.84 mmol; see step (ii) above) and Lipase PS Amano (8.5 g) in vinyl acetate (300 mL) and MTBE (300 mL) was stirred at 55° C. for 24 h. The reaction was filtered through Celite® and the filter cake washed with Et2O. The filtrate was concentrated in vacuo and then flash chromatographed on silica gel, eluting with CHCl₃:CH₃CN:TFA (180:20:1), to afford 7.1 g (42%) of the sub-title compound (a) as a solid and 10.7 g (52%) of the sub-tide compound (b) as a solid.

For sub-title compound (a): ¹H NMR (300 MHz; CD₃OD): δ 8.33 (s, 1H), 8.22 (s, 1H), 7.95 (s, 1H), 5.34 (s, 1H). ¹³C NMR (75 MHz; CD₃OD): δ 174.6, 150.2, 145.2, 136.3, 133.8, 124.1, 121.1, 72.7. API-MS: (M−1) 230 m/z; $[\alpha]_D^{25}$=−101.2° (c=1.0, MeOH); HPLC Analysis: 99.6%, 99% ee; For sub-title compound (b): ¹H NMR (300 MHz; CD₃OD): δ 8.32 (m, 1H), 8.28 (m, 1H), 7.96 (m, 1H), 6.10 (s, 1H), 2.21 (s, 3H).

(iv) Ph(3-Cl,5-NH₂)-(R) or -(S)CH(OH)C(O)OH

A mixture of Ph(3-Cl,5-NO₂)-(R) or -(S)CH(OH)C(O)OH (3.9 g, 16.8 mmol; see step (iii)(a) above) and platinum (IV) oxide (0.4 g) in EtOH (200 mL) at 40° C. was stirred under a hydrogen atmosphere for 4 h. The mixture was filtered through a pad of Celite® and the filter cake washed with EtOH. The filtrate was concentrated in vacuo to afford 3.5 g (ca. 100%) of the sub-title compound as a crushable foam that was used without further purification.

¹H NMR (300 MHz; CD₃OD): δ 6.77 (m, 1H), 6.71 (m, 1H), 6.57 (m, 1H), 4.78 (s, 1H).

(v) Ph(3-Cl,5-NHMe)-(R) or -(S)CH(OH)C(O)OH
Method A:

A mixture of Ph(3-Cl,5-NH₂)-(R) or -(S)CH(OH)C(O)OH (3.5 g, 16.8 mmol; see step (iv) above) and formaldehyde (1.8 mL of 37 wt % in H₂O, 23.9 mmol) in EtOH (400 mL) was stirred at 25° C. for 18 h. The solution was concentrated in vacuo to give a crushable foam that was combined with platinum(IV) oxide (0.35 g) in EtOH (400 mL) and stirred under a hydrogen atmosphere for 48 h. The mixture was filtered through a pad of Celite® and the filter cake washed with EtOH. The organics were concentrated in vacuo and flash chromatographed on silica gel, eluting with CHCl₃:MeOH:NH₃ (aq., sat.) (14:5:1), to afford 1.0 g (28%) of the ammonium salt of the sub-title compound as a crushable foam. The sub-title compound was obtained by flushing the corresponding ammonium salt through a pad of Amberlite® CG-50 with CH₃CN:MeOH (3:1).
Method B:

A mixture of Ph(3-Cl,5-NH₂)-(R) or -(S)CH(OH)C(O)OH (8.67 g, 43.0 mmol; see step (iv) above) and methyl iodide (6.10 g, 43.0 mmol) in CH₃CN (500 mL) and MeOH (100 mL) was heated to 50° C. for 24 h. The solution was concentrated in vacuo and flash chromatographed on silica gel, eluting with CHCl₃:MeOH:NH₃ (aq., sat.) (14:5:1), to afford 2.9 g (31%) of the ammonium salt of the sub-title compound as a solid. The sub-title compound was obtained by flushing the corresponding ammonium salt through a pad of Amberlite® CG-50 with CH₃CN:MeOH (3:1).

¹H NMR (300 MHz; CD₃OD): δ 6.68 (m, 1H), 6.61 (m, 1H), 6.50 (m, 1H), 4.98 (s, 1H), 2.75 (s, 3H). ¹³C NMR (75 MHz; CD₃OD): δ 176.8, 153.4, 144.1, 136.7, 116.3, 113.2, 111.0, 74.7, 31.3. API-MS: (M+1) 216 m/z; HPLC Analysis: 97.2%, 97.9% ee; $[\alpha]_D^{25}$=−81.6° (c=1.0, MeOH);

(vi) Ph(3-Cl,5-NMeAc)-(R) or -(S)CH(OH)C(O)OH

A solution of Ph(3-Cl,5-NHMe)-(R) or -(S)CH(OH)C(O)OH (1.0 g, 4.64 mmol; see step (v) above) in MeOH (100 mL) was treated with four portions of acetic anhydride (40.47 g, 4.64 mmol each portion) over a period of 72 h. The solution was made basic with 2 N NaOH, stirred for 3 h, neutralized with 2 N HCl and then concentrated in vacuo. Flash chromatography (2x) on silica gel, eluting with CHCl₃:MeOH:NH₃ (aq., sat.) (6:3:1), afforded 0.83 g (69%) of the ammonium salt of the sub-title compound as a crushable foam. The sub-title compound was obtained by flushing the corresponding ammonium salt through a pad of Amberlite® CG-50 with CH₃CN:MeOH (3:1).

¹H NMR (300 MHz; CD₃OD): δ 7.54 (s, 1H), 7.35 (s, 2H), 5.19 (s, 1H), 3.26 (s, 3H), 1.88 (s, 3H). ¹³C NMR (75 MHz; CD₃OD): δ 175.3, 172.8, 146.8, 145.2, 136.2, 128.0, 127.5, 125.4, 73.2, 37.6, 22.5. API-MS: (M+1) 258 m/z; HPLC Analysis: 98.5%, 97.4% ee; $[\alpha]_D^{25}$=−97.5° (c=1.0, MeOH);

(vii) Ph(3-Cl,5-NMeAc)-(R) or -(S)CH(OH)C(O)-Aze-Pab (Teoc)

To a mixture of Ph(3-Cl,5-NMeAc)-(R) or -(S)CH(OH)C(O)OH (0.34 g, 1.32 mmol; see step (vi) above) and H-Aze-Pab(Teoc) (0.52 g, 1.39 mmol; see Example 3(vi) above) in DMF (15 mL) at 0° C. was added collidine (0.35 g, 2.90 mmol) and PyBOP (0.75 g, 1.45 mmol). The solution was stirred at 0° C. for 2 h, warmed to 25° C. and stirred for 2 h then concentrated in vacuo. Flash chromatography (2x) on silica gel, eluting with CHCl₃:EtOH (95:5), afforded 0.36 g (44%) of the sub-title compound as a crushable foam.

¹H NMR (300 MHz; CD₃OD, mixture of rotamers): δ 7.78 (d, 2H, J=9 Hz), 7.25–7.55 (m, 5H), 5.25 and 4.78 (2m, 1H), 5.22 and 5.15 (2s, 1H), 3.93–4.56 (m, 6H), 3.23 (s, 3H), 2.12–2.78 (m, 2H), 1.87 (s, 3H), 1.04–1.11 (m, 1H), 0.06 (s, 9H). API-MS: (M+1) 616 m/z.

(viii) Ph(3-Cl,5-NMeAc)-(R) or -(S)CH(OH)C(O)-Aze-Pab×TFA

A solution of Ph(3-Cl,5-NMeAc)-(R) or -(S)CH(OH)C(O)-Aze-Pab(Teoc) (73 mg, 0.12 mmol; see step (vii) above) in TFA (5.0 mL) was stirred at room temperature for 80 min, after which time the resulting solution was evaporated to dryness. The remaining solid was dissolved in water, and the solution was freeze-dried, yielding 70 mg (98%) of the title compound as a foam.

LC-MS: (M+1) 472 m/z; ¹H NMR (400 MHz; D₂O): δ 7.74 (dd, 2H), 7.55–7.10 (m, 5H), 5.36, 5.20 (2s, 1H), 5.23, 4.88 (2m, 1H), 4.60–4.05 (m, 4H), 3.38, 3.20 (2s, 3H), 2.80, 2.60 (2m, 1H), 2.38–2.20 (m, 1.5H), 1.87 (2.5H). ¹³C NMR (carbonyl and/or amidine carbons; 100 MHz): δ 173.9, 173.3, 172.6, 166.5, 163.3.

Example 6

Ph(3-Cl,5-NMe₂)-(R) or -(S)CH(OH)C(O)-Aze-Pab×2TFA (i) 3-Chloro-5-N,N-dimethylaminobenzyl Alcohol To a solution of 3-chloro-5-nitrobenzyl alcohol (12.5 g, 66.6 mmol) in EtOH (750 mL) was added platinum(IV) oxide (1.25 g). The resulting suspension was purged with hydrogen for 3 h. Formaldehyde solution (37 wt % in H₂O, 97 mL, 1.3 mol) was added and the mixture was stirred under a hydrogen atmosphere for 18 h. The solution was filtered through a pad of Celite® and concentrated in vacuo to give the crude product. Flash chromatography on silica gel, eluting with Hex:EtOAc (7:3), gave 8.2 g (66%) of the sub-title compound as an oil.

$^1$H NMR (300 MHz; CDCl$_3$): δ 6.67 (s, 1H), 6.55–6.63 (m, 2H), 4.58 (d, 2H, J=7 Hz), 2.96 (s, 6H), 1.74 (t, 1H, J=7 Hz). CI-MS: (M+1) 185 m/z.

(ii) 3-Chloro-5-N,N-dimethylaminobenzaldehyde

To a solution of DMSO (7.58 g, 97.0 mmol) in CH$_2$Cl$_2$ (100 μL) at −78° C. was added oxalyl chloride (6.16 g, 48.5 mmol) over the course of 10 min. After an additional 15 min at −78° C., a solution of 3-chloro-5-N,N-dimethylaminobenzyl alcohol (8.18 g, 44.1 mmol; see step (i) above) in CH$_2$Cl$_2$ (100 mL) was added over the course of 15 min. The resulting solution was stirred at −78° C. for 1 h prior to the addition of DIPEA (28.5 g, 220.5 mmol). The solution was warmed to 25° C. and stirred for 18 h, before being concentrated in vacuo to give the crude product. Flash chromatography on silica gel, eluting with Hex:EtOAc (5:1), gave 7.50 g (93%) of the sub-title compound as a yellow solid.

$^1$H NMR (300 MHz; CDCl$_3$): δ 9.88 (s, 1H), 7.15 (m, 1H), 7.05 (m, 1H), 6.87 (m, 1H), 3.04 (s, 6H).

(iii) Ph(3-Cl,5-NMe)-(R,S)CH(OTMS)CN

To a solution of 3-chloro-5-N,N-dimethylaminobenzaldehyde (7.5 g, 40.8 mmol; see step (ii) above) in CH$_2$Cl$_2$ (300 mL) was added ZnI$_2$ (0.65 g, 2.04 mmol). The resulting suspension was cooled to 0° C. and trimethylsilyl cyanide (4.5 g, 44.9 mmol) was added over 5 min. The solution was stirred at 0° C. for 1 h before being warmed to 25° C., and stirred for 2 h. The resulting mixture was diluted with H$_2$O and the organics were separated, dried (Na$_2$SO$_4$), filtered and then concentrated in vacuo to afford 11.7 g (100%) of the sub-title compound as an oil.

$^1$H NMR (300 MHz; CDCl$_3$): δ 6.75 (m, 1H), 6.60–6.68 (m, 2H), 5.39 (s, 1H), 2.97 (s, 6H), 0.28 (s, 9H).

(iv) Ph(3-Cl,5-NMe$_2$)-(R,S)CH(OH)C(O)OH

Ph(3-Cl,5-NMe$_2$)-(R,S)CH(OTMS)CN (11.7 g, 41.4 mmol; see step (iii) above) was dissolved in concentrated HCl (300 mL) and heated to reflux for 1.5 h. The solution was cooled and concentrated in vacuo. The residue was dissolved in H$_2$O, neutralized with NaHCO$_3$ and concentrated in vacuo. The mixture of organics and salts were slurried in MeOH, filtered and then concentrated to give the crude product. Flash chromatography on silica gel, eluting with CHCl$_3$:MeOH:conc. NH$_4$OH (aq) (6:3:1), afforded 9.0 g (95%) of the ammonium salt of the sub-title compound as a solid.

$^1$H NMR (300 MHz; CD$_3$OD): δ 6.77–6.82 (m, 2H), 6.58 (m, 1H), 4.80 (s, 1H), 2.94 (s, 6H).

(v) Ph(3-Cl,5-NMe$_2$)-(R) or -(S)CH(OH)C(O)OH (a) and Ph(3-Cl, 5-NMe$_2$)-(S) or -(R)CH(OAc)C(O)OH (b)

A mixture of Ph(3-Cl,5-NMe$_2$)-(R,S)CH(OH)C(O)OH (1.0 g; see step (iv) above) and Lipase PS Amano (0.5 g) in vinyl acetate (10 mL) and MTBE (10 mL) was stirred at 45° C. for 48 h. The reaction was filtered through Celite® and the filter cake washed with MeOH. The filtrate was concentrated in vacuo and flash chromatographed on silica gel, eluting with CHCl$_3$:MeOH:NH$_3$ (aq., sat.) (6:3:1), to afford 0.40 g (40%) of the sub-title compound (a) as a crushable foam and 0.45 g (38%) of the sub-title compound (b) as a crushable foam. Sub-title compound (a) could be further purified by crystallization from CH$_2$Cl$_2$ and MeOH.

For sub-title compound (a): $^1$H NMR (300 MHz; CD$_3$OD): δ 6.81 (m, 1H), 6.74 (m, 1H), 6.57 (m, 1H), 4.98 (s, 1H), 2.87 (s, 6H). $^{13}$C NMR (75 MHz; CD$_3$OD): δ 180.0, 152.9, 144.8, 135.6, 116.1, 112.2, 110.9, 76.9, 40.5. API-MS: (M+1) 230 m/z; HPLC Analysis: 98.5%, 97.9% ee; $[α]_D^{25}$=−73.5° (c=0.5, DMSO); For sub-title compound (b): $^1$H NMR (300 MHz; CD$_3$OD): δ 6.77–6.83 (m, 2H), 6.64 (m, 1H), 5.67 (s, 1H), 2.94 (s, 6H), 2.14 (s, 3H).

(vi) Ph(3-Cl,5-NMe$_2$)-(R) or -(S)CH(OH)C(O)-Aze-Pab (Teoc)

To a mixture of Ph(3-Cl,5-NMe$_2$)-(R) or -(S)CH(OH)C(O)OH (0.11 g, 0.48 mmol; see step (v)(a) above) and H-Aze-Pab(Teoc) (0.20 g, 0.53 mmol, see Example 3(vi)) in DMF (15 mL) at 0° C. was added DIPEA (0.12 g, 0.96 mmol) and TBTU (0.17 g, 0.53 mmol). The solution was stirred at 0° C. for 2 h, warmed to 25° C. and stirred for 18 h then concentrated in vacuo. Flash chromatography on silica gel, eluting with a gradient of CH$_2$Cl$_2$:MeOH (from 100:0 to 95:5), afforded 0.25 g of the sub-title compound which was subjected to a second flash chromatography on silica gel, eluting with EtOAc:MeOH (30:1), to give 0.22 g (78%) of the sub-title compound as a crushable foam.

$^1$H NMR (300 MHz; CD$_3$OD, mixture of rotamers): δ 7.78 (d, 2H, J=9 Hz), 7.42 (d, 2H, J=9 Hz), 6.62–6.75 (m, 3H), 5.14 and 4.78 (2m, 1H), 5.07 (m, 1H), 4.15–4.57 (m, 4H), 3.94–4.12 (m, 2H), 2.96 (s, 6H), 2.05–2.75 (m, 2H), 1.04–1.13 (m, 2H), 0.08 (s, 9H). API-MS: (M+1) 588 m/z.

(vii) Ph(3-Cl,5-NMe$_2$)-(R) or -(S)CH(OH)C(O)-Aze-Pab×2TFA

To an ice-cold solution of Ph(3-Cl,5-NMe$_2$)-(R) or -(S)CH(OH)C(O)-Aze-Pab(Teoc) (84 mg, 0.14 mmol; see step (vi) above) was added TFA (4 mL), and the resultant solution was stirred at 0° C. for 2 h. The solution was concentrated to give a residue that was dissolved in water and then freeze-dried. This gave 78 mg (81%) of the tide compound as a white powder.

LC-MS: (M−1) 442 m/z; $^1$H NMR (400 MHz; CD$_3$OD; mixture of rotamers): δ 7.78–7.49 (m, 4H), 6.94–6.79 (m, 4H), 5.15, 5.08 (m, 1H), 5.20, 4.79 (2m, 1H), 4.51 (AB part of an ABX spectrum; 2H), 4.41–3.95 (m, 2H), 2.98 (s, 6H), 2.69, 2.52 (2m, 1H), 2.28, 2.14 (2m, 1H). $^{13}$C NMR (carbonyl and/or amidine carbons; 100 MHz): δ 172.5, 171.7, 166.9, 161.0, 160.7.

Example 7

Ph(3-NMeAc)-(R) or -(S)CH(OH)C(O)-Aze-Pab×HOAc (i) Ph(3-NO$_2$)-(R) or -(S)CH(OH)C(O)OH (a) and Ph(3-NO$_2$)-(S) or -(R)CH(OAc)C(O)OH (b)

A mixture of Ph(3-NO$_2$)-(R,S)CH(OH)C(O)OH (25 g, 126 mmol), Lipase PS Amano (12.5 g), vinyl acetate (150 mL) and MTBE (375 mL) was heated at 45° C. for 24 h. The reaction was filtered and the filter cake washed with EtOAc (500 mL). The filtrate was concentrated in vacuo and chromatographed on silica gel, eluting with a mixture of CHCl$_3$:MeOH: NH$_3$ (aq., sat.) (6:3:1), to afford 9.0 g, (36%) of the sub-title compound (a) as a yellow oil and 6.5 g (21%) of sub-title compound (b) as a tan solid.

For sub-title compound (a): $^1$H NMR (300 MHz; CD$_3$OD): δ 8.34 (s, 1H), 8.25 (d, J=7.5 Hz, 1H), 7.82 (d, J=7.5 Hz, 1H), 7.62 (t, J=7.5 Hz, 1H), 5.30 (s, 1H). For sub-title compound (b): $^1$H NMR (300 MHz; CD$_3$OD): δ 8.34 (s, 1H), 8.25 (d, J=7.5 Hz, 1H), 7.82 (d, J=7.5 Hz, 1H), 7.62 (t, J=7.5 Hz, 1H), 5.82 (s, 1H), 2.20 (s, 3H).

(ii) Ph(3-NH$_2$)-(R) or -(S)CH(OH)C(O)OH

A mixture of Ph(3-NO$_2$)-(R) or -(S)CH(OH)C(O)OH (8.0 g, 40.6 mmol; see step (i)(a) above) and 10% palladium on carbon (800 mg) in MeOH (200 mL) was stirred at 25° C. under one atmosphere of hydrogen overnight. The mixture was filtered through a pad of Celite®, washing with EtOAc (250 mL). The filtrate was concentrated in vacuo to give 7.0 g (100%) of the sub-title compound as a white foam.

¹H NMR (300 MHz; CD₃OD): δ 7.0–7.12 (m, 1H), 6.75–6.90 (m, 2H), 6.60–6.70 (m, 1H), 4.80 (s, 1H).

(iii) Ph(3-NHMe)-(R) or -(S)CH(OH)C(O)OH

A mixture of Ph(3-NH₂)-(R) or -(S)CH(OH)C(O)OH (2.9 g, 17.3 mmol; see step (ii) above) and methyl iodide (2.95 g, 20.8 mmol) in MeOH (50 mL) was heated at 55° C. overnight. The reaction mixture was concentrated in vacuo and chromatographed on silica gel, eluting with CHCl₃:MeOH:NH₃ (aq., sat.) (6:3:1), to afford 616 mg (20%) of the sub-title compound as a brown oil.

¹H NMR (300 MHz; CD₃OD): δ 7.00–7.12 (m, 1H), 6.70–6.80 (m, 2H), 6.50–6.55 (m, 1H), 4.80 (s, 1H), 2.80 (s, 3H).

(iv) Ph(3-NMeAc)-(R) or -(S)CH(OH)C(O)OH

A mixture of Ph(3-NHMe)-(R) or -(S)CH(OH)C(O)OH (540 mg, 2.99 mmol; see step (iii) above) and acetic anhydride (612 mg, 5.98 mmol) in MeOH (15 mL) was stirred at 25° C. under nitrogen overnight. The mixture was concentrated in vacuo and chromatographed on silica gel, eluting with CHCl₃:MeOH:conc. NH₄OH (aq) (6:3:1), to afford 380 mg (57%) of the sub-title compound as a white foam.

¹H NMR (300 MHz; CD₃OD): δ 7.51–7.60 (m, 1H), 7.38–7.49 (m, 2H), 7.15–7.25 (m, 1H), 5.04 (s, 1H), 3.22 (s, 3H), 1.85 (s, 3H). ¹³C NMR (75 MHz; CD₃OD): δ 178.2, 173.6, 145.8, 142.8, 131.5, 127.8, 126.5, 126.2, 75.5, 37.8, 22.5. HPLC Analysis: 95.7%, 95.3% ee; $[\alpha]_D^{25}=-4.32°$ (c=0.5, MeOH); CI-MS: (M+1) 224 m/z.

(v) Ph(3-NMeAc)-(R) or -(S)CH(OH)C(O)-Aze-Pab(Teoc)

A mixture of Ph(3-NMeAc)-(R) or -(S)CH(OH)C(O)OH (301 mg, 1.35 mmol; see step (iv) above), H-Aze-Pab(Teoc) (560 mg, 1.48 mmol, see Example 3(vi) above), PyBOP (774 mg, 1.48 mmol), and 2,4,6-collidine (360 mg, 2.97 mmol) in DMF (10 mL) was stirred at 0° C. and then at 25° C. overnight. The mixture was quenched with H₂O (50 mL) and extracted with EtOAc (3×50 mL). The combined organic extracts were dried (Na₂SO₄), filtered and concentrated in vacuo. The residue was chromatographed on silica gel, eluting with CHCl₃:MeOH (9:1), to afford 175 mg (23%) of the sub-title compound as a white solid.

¹H NMR (CD₃OD): δ 7.82–7.90 (m, 2H), 7.20–7.50 (m, 6H), 5.32 (s, 1H), 5.25 (s, 1H), 4.70–4.81 (m, 1H), 3.97–4.54 (m, 6H), 3.20 (s, 3H), 2.10–2.82 (m, 2H), 1.85 (s, 3H), 1.02–1.18 (m, 2H), 0.10 (s, 9H). API-MS: (M+1) 582 m/z.

(vi) Ph(3-NMeAc)-(R) or -(S)CH(OH)C(O)-Aze-Pab×HOAc

A mixture of Ph(3-NMeAc)-(R,S)CH(OH)C(O)-Aze-Pab (Teoc) (65 mg, 0.11 mmol; see step (v) above) and TFA (2.0 mL) in CH₂Cl₂ (2 mL) was stirred at 0° C. for 3 hours. The solution was concentrated in vacuo at room temperature and the residue was purified using preparative HPLC (CH₃CN:0.1 M NH₄OAc, gradient: 0–50% CH₃CN) and the fractions of interest were concentrated. The product was dissolved in water/HOAc and freeze-dried to afford 55 mg (100%) of the title compound.

LC-MS: (M+1) 438; (M−1) 436 m/z; ¹H NMR (400 MHz; D₂O; mixture of rotamers): δ 7.74 (m, 3H), 7.61–7.20 (m, 5H), 5.36, 5.24 (2m, 1H), 4.84 (m, 1H), 4.58–3.94 (m, 4H), 3.42–3.08 (m, 3H), 2.80, 2.57 (2m, 1H), 2.36–1.98 (m, 4H), 1.84 (s, 3H). ¹³C NMR (100 MHz): δ 174.2, 173.1, 172.7, 166.7.

Example 8

Ph(3-NMe₂, 5-CF₃)-(R) or -(S)CH(OH)C(O)-Aze-Pab×TFA (i) Ph(3-NO₂, 5-CF₃)CH₂OH

Borane-tetrahydrofuran complex (170 mL of 1 M in THF, 170 mmol) was added, dropwise over 1 h, to a solution of Ph(3-NO₂, 5-CF₃)CO₂H (10.0 g, 42.6 mmol) in THF (50 mL) cooled to 0° C. under nitrogen. The solution was allowed to warm to room temperature and stirred for 4 h. The solution was quenched by the slow addition of H₂O, poured into EtOAc (200 mL), and then washed sequentially with H₂O (150 mL) and brine (150 mL). The organic phase was dried (Na₂SO₄), filtered, and concentrated in vacuo to afford 6.9 g (73%) of the sub-title compound as an orange oil.

¹H NMR (300 MHz; CDCl₃): δ 8.44 (s, 1H), 8.46 (s, 1H), 8.01 (s, 1H), 4.92 (d, J=5.5 Hz, 2H), 2.10 (br s, 1H).

(ii) Ph(3-NO₂, 5-CF₃)—CHO

Oxalyl chloride (3.0 mL, 34 mmol) was added dropwise to a solution of DMSO (4.86 mL, 68.6 mmol) in 70 mL of dry CH₂Cl₂ cooled to −78° C. under nitrogen. After 15 min at −78° C., Ph(3-NO₂, 5-CF₃)CH₂OH (6.9 g, 31 mmol; see step (i) above) in 75 mL of CH₂Cl₂ was added dropwise over 30 min. After 45 min at −78° C., DIPEA (27.2 mL, 156 mmol) was added over 20 minutes. The solution was stirred at −78° C. for an additional 1 h at which time, the solution was allowed to warm to room temperature and stirred for 15 h. The solution was washed sequentially with 1 M HCl (2×150 mL), brine (150 mL), dried (Na₂SO₄), filtered, and concentrated in vacuo to afford 6.9 g (99%) of the sub-title compound as an orange oil.

¹H NMR (300 MHz; CDCl₃): δ 10.19 (s, 1H), 8.94 (s, 1H), 8.76 (s, 1H), 8.51 (s, 1H).

(iii) Ph(3-NO₂, 5-CF₃)-(R,S)CH(OTMS)CN

To a solution of Ph(3-NO₂, 5-CF₃)—CHO (6.52 g, 29.7 mmol; from step (ii) above) in 220 mL of CH₂Cl₂ was added ZnI₂ (474 mg, 1.49 mmol). The solution was purged with nitrogen and cooled to 0° C. Trimethylsilyl cyanide (3.25 g, 32.7 mmol) was added over 10 min, after which the solution was stirred for 2 h. The solution was then warmed to room temperature and stirred for an additional 5.5 h, after which time the reaction was quenched with H₂O (250 mL). The organic phase was separated and the aqueous phase extracted with CH₂Cl₂ (125 mL). The combined organic layers were dried (Na₂SO₄), filtered, and concentrated in vacuo to afford 9.1 g (96%) of the sub-title compound as an orange oil.

¹H NMR (300 MHz; CDCl₃): δ 8.64 (s, 1H), 8.58 (s, 1H), 8.23 (s, 1H), 6.14 (s, 1H), 0.80 (s, 9H).

(iv) Ph(3-NO₂, 5-CF₃)-(R,S)CH(OH)C(O)OH

Ph(3-NO₂, 5-CF₃)-(R,S)CH(OTMS)CN (9.1 g, 29 mmol; see step (iii) above) was dissolved in concentrated HCl (83 mL, 1000 mmol) and heated to reflux for 3 h. The solution was diluted with H₂O (200 mL) and extracted with Et₂O (3×150 mL). The combined organics were washed with brine (200 mL), dried (Na₂SO₄), filtered, and concentrated in vacuo to afford a brown oil. The crude product was flash chromatographed on silica gel, eluting with CHCl₃:MeOH:NH₃ (aq., sat.) (14:5:1). The resulting white solid was suspended in Et₂O and 2 M HCl (100 mL) was added. The layers were separated and the aqueous phase was extracted with Et2O (3×200 mL). The combined organic layers were dried (Na₂SO₄), filtered, and concentrated to afford 5.9 g (78%) of the sub-title compound as a brown solid.

¹H NMR (300 MHz; CD₃OD): δ 8.65 (s, 1H), 8.47 (s, 1H), 8.23 (s, 1H), 5.43 (s, 1H).

(v) Ph(3-NH₂, 5-CF₃)-(R,S)CH(OH)C(O)OH

To a solution of Ph(3-NO₂, 5-CF₃)-(R,S)CH(OH)C(O)OH (5.9 g, 22 mmol; see step (iv) above) in absolute EtOH (350 mL) was added platinum(IV) oxide (590 mg). The solution was purged with hydrogen for 5 h, after which time the mixture was filtered through Celite® and then concentrated in vacuo to afford 5.8 g (100%) of the sub-title compound as an orange oil.

$^1$H NMR (300 MHz; CD$_3$OD): δ 7.00 (s, 2H), 6.86 (s, 1H), 5.06 (s, 1H).

(vi) Ph(3-NMe$_2$, 5-CF$_3$)-(R,S)CH(OH)C(O)OH

To a solution of Ph(3-NH$_2$, 5-CF$_3$)-(R,S)CH(OH)C(O)OH (5.27 g, 22.4 mmol; see (v) above) dissolved in absolute EtOH (250 mL) was added a 37% aqueous solution of formaldehyde (54 mL, 720 mmol). Platinum(IV) oxide (520 mg) was added, and the solution purged with hydrogen. After stirring under hydrogen for 22 h, the solution was filtered through Celite® and concentrated in vacuo. Flash chromatography on silica gel, eluting with CHCl$_3$:MeOH:NH$_3$ (aq., sat.) (6:3:1), afforded 2.7 g (46%) of the sub-title compound as a white solid.

$^1$H NMR (300 MHz; CD$_3$OD): δ 7.10 (s, 1H), 7.07 (s, 1H), 6.80 (s, 1H), 4.88 (s, 1H), 2.98 (s, 6H).

(vii) Ph(3-NMe$_2$, 5-CF$_3$)-(R) or -(S)CH(OH)C(O)OH (a) and Ph(3-NMe$_2$)(5-CF$_3$)-(S) or -(R)CH(OAc)C(O)OH (b)

A mixture of Ph(3-NMe$_2$, 5-CF$_3$)-(R,S)CH(OH)C(O)OH (2.7 g, 10 mmol; see step (vi) above), Lipase PS Amano (1.4 g), vinyl acetate (56 mL) and MTBE (120 mL) was refluxed for 1 day. The reaction was filtered through Celite® and the filter cake washed with Et$_2$O. The filtrate was concentrated in vacuo and subjected to flash chromatography on silica gel, eluting with CHCl$_3$:MeOH:NH$_3$ (aq., sat.) (14:5:1), to afford 727 mg (27%) of the ammonium salt of the sub-title compound (a) as a white solid and 1.53 g (49%) of the ammonium salt of the sub-title compound (b) as a white solid. The ammonium salt of the sub-title compound (a) was flushed through a pad of Amberlite® CG-50 with CH$_3$CN:MeOH (3:1) as eluent to afford the sub-title compound (a) as a white solid.

For sub-title compound (a): $^1$H NMR (300 MHz; CD$_3$OD): δ 7.03–7.09 (m, 2H), 6.79 (s, 1H), 4.95 (s, 1H), 2.88 (s, 6H). $^{13}$C NMR (75 MHz; CD$_3$OD): δ 180.2, 152.9, 146.0, 133.0 (q, J=32.2 Hz), 125.2 (t, J=284.0 Hz), 116.3, 113.4, 109.3, 77.4, 41.4. HPLC Analysis: 98.8%, >99% ee; $[α]_D^{25}$=−59.5° (c=1.0, MeOH); API-MS: (M+1) 264 m/z;

For sub-title compound (b): $^1$H NMR (300 MHz; CD$_3$OD): δ 7.12 (s, 1H), 7.09 (s, 1H), 6.83 (s, 1H), 5.73 (s, 1H), 3.00 (s, 6H), 2.14 (s, 3H).

(viii) Ph(3-NMe$_2$, 5-CF$_3$)-(R) or -(S)CH(OH)C(O)-Aze-Pab (Teoc)

To a mixture of Ph(3-NMe$_2$, 5-CF$_3$)-(R) or -(S)CH(OH)C(O)OH (290 mg, 1.10 mmol; see step (vii)(a) above) and H-Aze-Pab(Teoc) (436 mg, 1.16 mmol, see Example 3(vi)) was added 10 mL of dry DMF. The solution was cooled to 0° C., after which PyBOP (630 mg, 1.21 mmol) and collidine (295 mg, 2.42 mmol) were added. The solution was stirred under nitrogen at 0° C. for 2 h and at room temperature for 15 h. The mixture was concentrated and subjected to flash chromatography on silica gel, eluting with EtOAc:EtOH (20:1), to afford 383 mg (56%) of the sub-title compound as a white solid.

$^1$H NMR (300 MHz; CD$_3$OD): δ 7.76–7.83 (d, J=8.0 Hz, 2H), 7.38–7.44 (d, J=8.0 Hz, 2H), 7.12 (m, 2H), 6.86–6.87 (m, 1H), 5.15–5.17 (m, 1H), 4.75–4.81 (m, 1H), 3.98–4.56 (m, 6H), 3.00 (s, 6H), 2.48–2.58 (m, 1H), 2.24–2.33 (m, 1H), 1.03–1.13 (m, 2H), 0.08 (s, 9H). API-MS: (M+1) 622 m/z.

(ix) Ph(3-NMe$_2$, 5-CF$_3$)-(R) or -(S)CH(OH)C(O)-Aze-Pab×TFA

To an ice-cold solution of Ph(3-NMe$_2$, 5-CF$_3$)-(R) or -(S)CH(OH)C(O)-Aze-Pab(Teoc) (87 mg, 0.14 mmol; see step (viii) above) in methylene chloride was added TFA (4 mL), and the mixture was stirred at 0° C. for 100 min. The resultant solution was concentrated to dryness, giving a residue that was dissolved in water/CH$_3$CN and then freeze-dried, yielding 81 mg (80%) of the title compound as a white powder.

LC-MS: (M+1) 478; (M−1) 476 m/z; $^1$H NMR (400 MHz; CD$_3$OD; mixture of rotamers): δ 7.78–7.50 (m, 4H), 7.09–7.04 (m, 2H), 6.92 (br s, 1H), 5.21, 5.17 (2s, 1H), 4.80 (m, 1H), 4.52 (AB part of an ABX spectrum; 2H), 4.41–3.95 (m, 2H), 3.00 (s, 3H), 2.70, 2.52 (2m, 1H), 2.30, 2.15 (2m, 1H). $^{13}$C NMR (carbonyl and/or amidine carbons; 100 MHz): δ 172.6, 171.7, 167.0, 161.5, 161.2.

Example 9

Ph(3-Cl,5-(1-Pyrrolidin-2-one))-(R) or -(S)CH(OH)C(O)-Aze-Pab×HOAc (i) (R,S)-5-Ph(3-Cl,5-NO)-2,2-Dimethyl-4-oxo-1,3-dioxolane To a solution of Ph(3-Cl,5-NO$_2$)-(R,S)CH(OH)C(O)OH (18.8 g, 81.2 mmol; see Example 5(ii) above) in acetone (300 mL) was added p-toluenesulfonic acid monohydrate (750 mg, 3.94 mmol) and 2,2-dimethoxypropane (75 mL, 514 mmol). The solution was refluxed for 6 h and concentrated in vacuo. The residue was dissolved in EtOAc (200 mL), and then washed with H$_2$O (100 mL), saturated NaHCO$_3$ (150 mL) and brine (150 mL). The organic phase was dried (Na$_2$SO$_4$), filtered, and concentrated to afford a brown solid which was flash chromatographed on silica gel, eluting with Hex:EtOAc (7:3). The resulting solid was further purified by recrystallization from EtOAc/Hex (1:10) to afford 14.7 g (67%) of the sub-title compound as a white solid.

$^1$H NMR (300 MHz; CDCl$_3$): δ 8.29 (m, 1H), 8.24 (m, 1H), 7.86 (m, 1H), 5.45 (s, 1H), 1.78 (s, 3H), 1.72 (s, 3H).

(ii) (R,S)-5-Ph(3-Cl,5-NH$_2$)-2,2-Dimethyl-4-oxo-1,3-dioxolane

To a solution of (R,S)-5-Ph(3-Cl,5-NO$_2$)-2,2-dimethyl-4-oxo-1,3-dioxolane (14.7 g, 54.1 mmol; see step (i) above) in EtOH (400 mL) was added platinum(IV) oxide (1.5 g). The suspension was stirred under one atmosphere of hydrogen for 27 h at room temperature. The suspension was filtered through Celite® and the filter cake washed with EtOH. The filtrate was concentrated in vacuo to afford a yellow oil which was flash chromatographed on silica gel eluting with Hex:EtOAc (4:1) to afford 6.5 g (50%) of the sub-title compound as a yellow oil.

$^1$H NMR (300 MHz; CDCl$_3$): δ 6.76 (m, 1H), 6.56 (m, 2H), 5.18 (s, 1H), 3.74 (br s, 2H), 1.64 (s, 3H), 1.68 (s, 3H).

(iii) (R,S)-5-Ph(3-Cl,5-(1-Pyrrolidinyl-2-one))-2,2-dimethyl-4-oxo-1,3-dioxolane To a solution of (R,S)-5-Ph(3-Cl,5-NH$_2$)-2,2-dimethyl-4-oxo-1,3-dioxolane (6.5 g, 26.9 mmol; see step (ii) above) in DMF (100 mL) was added ethyl 4-bromobutyrate (10.5 g, 53.8 mmol) and Et$_3$N (5.4 g, 53.8 mmol). The solution was heated at 95° C. under argon for 21 h. The reaction mixture was concentrated and then dissolved in EtOAc (200 mL), giving a solution that was washed with H$_2$O (150 mL) and brine (150 mL). The organic phase was dried (Na$_2$SO$_4$), filtered, and concentrated to afford 9.6 g of an orange oil. The crude material was dissolved in p-xylene (250 mL) and heated at reflux. After 3 days, the mixture was concentrated to an orange oil and flash chromatographed on silica gel, eluting with EtOAc:Hexane (1:1), to afford 4.5 g (54%) of the sub-title compound as a yellow solid.

$^1$H NMR (300 MHz; CDCl$_3$): δ 7.74 (m, 1H), 7.69 (m, 1H), 7.26 (m, 1H), 5.38 (s, 1H), 3.80–3.93 (m, 2H), 2.60–2.68 (t, J=7.5 Hz, 2H), 2.15–2.25 (m, 2H), 1.77 (s, 3H), 1.70 (s, 3H).

(iv) Ph(3-Cl,5-(1-Pyrrolidin-2-one))-(R,S)CH(OH)C(O)OH

To a solution of (R,S)-5-Ph(3-Cl,5-(1-pyrrolidinyl-2-one))-2,2-dimethyl4-oxo-1,3-dioxolane (4.5 g, 14.5 mmol; see step (iii) above) in THF (300 mL) was added 1 N NaOH (145 mL). The solution was stirred for 30 min., whereafter the resultant solution was partly reduced in vacuo. The solution was acidified with 2 N HCl and extracted with EtOAc (2×150 mL). The organic phase was washed with brine (200 mL), dried (Na$_2$SO$_4$), filtered, and concentrated to give 3.2 g (82%) of the sub-title compound as a white solid.

$^1$H NMR (300 MHz; CD$_3$OD): δ 7.81 (m, 1H), 7.59 (m, 1H), 7.30 (m, 1H), 5.15 (s, 1H), 3.89–3.96 (t, J=7.5 Hz, 2H), 2.57–2.65 (t, J=7.5 Hz, 2H), 2.12–2.22 (m, 2H).

(v) Ph(3-Cl,5-(1-Pyrrolidin-2-one))-(S) or -(R)—CH(OAc)C(O)OH (b) and Ph(3-Cl,5-(1-Pyrrolidin-2-one))-(R) or -(S)—CH(OH)C(O)OH (a)

A mixture of Ph(3-Cl,5-(1-pyrrolidin-2-one))-(R,S)CH(OH)C(O)OH (3.2 g, 11.9 mmol; see step (iv) above) and Lipase PS Amano (1.6 g) in vinyl acetate (65 mL) and MTBE (130 mL) was stirred at 55° C. for 24 h. The reaction was filtered through Celite® and the filter cake washed sequentially with THF and then MeOH. The filtrate was concentrated in vacuo and flash chromatographed on silica gel, eluting with CHCl$_3$:MeOH:NH$_3$ (aq., sat.) (14:5:1), to afford 1.3 g (33%) of the ammonium salt of the sub-title compound (b) as a white solid. In addition, 800 mg (20%) of the ammonium salt of the sub-title compound (a) was obtained. This material was dissolved in H$_2$O (40 mL), acidified with 1 N HCl, and extracted with EtOAc (2×50 mL). The organic phase was dried (Na$_2$SO$_4$), filtered, and concentrated to afford the sub-title compound (a) as a white solid. Due to low optical purity, the sub-title compound (b) was resubmitted to the above enzymatic resolution conditions (0.5 g Lipase PS Amano; 35 mL vinyl acetate; 60 mL MTBE; 55° C.; 24 h). Isolation and purification as reported above afforded 470 mg of the sub-title compound (a) as a white solid.

For sub-title compound (a): $^1$H NMR (300 MHz; CD$_3$OD): δ 7.80 (m, 1H), 7.59 (m, 1H), 7.29 (m, 1H), 5.15 (s, 1H), 3.88–3.92 (t, J=7.1 Hz, 2H), 2.57–2.62 (t, J=8.1 Hz, 2H), 2.11–2.21 (m, 2H). $^{13}$C NMR (75 MHz; CD$_3$OD): δ 179.7, 177.8, 146.1, 144.4, 137.9, 126.3, 123.5, 120.2, 75.9, 52.7, 36.0, 21.2. API-MS: (M+1) 270 m/z; HPLC Analysis: 95.3%, 96.5% ee; $[α]_D^{25}$=−64.50 (c=1.0, MeOH).

(vi) Ph(3-Cl,5-(1-Pyrrolidin-2-one))-(R)- or (S)—CH(OH)C(O)-Aze-Pab(Teoc)

To a mixture of Ph(3-Cl,5-(1-pyrrolidin-2-one))-(R)- or -(S)—CH(OH)C(O)OH (250 mg, 0.927 mmol; from step (v)(a) above) and H-Aze-Pab(Teoc) (367 mg, 0.973 mmol, see Example 3(vi)) in DMF (9 mL) at 0° C. was added PyBop (531 mg, 1.02 mmol) and collidine (250 mg, 2.04 mmol). The solution was stirred under nitrogen at 0° C. for 2 h and then warmed to room temperature for 15 h. The mixture was concentrated and subjected to flash chromatography on silica gel, eluting with EtOAc:EtOH (20:1), followed by an EtOH column flush to afford a white solid. Further flash chromatography on silica gel, eluting with CHCl$_3$:EtOH (9:1), afforded 420 mg (72%) of the sub-title compound as a white solid.

$^1$H NMR (300 MHz; CD$_3$OD): δ 7.73–7.85 (m, 3H), 7.51–7.65 (m, 1H), 7.36–7.47 (m, 2H), 7.22–7.31 (m, 1H), 5.11–5.23 (m, 1H), 4.76–4.86 (m, 1H), 3.95–4.55 (m, 6H), 3.84–3.94 (t, J=7.5 Hz, 2H), 2.46–2.74 (m, 3H), 2.08–2.47 (m, 3H), 1.02–1.14 (m, 2H), 0.09 (s, 9H). API-MS: (M+1) 629 m/z.

(vii) Ph(3-Cl,5-(1-Pyrrolidin-2-one))-(R) or -(S)CH(OH)C(O)-Aze-Pab×HOAc

To a solution of Ph(3-Cl,5-(1-pyrrolidin-2-one))-(R or S)CH(OH)C(O)-Aze-Pab(Teoc) (90 mg, 0.14 mmol; see step (vi) above) in methylene chloride (0.5 mL) was added TFA (4 mL). The mixture was stirred at RT for 100 min. The resultant solution was concentrated in vacuo, and the solid crude material was purified using PHPLC (CH$_3$CN:0.1M ammonium acetate 20:80). The fractions of interest were pooled and freeze dried twice overnight. Yield 51 mg (67%). Purity 99.8%.

LC-MS (M+1)=484, 486 m/z; $^1$H NMR (400 MHz, CD$_3$OD): δ 7.73 (m, 3H), 7.62 (m, 1H), 7.52 (m, 2H), 7.28, 7.23 (2s, 1H), 5.19 (s, 1H), 4.80 (dd, 1H), 4.51 (AB part of an ABX spectrum, 2H), 4.38 (m, 1H), 4.19 (m, 1H), 4.02 (m, 1H), 3.88 (t, 2H), 2.61–2.48 (m, 3H), 2.29 (m, 1H), 2.14 (m, 2H), 1.90 (s, 3H). $^{13}$C NMR (100 MHz) (carbonyl and/or amidine carbons): δ 176.0, 172.3, 171.7, 167.0.

Example 10

Ph(3-(1-Pyrrolidin-2-one))-(R) or -(S)CH(OH)C(O)-Aze-Pab×HOAc (i) (R,S)-5-Ph(3-NO$_2$)-2,2-Dimethyl-4-oxo-1,3-dioxolane A mixture of m-nitromandelic acid (6.0 g, 30.4 mmol), 2,2-dimethoxy propane (15.1 mL), p-toluenesulfonic acid monohydrate (0.29 g, 1.52 mmol) and acetone (60 mL) was stirred for 12 hours at room temperature. The mixture was concentrated in vacuo and the crude product was dissolved in EtOAc. The organic phase was washed sequentially with saturated aqueous NaHCO$_3$ and brine, dried (MgSO$_4$) and then concentrated in vacuo. The residue was chromatographed on silica gel, eluting with heptane/EtOAc (80/20 to 70/30), to afford 5.7 g (79%) of the sub-title compound. (The crude product was difficult to dissolve in a small amount of EtOAc, and so loading onto the chromatography column was achieved by using silica gel onto which the product had been adsorbed.)

FAB-MS: (M+1) 238 m/z; $^1$H NMR (400 MHz; CDCl$_3$): δ 8.36 (br s, 1H), 8.22 (dd, 1H), 7.84 (dd, 1H), 7.60 (dd, 1H), 5.44 (s, 1H), 1.76 (s, 3H), 1.71 (s, 3H).

(ii) (R,S)-5-Ph(3-NH$_2$)-2,2-Dimethyl-4-oxo-1,3-dioxolane

A mixture of (R,S)-5-Ph(3-NO$_2$)-2,2-dimethyl-4-oxo-1,3-dioxolane (3.1 g, 13.1 mmol; see step (i) above), Pd/C, 5% (1.7 g) and HOAc (0.75 mL, 13.1 mmol) in EtOH (250 mL) was stirred under a hydrogen atmosphere for 4 h. The mixture was filtered through a pad of Celite®, and the filter cake was washed with EtOH. The filtrate was concentrated in vacuo and the colourless solid formed was partitioned between EtOAc and saturated aqueous NaHCO$_3$. The water phase was extracted with EtOAc and the combined organic phases were washed with brine, dried (Na$_2$SO$_4$) and concentrated in vacuo to afford 2.3 g (85%) of the sub-title compound.

LC-MS: (M+1) 208 m/z; $^1$H NMR (400 MHz; CDCl$_3$): δ 7.16 (dd, 1H), 6.84 (dd, 1H), 6.76 (br s, 1H), 6.67 (dd, 1H), 5.30 (s, 1H), 1.70 (s, 3H), 1.65 (s, 3H).

(iii) (R,S)-5-Ph(3-NH(CH$_2$)$_3$C(O)OEt)-2,2-Dimethyl-4-oxo-1,3-dioxolane

A mixture of (R,S)-5-Ph(3-NH$_2$)-2,2-dimethyl-4-oxo-1,3-dioxolane (1.63 g, 7.87 mmol; see step (ii) above), ethyl 4-bromobutyrate (3.4 mL, 23.6 mmol) and Et$_3$N (3.3 mL, 23.6 mmol) in CH$_2$Cl$_2$ was refluxed overnight. Additional amounts of ethyl 4-bromobutyrate (2.3 mL, 15.7 mmol) and Et$_3$N (2.2 mL, 15.7 mmol) were added and the mixture was refluxed for one more night. The solvent was removed and the crude product was partitioned between EtOAc and water. The water phase was extracted with EtOAc and the combined organic phases were washed with brine, dried (Na$_2$SO$_4$) and then concentrated in vacuo. The residue was chromatographed on silica gel, eluting with heptane:EtOAc (90:10 to 80:20), to afford 2.1 g (84%) of the sub-title compound.

FAB-MS: (M+1) 322 m/z; $^1$H NMR (400 MHz; CDCl$_3$): δ 7.17 (dd, 1H), 6.77 (br d, 1H), 6.66 (br s, 1H), 6.59 (dd, 1H), 5.30 (s, 1H), 4.12 (q, 2H), 3.16 (t, 2H), 2.40 (t, 2H), 1.93 (m, 2H), 1.70 (s, 3H), 1.64 (s, 3H), 1.24 (t, 2H).

(iv) (R,S)-5-Ph(3-(1-Pyrrolidin-2-one))-2,2-dimethyl-4-oxo-1,3-dioxolane

A solution of (R,S)-5-Ph(3-NH(CH$_2$)$_3$C(O)OEt)-2,2-dimethyl-4-oxo-1,3-dioxolane (2.2 g, 6.85 mmol; see step (iii) above) in toluene (15 mL) was refluxed for two nights. The solvent was removed and the crude product was submitted to flash chromatography, eluting with heptane:EtOAc (80:20 to 60:40), to afford 1.4 g (74%) of the sub-title compound.

$^1$H NMR (400 MHz; CDCl$_3$): δ 7.78 (br s, 1H), 7.60 (br d, 1H), 7.38 (dd, 1H), 7.23 (br d, 1H), 5.40 (s, 1H), 3.85 (m, 2H), 2.59 (t, 2H), 2.14 (m, 2H), 1.70 (s, 3H), 1.65 (s, 3H).

(v) Ph(3-(1-Pyrrolidin-2-one))-(R,S)CH(OH)C(O)OH

A mixture of (R,S)-5-Ph(3-(1-pyrrolidin-2-one))-2,2-dimethyl-4-oxo-1,3-dioxolane (1.4 g, 5.1 mmol; see step (iv) above) and 1 M NaOH (10 mL) in THF (15 mL) was vigorously stirred overnight at room temperature. THF was removed and the water phase was washed once with CH$_2$Cl$_2$ and thereafter concentrated in vacuo. The residue was purified using preparative RPLC (CH$_3$CN:0.1 M HOAc (16:84)) and the fractions of interest were concentrated and freeze-dried to afford 0.94 g (79%) of the sub-title compound.

LC-MS: (M+1) 236; (M−1) 234 m/z; $^1$H NMR (400 MHz; CD$_3$OD): δ 7.64 (br s, 1H), 7.59 (br d, 1H), 7.35 (dd, 1H), 7.28 (br d, 1H), 5.10 (s, 1H), 3.92 (t, 2H), 2.58 (t, 2H), 2.16 (m, 2H).

(vi) Ph(3-(1-Pyrrolidin-2-one))-(R) or -(S)CH(OH)C(O)OH

The enantiomers of Ph(3-(1-pyrrolidin-2-one))-(R,S)CH(OH)C(O)OH (0.94 g, 4.0 mmol; see step (v) above) were separated by preparative HPLC using Chiralpak™ AD as stationary phase and heptane:2-propanol:acetonitrile:formic acid (160:30:10:1) as mobile phase. The enantiomer which eluted first was evaporated in vacuo to afford 0.37 g (39%) of the sub-title compound which gave 98.6% ee and $[\alpha]_D^{20}$=−90.9° (c=1.0, MeOH).

(vii) Ph(3-(1-Pyrrolidin-2-one))-(R) or -(S)CH(OH)C(O)-Aze-Pab(Teoc)

PyBop (365 mg, 0.70 mmol), followed by DIPEA (0.5 mL, 2.8 mmol) were added to a cooled (−20° C.) solution of Ph(3-(1-pyrrolidin-2-one))-(R) or -(S)CH(OH)C(O)OH (150 mg, 0.64 mmol; see step (vi) above) and H-Aze-Pab (Teoc) (264 mg, 0.70 mmol, see Example 3(vi) above) in DMF (8 mL). The mixture was slowly allowed to reach room temperature and stirred overnight. DMF was removed in vacuo and the residue was chromatographed on silica gel, eluting with CH$_2$Cl$_2$:MeOH (95:5), to afford 310 mg (82%) of the sub-title compound.

LC-MS: (M+1) 594; (M−1) 592 m/z; $^1$H NMR (400 MHz; CDCl$_3$; mixture of rotamers): δ 8.09 (br dd, 1H), 7.66 (br d, 2H), 7.47 (br d, 1H), 7.34 (dd, 1H), 7.25 (br d, 2H), 7.12 (d, 1H), 5.02 (s, 1H), 4.83 (dd, 1H), 4.43 (d, 2H), 4.25 (t, 2H), 4.17 (m, 1H), 3.82 (m, 3H), 3.65 (m, 1H), 3.10 (m, 1H), 2.55 (dd, 2H), 2.50 (m, 1H), 2.38 (m, 1H), 2.13 (m, 2H), 1.10 (t, 2H), 0.05 (s, 9H).

(viii) Ph(3-(1-Pyrrolidin-2-one))-(R) or -(S)CH(OH)C(O)-Aze-Pab×HOAc

A mixture of Ph(3-(1-pyrrolidin-2-one))-(R) or -(S)CH(OH)C(O)-Aze-Pab(Teoc) (70 mg, 0.12 mmol; see step (vii) above) and TFA (2.0 mL) in CH$_2$Cl$_2$ (2 mL) was stirred at 0° C. for 2 hours. The solution was concentrated in vacuo and the residue was purified using preparative HPLC (CH$_3$CN:0.1 M NH$_4$OAc (gradient: 0–50% CH$_3$CN)). The fractions of interest were concentrated and the resulting product was dissolved in water/HOAc and freeze-dried to afford 52 mg (87%) of the title compound.

LC-MS: (M+1) 450 m/z; $^1$H NMR (400 MHz; CD$_3$OD; mixture of rotamers): δ 7.72 (m, 3H), 7.52 (m, 3H), 7.42–7.20 (m, 2H), 5.22–5.12 (m, 1H), 4.80 (m, 1H), 4.50 (AB part of an ABX spectrum, 2H), 4.14 (m, 1H), 4.07 (m, 1H), 3.90 (m, 2H), 2.74–2.44 (m, 3H), 2.34–2.08 (m, 3H), 1.90 (s, 3H). $^{13}$C NMR (carbonyl and/or amidine carbons; 100 MHz): δ 176.0, 172.4, 171.8, 167.0.

Example 11

Ph(3-(1-Pyrrolidine))-(R)- or -(S)—CH(OH)C(O)-Aze-Pab×2TFA (i) (R,S)-5-Ph(3-(1-Pyrrolidine))-2,2-dimethyl-4-oxo-1,3-dioxolane A A mixture of (R,S)-5-Ph(3-NH$_2$)-2,2-dimethyl-4-oxo-1,3-dioxolane (450 mg, 2.17 mmol; see Example 10(ii) above), 1,4-dibromo-butane (0.30 mL, 3.26 mmol) and Cs$_2$CO$_3$ (2.1 g, 6.5 mmol) in acetone was refluxed for 3 days. The solvent was removed and the crude product was partitioned between CH$_2$Cl$_2$ and water. The water phase was extracted with CH$_2$Cl$_2$ and the combined organic phases were washed with brine, dried (Na$_2$SO$_4$) and then concentrated in vacuo. The residue was chromatographed on silica gel, eluting with heptane:EtOAc (100:0 to 90:10), to afford 140 mg (25%) of the sub-title compound.

LC-MS: (M+1) 413; (M−1) 411 m/z; $^1$H NMR (400 MHz; CDCl$_3$): δ 7.23 (dd, 1H), 6.74 (d, 1H), 6.61 (br s, 1H), 6.55 (br d, 1H), 5.35 (s, 1H), 3.29 (m, 4H), 2.00 (m, 4H), 1.72 (s, 3H), 1.66 (s, 3H).

(ii) Ph(3-(1-Pyrrolidine))-(R,S)CH(OH)C(O)OH×HCl

A mixture of (R,S)-5-Ph(3-(1-pyrrolidine))-2,2-dimethyl-4-oxo-1,3-dioxolane (640 mg, 2.45 mmol; see step (i) above) and 1 M NaOH (10 mL) in THF (10 mL) was stirred vigorously overnight at room temperature. THF was removed and the water phase was washed once with CH$_2$Cl$_2$ and thereafter concentrated in vacuo. The residue was chromatographed on silica gel, eluting with CH$_2$Cl$_2$:MeOH:NH$_2$OH (6:3:1). The product was freeze-dried twice to change salts, first using water/HOAc and secondly using water/2 M HCl. This yielded 0.62 g (98%) of the sub-tide compound.

LC-MS: (M+1) 222; (M−1) 220 m/z; $^1$H NMR (400 MHz; CD$_3$OD): δ 7.40 (m, 1H), 7.20–7.55 (m, 3H), 5.28 (s, 1H), 3.80 (m, 4H), 2.30 (m, 4H).

(iii) Ph(3-(1-Pyrrolidine))-(R,S)CH(OH)C(O)-Aze-Pab (Teoc)

PyBop (355 mg, 0.68 mmol) and then collidine (0.4 mL, 3.35 mmol), were added to a cooled (−20° C.) solution of Ph(3-(1-pyrrolidine))-(R,S)CH(OH)C(O)OH) (160 mg, 0.62 mmol; see step (ii) above) and H-Aze-Pab(Teoc)×2 HCl (307 mg, 0.68 mmol, see Example 3(vi) above) in DMF (8 mL). The reaction was allowed to slowly reach room temperature and stirred overnight. DMF was removed and the crude product was partitioned between EtOAc and water. The water phase was extracted with EtOAc and the organic phase was dried (Na$_2$SO$_4$) and concentrated in vacuo. The residue was chromatographed on silica gel, eluting with CH$_2$Cl$_2$:MeOH (95:5) to afford 50 mg (14%) of the sub-title compound.

LC-MS: (M+1) 580; (M−1) 578 m/z; $^1$H NMR (400 MHz; CDCl$_3$; mixture of rotamers): δ 7.82 (m, 2H), 7.46–7.30 (m, 2H), 7.18–7.08 (m, 1H), 6.70–6.45 (m, 3H), 5.12–5.00 (m, 1H), 4.75 (m, 1H), 4.45 (m, 2H), 4.23 (m, 2H), 4.1–3.85 (m, 2H), 3.22 (m, 4H), 2.69–2.34 (m, 1H), 2.25, 2.11 (2m, 1H), 1.07 (m, 2H), 0.08 (s, 9H).

(iv) Ph(3-(1-Pyrrolidine))-(R,S)CH(OH)C(O)-Aze-Pab×2TFA

A mixture of Ph(3-(1-pyrrolidine))-(R,S)CH(OH)C(O)-Aze-Pab(Teoc) (100 mg, 0.17 mmol; see step (iii) above) and TFA (2.0 mL) in $CH_2Cl_2$ (2 mL) was stirred at 0° C. for 2 hours. The solution was concentrated in vacuo to give a residue that was dissolved in water and freeze-dried to afford 70 mg (58%) of the title compound.

LC-MS: (M+1) 580 m/z; $^1$H NMR (400 MHz; $CD_3OD$; mixture of rotamers): δ 7.75 (m, 2H), 7.50 (m, 2H), 7.15 (m, 1H), 6.75–6.50 (m, 3H), 5.14, 5.08 (2s, 1H), 4.76 (m, 1H), 4.60–4.42 (m, 2H), 4.28 (m, 1H), 4.11–3.87 (m, 2H), 3.26 (m, 4H), 2.75–2.40 (m, 1H), 2.26, 2.13 (2m, 1H), 1.89 (m, 4H). $^{13}$C NMR (carbonyl and/or amidine carbons; 100 MHz): δ 173.8, 173.3, 171.8, 167.0.

Example 12

Ph(3-Cl,5-NMe$_2$)-(R) or -(S)CH(OH)C(O)-Aze-Pab (OMe)

(i) Ph(3-Cl,5-NMe$_2$)-(R) or -(S)CH(OH)C(O)-Aze-Pab (Teoc)(OMe)

To a solution of Ph(3-Cl,5-NMe$_2$)-(R) or -(S)CH(OH)C(O)-Aze-Pab(Teoc) (92 mg, 0.16 mmol; see Example 6(vi) above) in THF (6 mL) was added O-methylhydroxylamine (78 mg, 0.92 mmol), to give a mixture that was stirred overnight at 60° C. The solvent was removed in vacuo, and the resulting solid was chromatographed on silica gel, eluting with EtOAc. The fractions of interest were concentrated, yielding the sub-title compound (82 mg, 85%) as a white solid.

$^1$H NMR (400 MHz; CDCl$_3$): δ 8.0 (bt, 1H), 7.57 (b, 1H), 7.50 (d, 2H), 7.33 (d, 2H), 6.64 (m, 2H), 6.51 (s, 1H), 4.90 (dd, 1H), 4.82 (s, 1H), 4.51 (AB part of ABX spectrum, 2H), 4.16 (m, 2H), 4.07 (m, 1H), 3.97 (s, 3H), 3.65 (m, 1H), 2.97 (s, 6H), 2.70 (m, 1H), 2.40 (m, 1H), 0.99 (m, 2H), 0.03 (s, 12H).

LC-MS: (M+1) 618 m/z.

(ii) Ph(3-Cl,5-NMe$_2$)-(R) or -(S)CH(OH)C(O)-Aze-Pab (OMe)

A solution of Ph(3-Cl,5-NMe$_2$)-(R) or -(S)CH(OH)C(O)-Aze-Pab(Teoc)(OMe) (78 mg, 0.13 mmol, see step (i) above) in TFA (3 mL) was stirred at 0° C. for 2 h. The solution was concentrated cold in vacuo and the resulting solid was chromatographed on preparative HPLC (CH$_3$CN:0.1 M ammonium acetate (40:60)). The fractions of interest were partially concentrated. The residue was freeze-dried (CH$_3$CN:water) 3 times, yielding 40 mg (30%) of the title compound. Purity 99.4%

$^1$H NMR (400 MHz; CDCl$_3$): δ 7.59 (d, 2H), 7.32 (d, 2H), 6.72 (s, 2H), 6.66 (m, 1H), 5.05 (s, 1H), 4.84 (s, 4H), 4.76 (dd, 1H), 4.44 (AB part of an ABX spectrum, 2H), 4.30 (m, 1H), 4.00 (m, 1H), 3.82 (s, 3H), 2.93 (s, 6H), 2.49 (m, 1H), 2.39 (m, 1H). $^{13}$C NMR (carbonyl and/or amidine carbons; 100 MHz): δ 172.7, 171.8, 171.7, 158.7.

LC-MS: (M+1) 474 m/z.

Example 13

Ph(3-Cl,5-NMe$_2$)-(R) or -(S)CH(OH)C(O)-Aze-Pab (O-Et)

(i) Ph(3-Cl,5-NMe,)-(R) or -(S)CH(OH)C(O)-Aze-Pab (Teoc)(O-Et)

To a solution of Ph(3-Cl,5-NMe$_2$)-(R) or -(S)CH(OH)C(O)-Aze-Pab(Teoc) (40 mg, 0.07 mmol, see Example 6(vi) above) in THF (3 mL) was added O-ethylhydroxylamine× HCl (40 mg, 0.41 mmol), and the solution was stirred at 60° C. overnight. The solution was concentrated, and the resultant material was purified with preparative HPLC (CH$_3$CN:0.1 M ammonium acetate (60:40)). The fractions of interest were partly concentrated, and the residual was extracted with EtOAc (3×). The organic layer was washed with water and concentrated in vacuo yielding 16 mg (37%) of the sub-title compound $^1$H NMR (400 MHz; CDCl$_3$): δ 8.00 (b, 1H), 7.58 (b, 1H), 7.49 (d, 2H), 7.32 (d, 2H), 6.65 (s, 1H), 6.63 (s, 1H), 6.51 (s, 1H), 4.90 (dd, 1H), 4.82 (s, 1H), 4.50 (AB part of an ABX spectrum, 2H), 4.25 4.15 (m, 5H), 4.06 (m, 1H), 3.65 (q, 1H), 2.97 (s, 6H), 2.69 (m, 1H), 2.39 (m, 1H), 1.34 (t, 3H), 0.99 (t, 2H), 0.05 (s, 9H).

LC-MS: (M+1) 633 m/z.

(ii) Ph(3-Cl,5-NMe$_2$)-(R) or -(S)CH(OH)C(O)-Aze-Pab(O-Et)

To a solution of Ph(3-Cl,5-NMe$_2$)-(R) or -(S)CH(OH)C(O)-Aze-Pab(Teoc)(O-Et) (16 mg, 0.03 mmol, see step (i) above) in methylene chloride (0.5 mL) was added TFA (1 mL), and the mixture was stirred at 0° C. for 2 h. The resulting mixture was concentrated in vacuo to give a solid residue that was dissolved in water/CH$_3$CN and freeze-dried twice yielding 14 mg (92%) of the title compound. Purity 94.4%.

$^1$H NMR (400 MHz; CD$_3$OD): δ 8.73 (bt, 1H), 7.66 (d, 2H), 7.53 (d, 2H), 6.73 (s, 2H), 6.67 (s, 2H), 5.07 (s, 2H), 4.78 (dd, 1H), 4.51 (AB part of an ABX spectrum, 2H), 4.32 (m, 1H), 4.16 (m, 1H), 4.04 (m, 1H), 2.94 (s, 6H), 2.50 (m, 1H), 2.29 (m, 1H), 1.39 (t, 3H). $^{13}$C NMR (carbonyl and/or amidine carbons; 100 MHz): δ 172.7, 171.7, 160.6, 152.0. LC-MS: (M+1) 489 m/z.

Example 14

Ph(3-Cl,5-NMe)-(R) or -(S)CH(OH)C(O)-Aze-Pab (O-n-Pr)

(i) Ph(3-Cl,5-NMe$_2$)-(R) or -(S)CH(OH)C(O)-Aze-Pab (Teoc)(O-n-Pr)

To a solution of Ph(3-Cl,5-NMe$_2$)-(R) or -(S)CH(OH)C(O)-Aze-Pab(Teoc) (40 mg, 0.07 mmol; see Example 6(vi) above) in THF (5 mL) was added O-n-propylhydroxylamine×HCl (46 mg, 0.41 mmol), and the solution was stirred at 60° C. overnight. The solution was concentrated to dryness, and the remainder was purified using preparative HPLC (CH$_3$CN:0.1 M ammonium acetate (60:40)). The fraction of interest was partially concentrated, and the aqueous solution was extracted with EtOAc (3×). The organic layer was washed with water, dried (Na$_2$SO$_4$) and concentrated to yield 16 mg (36%) of the sub-title compound.

$^1$H NMR (400 MHz; CDCl$_3$): δ 8.00 (bt, 1H), 7.58 (bs, 1H), 7.48 (d, 2H), 7.32 (d, 2H), 6.65 (s, 1H), 6.63 (s, 1H), 6.51 (s, 1H), 4.89 (dd, 1H), 4.82 (s, 1H), 4.50 (AB part of an ABX spectrum, 2H), 4.16 (dd, 1H), 4.11 (t, 1H), 4.06 (m, 1H), 3.65 (q, 1H), 2.96 (s, 6H), 2.68 (m, 1H), 2.39 (m, 1H), 1.75 (m, 2H), 0.98 (t, 5H), 0.05 (s, 9H). LC-MS: (M+1) 647 m/z.

(ii) Ph(3-Cl,5-NMe$_2$)-(R) or -(S)CH(OH)C(O)-Aze-Pab(O-n-Pr)

TFA (2 mL) was added to an ice-cold solution of Ph(3-Cl,5-NMe )-(R) or -(S)CH(OH)C(O)-Aze-Pab(Teoc)(O-n-Pr) (16 mg, 0.02 mmol; see step (i) above) in methylene chloride (0.5 mL), and the resulting mixture was stirred cold for 2 h. The resulting solution was concentrated in vacuo to give a solid residue that was dissolved in water/CH$_3$CN and freeze-dried. The product was purified using flash chromatography (EtOAc:MeOH (9:1)). The fractions of interest were concentrated to yield 14 mg (92%) of the title compound. Purity 98%.

$^1$H NMR (400 MHz; CDCl$_3$): δ 8.71 (bt, 1H), 7.65 (d, 2H), 7.50 (d, 2H), 6.73 (m, 2H), 6.67 (s, 1H), 5.07 (s, 1H), 4.78 (dd, 1H), 4.50 (AB part of an ABX spectrum, 2H), 4.32 (m, 1H), 4.06 (m, 3H), 2.94 (s, 6H), 2.49 (m, 1H), 2.29 (m, 1H), 1.80 (m, 2H), 1.03 (m, 3H). LC-MS: (M+1) 503 m/z.

Example 15

Ph(3-Cl,5-NMe$_2$)-(R) or -(S)CH(OH)C(O)-Aze-Pab (O-i-Pr)

(i) Ph(3-Cl,5-NMe$_2$)-(R) or -(S)CH(OH)C(O)-Aze-Pab (Teoc)(O-i-Pr)

O-Isopropylhydroxylamine×HCl (46 mg, 0.41 mmol) was added to a solution of Ph(3-Cl,5-NMe$_2$)-(R) or -(S)CH(OH)C(O)-Aze-Pab(Teoc) (40 mg, 0.07 mmol; see Example 6(vi) above) in THF (3 mL), and the resulting mixture was stirred at 60° C. overnight. The resultant solution was concentrated, and the crude product was purified using preparative HPLC (CH$_3$CN:0.1 M ammonium acetate (60:40)). The fractions of interest were partially concentrated and then extracted with EtOAc (3×). The combined organics were washed with water, dried (Na$_2$SO$_4$), and concentrated to yield 16 mg (36%) of the sub-title compound.

$^1$H NMR (400 MHz; CDCl$_3$): δ 8.00 (b, 1H), 7.57 (s, 1H), 7.50 (d, 2H), 7.32 (d, 2H), 6.65 (s, 1H), 6.63 (s, 1H), 6.51 (s, 1H), 4.90 (dd, 1H), 4.82 (s, 1H), 4.58–4.40 (m, 3H), 4.17 (m, 3H), 4.07 (m, 1H), 3.65 (m, 1H), 2.97 (s, 2H), 2.69 (m, 1H), 2.39 (m, 1H), 1.31 (d, 6H), 1.00 (m, 2H), 0.05 (s, 9H). LC-MS: (M+1) 647 m/z.

(ii) Ph(3-Cl,5-NMe$_2$)-(R) or -(S)CH(OH)C(O)-Aze-Pab(O-i-Pr)

An ice-cold solution of Ph(3-Cl,5-NMe$_2$)-(R) or -(S)CH(OH)C(O)-Aze-Pab(Teoc)(O-i-Pr) (16 mg, 0.02 mmol; see step (i) above) in TFA (1.5 mL) was stirred cold for 2 h. The resultant solution was evaporated in vacuo before water/CH$_3$CN was added, and the solution freeze-dried. The crude product was purified using flash chromatography (EtOAc:MeOH (9:1)). The fractions of interest were then concentrated to yield 14 mg (92%) of the title compound. Purity (HPLC) 96%.

$^1$H NMR (400 MHz; CDCl$_3$): δ 8.73 (bt, 1H), 7.66 (d, 2H), 7.50 (d, 2H), 6.73 (d, 2H), 6.67 (t, 1H), 5.08 (s, 1H), 4.78 (dd, 1H), 4.51 (AB part of an ABX spectrum, 2H), 4.4–4.3 (m, 2H), 4.02 (m, 1H), 2.95 (s, 6H), 2.51 (m, 1H), 2.30 (m, 1H), 1.39 (d, 6H). LC-MS: (M+1) 503 m/z.

Example 16

Ph(3-Cl,5-NMe$_2$)-(R) or -(S)CH(OH)C(O)-Aze-Pab (O—CH$_2$—CH$_2$—O—CH$_3$)

(i) Ph(3-Cl,5-NMe$_2$)-(R) or -(S)CH(OH)C(O)-Aze-Pab (Teoc)(O—CH$_2$—CH$_2$—O—CH$_3$)

A solution of O-(2-methoxy)ethylhydroxylamine and HOAc (23.3 μL) in THF (2 mL) was added to a solution of Ph(3-Cl,5-NMe$_2$)-(R) or -(S)CH(OH)C(O)-Aze-Pab(Teoc) (40 mg, 0.07 mmol; see Example 6(vi) above) in THF (1 mL), and the mixture was stirred at 60° C. for 3.5 days. The resultant solution was concentrated to dryness, and the crude product was purified using preparative HPLC (CH$_3$CN:0.1 M ammonium acetate (60:40)). The fractions of interest were partially concentrated and extracted with EtOAc (3×). The combined organic layers were washed with water, dried (Na$_2$SO$_4$) and then concentrated to dryness to yield 20 mg (44%) of the sub-title compound.

$^1$H NMR (400 MHz; CDCl$_3$): δ 8.00 (bt, 1H), 7.71 (b, 1H), 7.48 (d, 2H), 7.32 (d, 2H), 6.65 (s, 1H), 6.63 (s, 1H), 6.51 (s, 1H), 4.89 (dd, 1H), 4.81 (s, 1H), 4.49 (AB part of an ABX spectrum, 2H), 4.29 (m, 2H), 4.14 (m, 2H), 4.07 (m, 2H), 3.74–3.60 (m, 3H), 3.42 (s, 3H), 2.96 (s, 6H), 2.68 (m, 1H), 2.39 (m, 1H), 1.79 (b, 2H), 0.97 (m, 1H), 0.02 (s, 9H). LC-MS: (M+1) 663 m/z.

(ii) Ph(3-Cl,5-NMe$_2$)-(R) or -(S)CH(OH)C(O)-Aze-Pab (O—CH$_2$—CH$_2$—O—CH$_3$)

TFA (2 mL, 26 mmol) was added to an ice-cold solution of Ph(3-Cl,5-NMe$_2$)-(R) or -(S)CH(OH)C(O)-Aze-Pab (Teoc)(O—CH$_2$—CH$_2$—O—CH$_3$) (20 mg, 0.03 mmol; from step (i) above) in methylene chloride (0.5 mL), and the resulting mixture was stirred cold for 2½ h. The resultant solution was evaporated to dryness, and the crude product was purified by flash chromatography (EtOAc:MeOH (9:1)). The fractions of interest were concentrated to give a residue to which water/CH$_3$CN was added. The resulting solution was freeze-dried overnight to yield 13 mg (65%) of the title compound. Purity (HPLC) 96%.

$^1$H NMR (400 MHz; CD$_3$OD): δ 8.69 (bt, 1H), 7.65 (d, 2H), 7.49 (d, 2H), 6.73 (d, 2H), 6.67 (t, 1H), 5.07 (s, 2H), 4.78 (dd, 1H), 4.51 (AB part of an ABX spectrum, 2H), 4.32 (m, 1H), 4.22 (m, 2H), 4.03 (m, 1H), 3.72 (m, 2H), 3.41 (s, 3H), 2.94 (s, 6H), 2.48 (m, 1H), 2.29 (m, 1H). $^{13}$C NMR (carbonyl and/or amidine carbons; 100 MHz; CD$_3$OD): δ 172.7, 171.8, 171.7, 159.3, 152.0. LC-MS: (M+1) 519 m/z.

Example 17

Ph(3-Cl,5-NMe$_2$)-(R) or -(S)CH(OH)C(O)-Aze-Pab (O-THP)

(i) Ph(3-Cl,5-NMe)-(R) or -(S)CH(OH)C(O)-Aze-Pab (Teoc)(O-THP)

A solution of O-(tetrahydropyran-2-yl)-hydroxylamine (51 mg, 0.44 mmol) and HOAc (25 μL) in THF (1 ml) was added to a solution of Ph(3-Cl,5-NMe$_2$)-(R) or -(S)CH(OH)C(O)-Aze-Pab(Teoc) (43 mg, 0.07 mmol; see Example 6(vi) above) in THF (2 mL), and the resulting mixture was stirred at 60° C. for 22 h and then at RT overnight. The resultant solution was concentrated, and the crude product was purified via preparative HPLC (CH$_3$CN:0.1 M ammonium acetate (60:40)). The fractions of interest were partially concentrated and the aqueous remainder was extracted with EtOAc (3×). The combined organics were washed with water, dried (Na$_2$SO$_4$) and then concentrated to yield 26 mg (52%) of the sub-title compound.

$^1$H NMR (400 MHz; CDCl$_3$): δ 8.00 (bt, 1H), 7.61 (b, 1H), 7.52 (d, 2H), 7.32 (d, 2H), 6.66 (s, 1H), 6.63 (s, 1H), 6.51 (s, 1H), 5.30 (m, 1H), 4.90 (dd, 1H), 4.82 (s, 1H), 4.50 (AB part of an ABX spectrum, 2H), 4.17 (m, 2H), 4.07 (m, 1H), 3.95 (m, 1H), 3.66 (m, 2H), 2.97 (s, 6H), 2.69 (m, 1H), 2.39 (m, 1H), 2.00–1.55 (m, 7H), 0.98 (m, 2H), 0.04 (s, 9H). LC-MS: (M+1) 689 m/z.

(ii) Ph(3-Cl,5-NMe$_2$)-(R) or -(S)CH(OH)C(O)-Aze-Pab(O-THP)

Fluoride on Amberlyst® A-26 (140 mg) was added to a solution of Ph(3-Cl,5-NMe$_2$)-(R) or -(S)CH(OH)C(O)-Aze-Pab(Teoc)(O-THP) (34 mg, 0.05 mmol; see step (i) above) in CH$_3$CN (3 mL), and the mixture was left at 60° C. overnight. After cooling, the resin was removed by filtration and then washed with many portions of CH$_3$CN and EtOH (95%). The combined organics were concentrated to give a crude product that was purified via preparative HPLC (CH$_3$CN:0.1 M ammonium acetate (50:50)). The fractions of interest were concentrated, dissolved in water/CH$_3$CN and then freeze-dried to yield 18 mg (60%) of the title compound.

$^1$H NMR (400 MHz; CD$_3$OD): δ 7.62 (d, 2H), 7.32 (d, 2H), 6.72 (s, 2H), 6.66 (s, 1H), 5.15 (m, 1H), 5.05 (s, 1H), 4.77 (dd, 1H), 4.44 (AB part of an ABX spectrum, 2H), 4.29 (m, 1H), 3.95 (m, 2H), 3.57 (m, 1H), 2.93 (s, 6H), 2.48 (m, 1H), 2.27 (m, 1H), 1.94 (m, 2H), 1.82 (m, 1H), 1.75 (m, 1H), 1.61 (m, 3H). $^{13}$C NMR (carbonyl and/or amidine carbons; 100 MHz; CD$_3$OD): δ 172.7, 171.5, 154.7, 152.0. LC-MS: (M+1) 545 m/z.

Example 18

Ph(3-Cl,5-NMeAc)-(R) or -(S)CH(OH)C(O)-Aze-Pab(OMe)×TFA (i) Ph(3-Cl,5-NMeAc)-(R) or -(S)CH(OH)C(O)-Aze-Pab(Teoc)(OMe)

A mixture of Ph(3-Cl,5-NMeAc)-(R) or -(S)CH(OH)C(O)-Aze-Pab(Teoc) (38 mg, 0.06 mmol, see Example 5(vii) above) and O-methylhydroxylamine (62 mg, 0.74 mmol) in THF (3 mL) was heated at 60° C. for 30 h, whereafter the solvent was removed and the reaction mixture was purified by preparative HPLC (CH$_3$CN:0.1M ammonium acetate 50:50). The fraction of interest was partially concentrated and the aqueous remainder was extracted with EtOAc (3×). The combined organics were dried (Na$_2$SO$_4$) and concentrated in vacuo, yielding 22 mg (50%) of the sub-title compound.

$^1$H NMR (600 MHz; CDCl$_3$): δ 7.81 (br, 1H), 7.55 (br, 1H), 7.45 (d, 2H), 7.28 (d, 2H), 7.18 (br, 1H), 7.09 (br, 1H), 4.89 (s, 1H), 4.86 (dd, 1H), 4.46 (AB part of an ABX spectrum, 2H), 4.11 (m, 2H), 3.92 (s, 3H), 3.67 (br, 1H), 3.22 (br, 3H), 2.68 (br, 1H), 2.41 (m, 1H), 1.87 (br, 2H), 1.71 (m, 4H), 0.95 (m, 2H), −0.02 (s, 9H).

(ii) Ph(3-Cl,5-NMeAc)-(R) or -(S)CH(OH)C(O)-Aze-Pab(OMe)×TFA

A solution of Ph(3-Cl,5-NMeAc)-(R) or -(S)CH(OH)C(O)-Aze-Pab(Teoc)(OMe) (22 mg, 0.03 mmol, see step (i) above) in TFA (3 mL) was kept at RT for 1 h, whereafter the solvent was removed in vacuo. The solid remainder was dissolved in water and the solution was freeze-dried overnight, yielding 20 mg (76%) of the title compound.

$^1$H NMR (400 MHz; D$_2$O) (complex due to rotamerism): δ 8.79 (bt, 1H), 7.67 (t, 2H), 7.51 (d, 2H), 7.46 (d, 2H), 7.17 (s, 1H), 5.35 (s, 1H), 5.20 (s+m, 1H), 4.88 (dd, 1H), 4.55 (m, 1H), 4.40 (m, 1H), 4.11 (m, 2H), 3.98 (2×s, 3H), 3.38 (s, 1H), 3.19 (2s, 2H), 2.80 (m, 0.5H), 2.60 (m, 0.5H), 2.28 (m, 2H), 1.88 (s, 2H). $^{13}$C NMR (100 MHz, CD$_3$OD) (carbonyl and/or amidine carbons): δ 174.0; 173.3; 172.6; 172.5; 163.4; 163.0. LC-MS: (M+1) 502 m/z.

Example 19

Ph(3-(1-Pyrrolidin-2-one))-(R) or -(S)CH(OH)C(O)-Aze-Pab(OMe)×TFA (i) Ph(3-(1-Pyrrolidin-2-one))-(R) or -(S)CH(OH)C(O)-Aze-Pab(Teoc)(OMe)

O-Methylhydroxylamine×HCl (42 mg, 0.50 mmol) was added to a solution of Ph(3-(1-pyrrolidin-2-one))-(R) or -(S)CH(OH)C(O)-Aze-Pab(Teoc) (50 mg, 0.08 mmol; see Example 10(vii) above) in THF (3 mL), and the mixture was stirred overnight at 60° C. The solvent was removed and the residue partitioned between water and EtOAc. The water phase was extracted with EtOAc and the combined organic phases were dried (Na$_2$SO$_4$) and then concentrated in vacuo to afford ca. 52 mg (ca. 100%) of the sub-title compound as a solid, which was used without further purification.

LC-MS: (M+1) 624; (M−1) 622 m/z;

(ii) Ph(3-(1-Pyrrolidin-2-one))-(R) or -(S)CH(OH)C(O)-Aze-Pab(OMe)×TFA

A mixture of Ph(3-(1-pyrrolidin-2-one))-(R) or -(S)CH(OH)C(O)-Aze-Pab(Teoc)(OMe) (53 mg, 0.08 mmol; see step (i) above) and TFA (2.0 mL) in CH$_2$Cl$_2$ (1 mL) was stirred at RT for 4 hours. The solvent was removed and the residue partitioned between water and EtOAc. The water phase was extracted with EtOAc and the combined organic phases were dried (Na$_2$SO$_4$) and then concentrated in vacuo. The residue was chromatographed on silica gel, eluting with CH$_2$Cl$_2$:MeOH (98:2 to 95:5) to afford 22 mg (44%) of the title compound.

LC-MS: (M+1) 480; (M−1) 478 m/z; $^1$H NMR (400 MHz; CD$_3$OD): δ 7.76–7.63 (m, 3H), 7.59–7.50 (m, 3H), 7.44–7.20 (m, 2H), 5.20–5.14 (m, 1H), 4.61–4.02 (m, 4H), 3.97–3.87 (m, 5H), 2.74–2.44 (m, 3H), 2.34–2.09 (m, 3H).

Example 20

Ph(3-Cl,5-Pyrrolo)-(R) or -(S)CH(OH)C(O)-Aze-Pab (i) (R,S)-5-Ph(3-Cl,5-Pyrrolo)-2,2-dimethyl-4-oxo-1,3-dioxolane To a solution of (R,S)-5-Ph(3-Cl,5-NH$_2$)-2,2-dimethyl-4-oxo-1,3-dioxolane (6.0 g, 24.8 mmol; see Example 9(ii) above) and phosphorus pentoxide (3.5 g, 24.8 mmol) in dry toluene (50 mL) was added 2,5-dimethoxytetrahydrofuran (4.9 g, 37.3 mmol) dropwise. The reaction was heated to reflux for 30 min and then allowed to cool to room temperature. The reaction was quenched with 2 N NaOH (10 mL), transferred to a separatory funnel and the aqueous phase was separated and extracted with toluene (100 mL). The combined organic phases were subsequently washed with brine (20 mL), dried (MgSO$_4$), filtered and concentrated in vacuo to afford a pale orange oil (5.0 g). Flash chromatography on silica gel eluting with CH$_2$Cl$_2$ afforded 2.8 g (39%) of the sub-title compound as a yellow solid.

$^1$H NMR (300 MHz, CD$_3$OD): δ 7.28–7.42 (m, 3H), 7.18 (t, J=2.1 Hz, 2H), 6.38 (t, J=2.1 Hz, 2H), 5.40 (s, 1H), 1.72 (d, J=8.2 Hz, 6H).

(ii) Ph(3-Cl,5-Pyrrolo)-(R,S)CH(OH)C(O)OH

To a solution of (R,S)-5-Ph(3-Cl,5-pyrrolo)-2,2-dimethyl-4-oxo-1,3-dioxolane (3.1 g, 10.7 mmol; see step (i) above) in THF (40 mL) at room temperature was added 3 N NaOH (36 mL, 107.3 mmol) together with tetrabutylammonium bromide (0.35 g, 1.07 mmol). The reaction mixture was then stirred at room temperature for a further 2 h. The reaction mixture was concentrated in vacuo to remove THF. The remaining aqueous phase was cooled to 0° C. and acidified to pH 2 with concentrated HCl and extracted with EtOAc (2×150 mL). The combined organics were washed with brine, dried (MgSO$_4$), filtered and concentrated in vacuo to afford an orange foam. Flash chromatography on silica gel, eluting with CHCl$_3$:MeOH:concentrated ammonium hydroxide (85:15:5), afforded the ammonium salt of the sub-title compound as a white solid (2.0 g). Subsequent acidification with 2 N HCl to pH 1, followed by extraction with EtOAc, concentrating in vacuo and drying, afforded 1.8 g (68%) of the sub-title compound as a white solid.

$^1$H NMR (300 MHz, CD$_3$OD): δ 7.52 (s, 1H), 7.46 (s, 1H), 7.36 (s, 1H), 7.22 (t, J=3 Hz, 2H), 6.32 (t, J=3 Hz, 2H), 5.4 (s, 1H).

(iii) Ph(3-Cl,5-Pyrrolo)-(R) or -(S)CH(OH)C(O)OH (a) and Ph(3-Cl, 5-pyrrolo)-(S) or -(R)CH(OAc)C(O)OH (b)

A mixture of Ph(3-Cl,5-pyrrolo)-(R,S)CH(OH)C(O)OH (1.8 g, 7.3 mmol; see step (ii) above), Lipase PS 'Amano' (1.0 g), vinyl acetate (5.0 mL) and MTBE (5.0 mL) was heated at 45° C. for 24 h. The reaction was filtered and the filter cake washed with EtOAc (100 mL). The filtrate was concentrated in vacuo and chromatographed on silica, eluting with CHCl$_3$:HOAc (95:5), to afford 710 mg, (38%) of sub-title compound (a) as a white solid and 910 mg (42%) of sub-title compound (b) as a cream colored solid.

For sub-title compound (a): $^1$H NMR (300 MHz, CD$_3$OD): δ 7.54 (s, 1H), 7.47 (s, 1H), 7.36 (s, 1H), 7.19 (d, J=3 Hz, 2H), 6.30 (d, J=3 Hz, 2H), 5.21(s, 1H). $^{13}$C NMR (75 MHz, CD$_3$OD): δ 175.2, 142.9, 136.1, 124.4, 120.3, 119.9, 117.3, 112.0, 73.2. HPLC Analysis: 98.3%, 98.0% ee; $[α]_D^{25}$=−99° (c=1.0, methanol); API-MS: (M+1) 252 m/z; For sub-title compound (b): $^1$H NMR (300 MHz, CD$_3$OD): δ 7.52 (s, 1H), 7.46 (s, 1H), 7.38 (s, 1H), 7.20 (br s, 2H), 6.30 (br s, 2H), 5.22 (s, 1H), 1.98 (s, 3H).

(iv) Ph(3-Cl,5-Pyrrolo)-(R) or -(S)CH(OH)C(O)-Aze-Pab (Teoc)

A mixture of Ph(3-Cl,5-pyrrolo)-(R) or -(S)CH(OH)C(O) OH (285 mg, 1.14 mmol; see step (iii) above), HAze-Pab (Teoc) (470 mg, 1.25 mmol), PyBOP (650 mg, 1.25 mmol), and 2,4,6-collidine (0.33 mL, 2.49 mmol) in DMF (14 mL) was stirred at 0° C. for 2 h and then at 25° C. for 30 minutes. The reaction was quenched with H$_2$O (50 mL) and extracted with EtOAc (3×50 mL). The combined extracts were dried (Na$_2$SO$_4$), filtered and concentrated in vacuo. Flash chromatography (2×) on silica gel eluting with EtOAc afforded 180 mg (26%) of the sub-title compound as a white solid.

$^1$H NMR (300 MHz, CD$_3$OD): δ 7.74–7.86 (m, 2H), 7.14–7.58 (m, 7H), 6.28 (br s, 2H), 5.14–5.28 (m, 2H), 4.76–4.82 (m, 1H), 3.92–4.58 (m, 7H), 2.40–2.68 (m, 2H), 2.10–2.38 (m, 2H), 1.02–1.16 (m, 2H), 0.09 (s, 9H). API-MS: (M+1) 610 m/z.

(v) Ph(3-Cl,5-Pyrrolo)-(R) or -(S)CH(OH)C(O)-Aze-Pab

To a solution of Ph(3-Cl,5-pyrrolo)-(R) or -(S)CH(OH)C(O)-Aze-Pab(Teoc) (38 mg, 0.06 mmol; see step (iv) above) in acetonitrile was added polymer bound fluoride ion (Amberlyst® A-26) (170 mg) and the mixture was heated at 60° C. overnight followed by 70° C. for 4 h. The resultant mixture was filtered, the polymer was washed with and the solution was with acetonitrile, ethanol and THF, and the solution was concentrated in vacuo. The crude product was purified twice using preparative HPLC (CH$_3$CN:0.1 M ammonium acetate, 40:60 and CH$_3$CN:0.1 M ammonium acetate, 30:70, respectively). The fractions of interest were freeze-dried (3×), yielding 8 mg (28%) of the title compound.

$^1$H NMR (400 MHz, CD$_3$OD): δ 7.77 (m, 2H), 7.61–7.48 (m, 3H), 7.40 (d, 1H), 7.26 (m, 2H), 6.33 (m, 2H), 5.30 (d, 1H), 4.68–4.25 (m, 2H), 4.09 (m, 1H), 2.60 (m, 1H), 2.35 (m, 1H), 1.94 (s, 3H). LC-MS: (M+1) 466 m/z.

Example 21

Ph(3-Cl,5-(1-Pyrrolidin-2-one))-(R) or -(S)CH(OH)C(O)-Aze-Pab(O-n-Pr)

(i) Ph(3-Cl,5-(1-Pyrrolidin-2-one))-(R) or -(S)CH(OH)C(O)-Aze-Pab(Teoc)(O-n-Pr)

To a solution of Ph(3-Cl,5-(1-pyrrolidin-2-one))-(R) or -(S)CH(OH)C(O)-Aze-Pab(Teoc) (40 mg, 0.064 mol; see Example 9(vi) above) in THF (3 mL) was added O-n-propylhydroxylamine×HCl (43 mg, 0.38 mmol), and the solution was heated at 60° C. for 4.5 h. The solution was concentrated in vacuo, and the resultant crude material was purified by flash chromatography (Si gel, EtOAc:MeOH 9:1). The fractions of interest were concentrated, yielding 43 mg (98%) of the sub-title compound.

$^1$H NMR (400 MHz; CD$_3$OD): δ 7.75 (2s, 1H), 7.59 (br, 1H), 7.43 (d, 2H), 7.23 (m, 3H), 5.18 (br, 1H), 4.50–4.30 (m, 3H), 4.20–4.05 (m, 5H), 3.99 (t, 3H), 3.84 (m, 2H), 2.55 (t, 2H), 2.28 (m, 1H), 2.12 (m, 2H), 1.71 (m, 2H), 0.99 (m, 4H), 0.02 (s, 9H).

(ii) Ph(3-Cl,5-(1-Pyrrolidin-2-one))-(R) or -(S)CH(OH)C(O)-Aze-Pab(O-n-Pr)

To an ice-cold solution of Ph(3-Cl,5-(1-pyrrolidin-2-one))-(R) or -(S)CH(OH)C(O)-Aze-Pab(O-n-Pr)(Teoc) (43 mg, 0.063 mmol; from Step (i) above) in methylene chloride (0.5 mL) was added TFA (2.5 mL), and the solution was stirred at 0° C. for 100 min, whereafter the solution was concentrated in vacuo and the resultant crude material was purified using preparative HPLC (CH$_3$CN:0.1M ammonium acetate 30:70). The fractions of interest were pooled and freeze-dried, yielding 23 mg (68%).

Purity 99.9%; LC-MS (M+1) 542 m/z; $^1$H NMR (400 MHz; CD$_3$OD) (complex due to rotamerism): δ 7.75 (br, 1H), 7.57 (m, 2.5H), 7.49 (s, 0.5H), 7.36–7.22 (m, 3H), 5.16 (s, 1H), 4.78 (dd, 1H), 4.48–4.32 (m, 3H), 4.17 (m, 1H), 3.97 (m, 2H), 3.86 (m, 2H), 2.55 (t, 3H), 2.52 (m, 0.5H), 2.28 (m, 0.5H), 2.13 (m, 3H), 1.71 (m, 2H), 0.98 (m, 2H).

Example 22

Ph(3-Cl,5-(1-Pyrrolidin-2-one))-(R)- or -(S)CH(OH)C(O)-Aze-Pab(OMe)

(i) Ph(3-Cl,5-(1-Pyrrolidin-2-one))-(R)- or -(S)CH(OH)C(O)-Aze-Pab(Teoc)(OMe)

To a mixture of Ph(3-Cl,5-(1-pyrrolidin-2-one))-(R)- or -(S)CH(OH)C(O)-Aze-Pab(Teoc) (80 mg, 0.13 mmol; see Example 9(vi) above) in THF (6 mL) was added O-methylhydroxylamine×HCl (64 mg, 0.77 mmol). The mixture was stirred at 60° C. for 5 h and then evaporated. The residue was chromatographed on silica gel, eluting with ethyl acetate:methanol (9:1), to afford 75 mg of crude product. The crude product was further purified using preparative HPLC (CH$_3$CN:0.1 M ammonium acetate, 60:40). The fractions of interest were concentrated. CH$_3$CN was removed in vacuo. The aqueous phase was extracted with EtOAc (3×). The combined ethyl acetate phases were washed with brine, then dried (Na$_2$SO$_4$) and concentrated, yielding 65.8 mg (78%) of the sub-title compound.

$^1$H NMR (400 MHz; CDCl$_3$): δ 7.97–7.90 (m, 1H), 7.60–7.55 (m, 2H), 7.46 (d, 2H), 7.29 (d, 2H), 7.13 (s, 1H), 4.95–4.81 (m, 2H), 4.55–4.30 (m, 3H), 4.18–4.09 (m, 3H), 3.95 (s, 3H), 3.87–3.75 (m, 3H), 2.69–2.55 (m, 3H), 2.45–2.34 (m, 1H), 2.20–2.10 (m, 2H), 2.00 (br, 1H), 1.01–0.92 (m, 2H), 0.00 (s, 9H).

(ii) Ph(3-Cl,5-(1-Pyrrolidin-2-one))-(R)- or -(S)CH(OH)C(O)-Aze-Pab(OMe)

To an ice-cold solution of Ph(3-Cl,5-(1-pyrrolidin-2-one))-(R)- or -(S)CH(OH)C(O)-Aze-Pab(Teoc)(OMe) (55.9 mg, 0.08 mmol; from step (i) above) in methylene chloride (0.5 mL) was added TFA (3.0 mL). The solution was stirred at 0° C. for 130 min., whereafter the solution was concentrated in vacuo and the resultant crude material was purified using preparative HPLC (CH$_3$CN:0.1M ammonium acetate, 30:70). The fractions of interest were pooled and freeze-dried (2×), yielding 38 mg (87%) of the title compound.

LC-MS (M+1) 514 m/z; $^1$H NMR (400 MHz; CD$_3$OD): δ 7.75 (s, 1H), 7.62–7.47 (m, 3H), 7.36–7.21 (m, 3H), 5.19–5.10 (m, 1H), 4.48–3.93 (m, 4H), 3.89–3.79 (m, 5H), 2.72–2.45 (m, 3H), 2.33–2.06 (m, 3H).

Example 23

Ph(3-Cl,5-NMe(3-Methylbutanoyl))-(R)- or -(S)CH(OH)C(O)-Aze-Pab(OMe)

(i) (R,S)-5-Ph(3-Cl,5-NHMe)-2,2-Dimethyl-4-oxo-1,3-dioxolane

A mixture of (R,S)-5-Ph(3-Cl,5NH$_2$)-2,2-dimethyl-4-oxo-1,3-dioxolane (3.0 g, 12.4 mmol; see Example 9(ii) above), formaldehyde (0.81 mL of 37 wt % in H$_2$O, 9.9 mmol) and platinum(IV)oxide (330 mg) in EtOAc (100 mL) was stirred under a hydrogen atmosphere for 5 h at 25° C. The mixture was filtered through a pad of Celite and the filter cake washed with EtOAc (200 mL). The organics were concentrated in vacuo and flashed chromatographed on silica gel eluting with EtOAc:Hex (1:4) to afford 1.63 g (52%) of the sub-title compound as a yellow oil.

$^1$H NMR (300 MHz, CDCl$_3$): δ 6.75 (s, 1H), 6.54 (s, 2H), 5.25 (s, 1H), 3.90 (br s, 1H), 2.80 (s, 3H), 1.68 (s, 3H), 1.64 (s, 3H).

(ii) (R,S)-5-Ph(3-Cl,5-NMe(3-Methylbutanoyl))-2,2-dimethyl-4-oxo-1,3-dioxolane

To a solution of (R,S)-5-Ph(3-Cl,5-NHMe)-2,2-dimethyl-4-oxo-1,3-dioxolane (945 mg, 3.70 mmol; see step (i) above) and triethylamine (560 mg, 5.54 mmol) in acetone (20 mL) at 0° C. was added dropwise isovaleryl chloride (623 mg, 5.17 mmol). The mixture was stirred for 0.5 h, and partitioned with EtOAc (3×30 mL) and H$_2$O (30 mL). The combined organic extracts were washed with aqueous NaHCO$_3$ (30 mL), dried (Na$_2$SO$_4$), filtered and concentrated in vacuo to afford 1.35 g (>100%) of the sub-title compound as a yellow oil, which was used directly without purification.

$^1$H NMR (300 MHz, CDCl$_3$): δ 7.50 (s, 1H), 7.20 (s, 2H), 5.38 (s, 1H), 3.28 (s, 3H), 1.90–2.22 (m, 3H), 1.70 (s, 3H), 1.68 (s, 3H), 0.70–0.92 (m, 6H).

(iii) Ph(3-Cl,5-NMe(3-Methylbutanoyl))-(R,S)CH(OH)C(O)OH

A mixture of (R,S)-5-Ph(3-Cl,5-NMe(3-methylbutanoyl))-2,2-dimethyl-4-oxo-1,3-dioxolane (1.35 g, 3.97 mmol; see step (ii) above) and NaOH (1.60 g, 39.7 mmol) in MeOH (20 mL) was stirred for 1 h at 25° C. The mixture was concentrated in vacuo, and the residue was diluted with H$_2$O (30 mL), acidified with 2N HCl (20 mL) and extracted with EtOAc (3×50 mL). The combined organic extracts were dried (Na$_2$SO$_4$), filtered and concentrated in vacuo to give 1.0 g (100%) of the sub-title compound as a yellow oil, which was used directly without purification.

$^1$H NMR (300 MHz, CD$_3$OD): δ 7.55 (s, 1H), 7.34 (s, 2H), 5.21 (s, 1H), 3.23 (s, 3H), 1.90–2.10 (m, 3H), 0.70–0.92 (m, 6H).

(iv) Ph(3-Cl,5-NMe(3-Methylbutanoyl))-(R)- or -(S)—CH(OH)C(O)OH (a) and Ph(3-Cl,5-NMe(3-Methylbutanoyl))-(S)- or -(R)—CH(OAc)C(O)OH (b)

A mixture of Ph(3-Cl,5-NMe(3-methylbutanoyl))-(R,S)CH(OH)C(O)OH (1.0 g, 3.34 mmol; see step (iii) above) and Lipase PS Amano (510 mg) in vinyl acetate (25 mL) and MTBE (25 mL) was heated at 55° C. for 14 h. The reaction was filtered through Celite and the filter cake washed with MeOH (200 mL). The filtrate was concentrated in vacuo and chromatographed on silica gel eluting with CHCl$_3$:MeOH:concentrated NH$_4$OH (6.5:3.0:0.5) to afford 285 mg of the ammonium salt of the sub-title compound (a) as a crushable foam and 370 mg (32%) of the amnonium salt of sub-title compound (b) as a white foam. The ammonium salt of the sub-title compound (a) was taken up in EtOAc (25 mL) and neutralized with 2M HCl in Et$_2$O (0.60 mL). Water (25 mL) was added, and the layers were separated. The aqueous layer was extracted with EtOAc (2×25 mL), and the organic extracts were dried (Na$_2$SO$_4$), filtered, and concentrated in vacuo to give 230 mg (23%) of the sub-title compound (a) as a crushable white foam.

For sub-title compound (a): $^1$H NMR (300 MHz, CD$_3$OD): δ 7.55 (s, 1H), 7.34 (s, 1H), 7.30 (s, 1H), 5.21 (s, 1H), 3.23 (s, 3H), 1.90–2.10 (m, 3H), 0.70–0.92 (m, 6H). $^{13}$C NMR (75 MHz, CD$_3$OD): δ 175.4, 175.0, 146.6, 145.2, 136.2, 128.1, 127.4, 125.6, 73.6, 44.0, 37.7, 27.4, 22.8; HPLC Analysis: 96.0%, >99% ee; [α]$_D^{25}$=−85.1° (c=0.5, MeOH); API-MS (M+1)=300 m/z; For sub-title compound (b):

$^1$H NMR (300 MHz, CD$_3$OD): δ 7.55 (s, 1H), 7.34 (s, 1H), 7.30 (s, 1H), 5.75 (s, 1H), 3.23 (s, 3H), 2.11 (s, 3H), 1.90–2.10 (m, 3H), 0.70–0.92 (m, 6H).

(v) Ph(3-Cl,5-NMe(3-Methylbutanoyl))-(R)- or -(S)CH(OH)C(O)-Aze-Pab(OMe)

To a mixture of Ph(3-Cl,5-NMe(3-methylbutanoyl))-(R)- or -(S)—CH(OH)C(O)OH (119 mg, 0.40 mmol; see step (iv) above) and H-Aze-Pab(OMe)×2HCl (146 mg, 0.44 mmol; see Example 2(iv) above) in DMF (5 mL) was added PyBOP (227 mg, 0.44 mmol) and collidine (168 mg, 1.39 mmol). The solution was stirred for 3 h at 0° C. under nitrogen. The mixture was partitioned with EtOAc (3×30 mL) and H$_2$O (30 mL), dried (Na$_2$SO$_4$), filtered, and concentrated in vacuo. Flash chromatography on silica gel eluting with CHCl$_3$:MeOH (15:1) gave 125 mg (58%) of the title compound as a crushable white foam.

$^1$H NMR (300 MHz, CD$_3$OD, mixture of rotamers): δ 7.60 (d, J=8 Hz, 2H), 7.42–7.54 (m, 1H), 7.20–7.50 (m, 4H), 5.20 and 5.14 (s, 1H), 4.72–4.81 (m, 1H), 4.30–4.48 (m, 3H), 3.90–4.20 (m, 2H), 3.80 (s, 3H), 3.22 (s, 3H), 2.46–2.72 (m, 2H), 2.10–2.36 (m, 1H), 1.94–2.10 (m, 2H), 0.80–0.94 (m, 6H); API-MS (M+1)=545 m/z.

Example 24

Ph(3-Cl,5-NMe(Cyclopentylcarbonyl))-(R)- or -(S) CH(OH)C(O)-Aze-Pab(OMe)

(i) (R,S)-5-Ph(3-Cl,5-NMe(Cyclopentylcarbonyl))-2,2-dimethyl-4-oxo-1,3-dioxolane To a solution of (R,S)-5-Ph(3-Cl,5-NHMe)-2,2-dimethyl-4-oxo-1,3-dioxolane (945 mg, 3.70 mmol; see Example 23(i) above) and triethylamine (635 mg, 5.86 mmol) in acetone (20 mL) at 0° C. was added dropwise cyclopentanecarbonyl chloride (776 mg, 5.86 mmol). The mixture was stirred for 1 h, and partitioned with EtOAc (3×30 mL) and H$_2$O (30 mL). The combined organic extracts were washed with aqueous NaHCO$_3$ (30 mL), dried (Na$_2$SO$_4$), filtered and concentrated in vacuo to afford 1.58 g (>100%) of the sub-title compound as a yellow oil, which was used directly without purification.

$^1$H NMR (300 MHz, CDCl$_3$): δ 7.50 (s, 1H), 7.20 (s, 2H), 5.38 (s, 1H), 3.28 (s, 3H), 2.50–2.60 (m, 1H), 1.70 (s, 3H), 1.68 (s, 3H), 1.40–1.90 (m, 8H).

(ii) Ph(3-Cl,5-NMe(Cyclopentylcarbonyl))-(R,S)CH(OH)C(O)OH

A mixture of (R,S)-5-Ph(3-Cl,5-NMe(cyclopentylcarbonyl))-2,2-dimethyl-4-oxo-1,3-dioxolane (1.58 g, 5.07 mmol; see step (i) above) and NaOH (2.03 g, 50.7 mmol) in MeOH (25 mL) was stirred 1 h at 25° C. The mixture was concentrated in vacuo, diluted with H$_2$O (30 mL), and acidified with 2N HCl (20 mL). The aqueous layer was extracted with EtOAc (3×50 mL), the combined organic extracts were dried (Na$_2$SO$_4$), filtered and concentrated in vacuo to give 1.17 g (100%) of the sub-title compound as a white foam, which was used directly without purification.

$^1$H NMR (300 MHz, CD$_3$OD): δ 7.55 (s, 1H), 7.32 (s, 2H), 5.20 (s, 1H), 3.20 (s, 3H), 2.50–2.62 (m, 1H), 1.40–1.80 (m, 8H).

(iii) Ph(3-Cl,5-NMe(Cyclopentylcarbonyl))-(R)- or -(S)—CH(OH)C(O)OH (a) and Ph(3-Cl,5-NMe(Cyclopentylcarbonyl))-(S)- or -(R)—CH(OAc)C(O)OH (b)

A mixture of Ph(3-Cl,5-NMe(cyclopentylcarbonyl))-(R,S)CH(OH)C(O)OH (1.17 g, 3.75 mmol; see step (ii) above) and Lipase PS Amano (600 mg) in vinyl acetate (25 mL), and MTBE (25 mL) was heated at 55° C. for 14 h. The reaction was filtered through Celite and the filter cake washed with MeOH (100 mL). The filtrate was concentrated in vacuo and chromatographed on silica gel eluting with CHCl₃:MeOH:concentrated NH₄OH (6.5:3.0:0.5) to afford 336 mg of the ammonium salt of the sub-title compound (a) as a crushable foam and 557 mg (50%) of the ammonium salt of sub-title compound (b) as a white foam. The ammonium salt of the sub-title compound (a) was taken up in EtOAc (25 mL), and neutralized with 2M HCl in Et₂O (0.70 mL). Water (25 mL) was added, and the layers were separated. The aqueous layer was extracted with EtOAc (2×25 mL), and the organic extracts were dried (Na₂SO₄), filtered, and concentrated to give 290 mg (29%) of the sub-title compound (a) as a crushable white foam.

For sub-title compound (a): $^1$H NMR (300 MHz, CD₃OD): δ 7.55 (s, 1H), 7.32 (s, 2H), 5.20 (s, 1H), 3.20 (s, 3H), 2.50–2.62 (m, 1H), 1.40–1.80 (m, 8H). $^{13}$C NMR (75 MHz, CD₃OD): δ 178.8, 175.1, 146.5, 144.9, 136.2, 128.2, 127.5, 125.7, 73.0, 43.4, 38.0, 32.2, 27.3; HPLC Analysis: 91.9%, >99% ee; $[\alpha]_D^{25}$=−77.9° (c=1.0, MeOH); CI-MS (M+1)=312 m/z; For sub-title compound (b): $^1$H NMR (300 MHz, CD₃OD): δ 7.55 (s, 1H), 7.40 (s, 1H), 7.34 (s, 1H), 5.75 (s, 1H), 3.20 (s, 3H), 2.50–2.62 (m, 1H), 2.18 (s, 3H), 1.40–1.80 (m, 8H).

(iv) Ph(3-Cl,5-NMe(Cyclopentylcarbonyl))-(R)- or -(S)CH(OH)C(O)-Aze-Pab(OMe)

To a mixture of Ph(3-Cl,5-NMe(cyclopentylcarbonyl))-(R,S)CH(OH)C(O)OH (120 mg, 0.39 mmol; see step (iii) above) and H-Aze-Pab(OMe)×2HCl (142 mg, 0.42 mmol; see Example 2(iv) above) in DMF (5 mL) was added PyBOP (220 mg, 0.42 mmol) and collidine (161 mg, 1.35 mmol). The solution was stirred for 6 h at 0° C. under nitrogen. The mixture was partitioned with EtOAc (3×30 mL) and H₂O (30 mL), dried (Na₂SO₄), filtered, and concentrated in vacuo. Flash chromatography on silica gel eluting with CHCl₃:MeOH (15:1), followed by chromatography with EtOAc:EtOH (20:1) gave 85 mg (40%) of the title compound as a crushable white foam.

$^1$H NMR (300 MHz, CD₃OD, mixture of rotamers): δ 7.60 (d, J=8 Hz, 2H), 7.42–7.54 (m, 1H), 7.20–7.50 (m, 4H), 5.20 and 5.14 (s, 1H), 4.72–4.81 (m, 1H), 4.30–4.48 (m, 3H), 3.90–4.20 (m, 2H), 3.80 (s, 3H), 3.22 (s, 3H), 2.46–2.72 (m, 2H), 2.10–2.36 (m, 1H), 1.40–1.80 (m, 8H); API-MS (M+1)=556 m/z.

Example 25

The title compounds of Examples 1, 3 to 11 and 20 were tested in Test A above and were found to exhibit an IC₅₀TT value of less than 0.5 μM.

Example 26

The title compounds of Examples 2, 12, 13, 15, 18, 19 and 21 were tested in Test E above and were found to exhibit oral and/or parenteral bioavailability in the rat as the corresponding active inhibitor (free amidine).

Example 27

The title compounds of Examples 2, 12 to 19 and 21 were tested in Test G above and exhibited formation of the corresponding active inhibitor (free amidine).

| Abbreviations | |
|---|---|
| Ac | acetyl |
| AcOH | acetic acid |
| API | atmospheric pressure ionisation (in relation to MS) |

-continued

| Abbreviations | |
|---|---|
| Aze | azetidine-2-carboxylate |
| AzeOH | azetidine-2-carboxylic acid |
| Bzl | benzyl |
| CI | chemical ionisation (in relation to MS) |
| DIPEA | diisopropylethylamine |
| DMAP | 4-(N,N-dimethyl amino) pyridine |
| DMF | dimethylformamide |
| DMSO | dimethylsulphoxide |
| EDC | 1-(3-dimethylaminopropyl)-3-ethylcarbodiimide hydrochloride |
| Et | ethyl |
| ether | diethyl ether |
| EtOAc | ethyl acetate |
| EtOH | ethanol |
| h | hours |
| HATU | O-(azabenzotriazol-1-yl)-N,N,N',N'-tetramethyluronium hexafluorophosphate |
| HBTU | [N,N,N',N'-tetramethyl-O-(benzotriazol-1-yl)uronium hexafluorophosphate] |
| HCl | hydrochloric acid |
| HCl(g) | hydrogen chloride gas |
| Hex | hexanes |
| HOAc | acetic acid |
| HPLC | high performance liquid chromatography |
| LC | liquid chromatography |
| Me | methyl |
| MeOH | methanol |
| MS | mass spectroscopy |
| MTBE | methyl tert-butyl ether |
| Pab | para-amidinobenzylamino |
| H-Pab | para-amidinobenzylamine |
| PyBOP | (benzotriazol-1-yloxy)tripyrrolidinophosphonium hexafluorophosphate |
| RPLC | reverse phase high performance liquid chromatography |
| RT | room temperature |
| TBTU | [N,N,N',N'-tetramethyl-O-(benzotriazol-1-yl)uronium tetrafluoroborate] |
| TEA | triethylamine |
| Teoc | 2-(trimethylsilyl)ethoxycarbonyl |
| TFA | trifluoroacetic acid |
| THF | tetrahydrofuran |
| THP | tetrahydropyranyl |
| TLC | thin layer chromatography |
| TMSCN | trimethylsilyl cyanide |
| Z | benzyloxycarbonyl |

Prefixes n, s, i and t have their usual meanings: normal, secondary, iso and tertiary.

What is claimed is:
1. A compound of formula I,

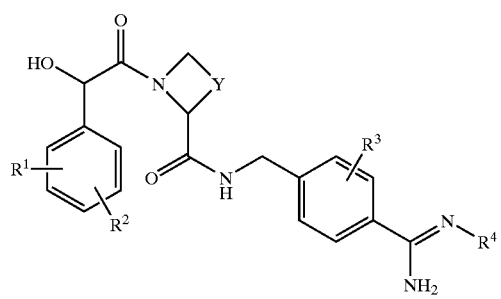

I wherein
R$^1$ represents a N(R$^5$)R$^6$ or a S(O)$_m$R$^7$ substituent;
R$^2$ and R$^3$ independently represent an optional substituent selected from halo, C$_{1-4}$ alkyl or C$_{1-4}$ alkoxy, which latter two groups are optionally substituted by halo;
Y represents C$_{1-3}$ alkylene, optionally substituted by C$_{1-4}$ alkyl, methylene, =O or hydroxy;

R⁴ represents H, OH, OR$^{8a}$, C(O)OR$^{8b}$ or R$^{8c}$;

R⁵ represents $C_{1-6}$ alkyl, optionally substituted by halo, or, together with R⁶ and the nitrogen atom to which R⁵ and R⁶ are attached, represents a 3- to 7-membered nitrogen containing ring, which ring optionally includes an oxygen atom and/or is optionally substituted with a =O group;

R⁶ represents $C_{1-6}$ alkyl, optionally substituted by halo, C(O)R⁹ or, together with R⁵ and the nitrogen atom to which R⁵ and R⁶ are attached, represents 3- to 7-membered nitrogen-containing ring, which ring optionally includes an oxygen atom and/or is optionally substituted with a =O group;

or the group N(R⁵)R⁶ represents the structural fragment Ia,

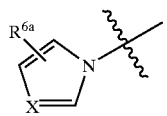

Ia

R$^{6a}$ represents one or more optional substituents selected from halo, $C_{1-4}$ alkyl and $C_{1-4}$ alkoxy, which latter two groups are optionally substituted by halo;

X represents CH or N;

m represents 0, 1 or 2;

R⁷ represents H, NH₂ or $C_{1-6}$ alkyl;

R$^{8a}$ and R$^{8b}$ independently represent $C_{1-10}$ alkyl, $C_{1-3}$ alkylphenyl or $C_{6-10}$ aryl, or R$^{8a}$ represents C(R$^{10a}$)(R$^{10b}$)OC(O)R¹¹, C(R$^{10a}$)(R$^{10b}$)N(H)C(O)OR¹² or C(R$^{10a}$)(R$^{10b}$)OC(O)N(H)R¹²;

R$^{8c}$ represents C(R$^{10a}$)(R$^{10b}$)OC(O)R¹¹, C(R$^{10a}$)(R$^{10b}$)N(H)C(O)OR¹² or C(R$^{10a}$)(R$^{10b}$)OC(O)R¹²;

R$^{10a}$ and R$^{10b}$ independently represent, at each occurrence, H or $C_{1-4}$ alkyl;

R¹¹ represents, at each occurrence, $C_{6-10}$ aryl, OR¹² or $C_{1-7}$ alkyl, which latter group is optionally substituted by a substituent selected from OH, CO₂H and $C_{6-10}$ aryl;

R¹² represents, at each occurrence, $C_{6-10}$ aryl or $C_{1-6}$ alkyl, which latter group is optionally substituted by a substituent selected from OH, CO₂H and $C_{6-10}$ aryl;

R⁹ represents $C_{1-8}$ alkyl, Het¹, $C_{6-10}$ aryl or $C_{1-4}$ alkyl substituted by $C_{6-10}$ aryl; and Het¹ represents a 4- to 12-membered heterocyclic ring, which ring contains one or more heteroatoms selected from oxygen, nitrogen and/or sulfur, and which ring may be fully saturated, partially saturated or aromatic and/or optionally monocyclic, bicyclic and/or benzo-fused; wherein each aryl/phenyl group and Het¹ group identified above is optionally substituted by one or more halo, $C_{1-4}$ alkyl and/or $C_{1-4}$ alkoxy groups, which latter two groups are themselves optionally substituted by one or more halo groups;

or a pharmaceutically acceptable salt thereof, provided that:

(a) when m represents 1 or 2, then R⁷ does not represent H; and (b) when m represents 0, then R⁷ does not represent NH₂.

2. A compound as claimed in claim 1 wherein, when R⁵ and R⁶, together with the nitrogen atom to which they are attached, represent a 3- to 7-membered ring substituted by a =O group, the ring is substituted at a carbon atom that is α to the nitrogen atom.

3. A compound as claimed in claim 1, wherein R², if present, represents linear or branched $C_{1-4}$ alkyl or $C_{1-4}$ alkoxy, which latter two groups are optionally substituted by halo, or halo.

4. A compound as claimed in claim 1, wherein R³ is either absent or, if present, represents linear or branched $C_{1-4}$ alkyl or halo.

5. A compound as claimed in claim 4, wherein R³, if present, represents a methyl or a chloro group.

6. A compound as claimed in claim 4, wherein the substituent, if present, is in the 2-position relative to the —CH₂— group to which the phenyl ring is also attached.

7. A compound as claimed in claim 1, wherein R¹ represents N(R⁵)R⁶.

8. A compound as claimed in claim 1, wherein R⁵ represents linear, branched or cyclic $C_{1-6}$ alkyl or, together with R⁶ and the nitrogen atom to which R⁵ and R⁶ are attached, represents a 4- to 6-membered nitrogen containing ring, optionally substituted with a =O group.

9. A compound as claimed in claim 8, wherein R⁵ represents $C_{1-4}$ alkyl or, together with R⁶ and the nitrogen atom to which R⁵ and R⁶ are attached, represents a 5- or 6-membered nitrogen containing ring, optionally substituted with a =O group.

10. A compound as claimed in claim 1, wherein R⁶ represents linear, branched or cyclic $C_{1-6}$ alkyl, C(O)—$C_{1-6}$ alkyl or, together with R⁵ and the nitrogen atom to which R⁵ and R⁶ are attached, represents a 4- to 6-membered nitrogen-containing ring, optionally substituted with a =O group.

11. A compound as claimed in claim 10, wherein R⁶ represents methyl, C(O)—$C_{1-6}$ alkyl or, together with R⁵ and the nitrogen atom to which R⁵ and R⁶ are attached, represents a 5- or 6-membered nitrogen-containing ring, optionally substituted with a =O group.

12. A compound as claimed in claim 1, wherein R⁷ represents linear, branched or cyclic $C_{1-6}$ alkyl.

13. A compound as claimed in claim 1, wherein R¹ is attached to the phenyl ring at the 3-position, relative to the —CH(OH)— group to which the phenyl ring is also attached.

14. A compound as claimed in claim 1, wherein, when R² is present, it is attached to the phenyl ring at the 5-position, relative to the —CH(OH)— group to which the phenyl ring is also attached.

15. A compound as claimed in claim 1, wherein, when R⁴ represents OR$^{8a}$, then R$^{8a}$ represents linear or branched $C_{1-6}$ alkyl, $C_{4-5}$ cyclic alkyl, which latter two groups are optionally interrupted by oxygen, or phenyl or $C_{1-2}$ alkylphenyl, which latter two groups are optionally substituted as defined in claim 1, or R$^{8a}$ represents CH₂OC(O)R¹¹, in which R¹¹ represents phenyl, linear, branched or cyclic $C_{1-6}$ alkyl, which latter group is optionally substituted by a substituent selected from OH, CO₂H and phenyl, or OR¹², wherein R¹² represents phenyl or linear, branched or cyclic $C_{1-6}$ alkyl, which latter group is optionally substituted by a substituent selected from OH, CO₂H and phenyl.

16. A compound as claimed in claim 1, wherein, when R⁴ represents C(O)OR$^{8b}$, then R$^{8b}$ represents linear or branched $C_{1-2}$ alkylphenyl or phenyl, which latter two groups are optionally substituted as defined in claim 1.

17. A compound of formula I, as defined in claim 1, wherein fragment

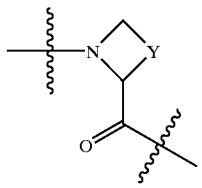

is in the S-configuration.

18. A compound of formula I, as defined in claim 1, wherein the fragment

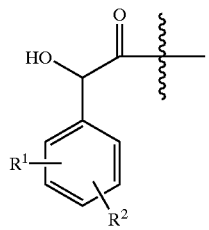

is in the R-configuration.

19. A pharmaceutical formulation comprising a compound as defined in claim 1, or a pharmaceutically acceptable salt thereof, in admixture with a pharmaceutically acceptable adjuvant, diluent or carrier.

20. A method of treatment of a condition where inhibition of thrombin is required which method comprises administration of a therapeutically effective amount of a compound as defined in claim 1, or a pharmaceutically acceptable salt thereof, to a person suffering from, or susceptible to, such a condition.

21. A method as claimed in claim 20, wherein the condition is thrombosis.

22. A method as claimed in claim 20, wherein the condition is hypercoagulability in blood and tissues.

23. A process for the preparation of a compound of formula I which comprises:

(i) the coupling of a compound of formula II,

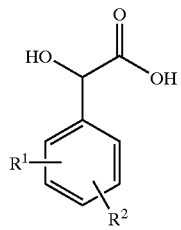

wherein $R^1$ and $R^2$ are as defined in claim 1 with a compound of formula III,

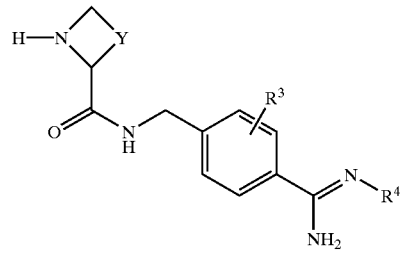

wherein Y, $R^3$ and $R^4$ are as defined in claim 1;

(ii) the coupling of a compound of formula IV,

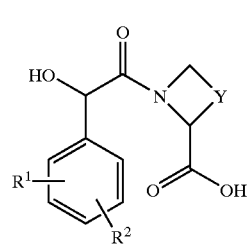

wherein $R^1$, $R^2$ and Y are as defined in claim 1 with a compound of formula V,

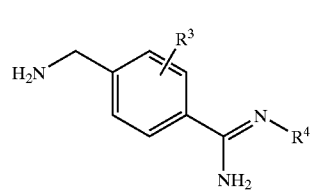

wherein $R^3$ and $R^4$ are as defined in claim 1;

(iii) for compounds of formula I in which $R^4$ represents OH or $OR^{8a}$, reaction of a compound of formula VI,

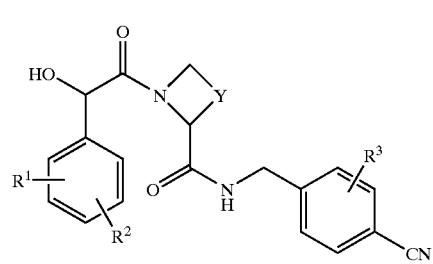

wherein $R^1$, $R^2$, Y and $R^3$ are as defined in claim 1, with a compound of formula VII, $H_2NOR^a$      VII wherein $R^a$ represents H or $R^{8a}$ and $R^{8a}$ is as defined in claim 1, optionally by pre-treating the compound of formula VI with gaseous HCl, in the presence of a lower alkyl alcohol, to form a compound of formula VIII,

VIII

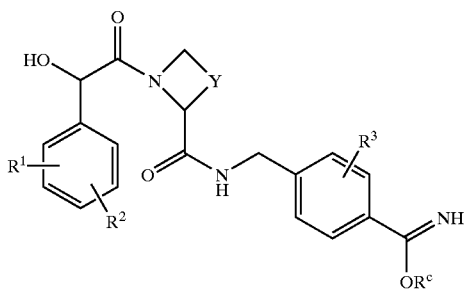

IXB

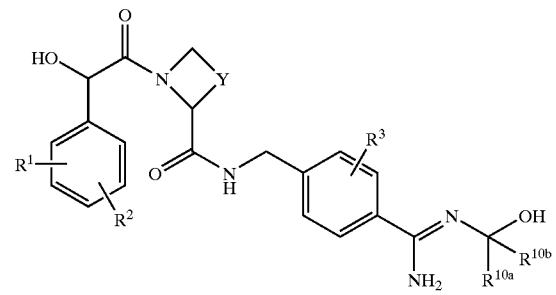

wherein $R^c$ represents lower alkyl and $R^1$, $R^2$, Y and $R^3$ are as defined in claim 1;

(iv) for compounds of formula I in which $R^4$ represent OH or $OR^{8a}$, reaction of a compound corresponding to a compound of formula I, in which, in place of $R^4$, a protecting group $C(O)OR^{b1}$ is present, in which $R^{b1}$ represents 2-trimethylsilylethyl, $C_{1-6}$ alkyl or alkylphenyl, with a compound of formula VII as defined above;

(v) for compounds of formula I in which $R^4$ represents $C(O)OR^{8b}$, reaction of a compound of formula I in which $R^4$ represents H with a compound of formula IX, $$L^1\text{—}C(O)OR^{8b} \qquad \text{IX}$$

wherein $L^1$ represents a leaving group, and $R^{8b}$ is as defined in claim 1;

(vi) for compounds of formula I in which $R^4$ represents $OR^{8a}$, reaction of a corresponding compound of formula I in which $R^4$ represents OH with a compound of formula IXA, $$L^1\text{—}R^{8a} \qquad \text{IXA}$$

wherein $R^{8a}$ is as defined in claim 1 and $L^1$ is as defined above;

(vii) for compounds of formula I in which $R^4$ represents $R^{8c}$, wherein $R^{8c}$ represents $C(R^{10a})(R^{10b})OC(O)R^{11}$ or $C(R^{10a})(R^{10b})OC(O)N(H)R^{12}$, reaction of a corresponding compound of formula IXB, wherein $R^1$, $R^2$, Y, $R^3$, $R^{10a}$ and $R^{10b}$ are as defined in claim 1, with a compound of formula IXC, $$L^1C(O)R^{13} \qquad \text{IXC}$$

wherein $R^{13}$ represents $R^{11}$ or $N(H)R^{12}$, and $R^{11}$ and $R^{12}$ are as defined in claim 1 and $L^1$ is as defined above;

(viii) for compounds of formula I in which $R^4$ represents $R^{8c}$, reaction of a corresponding compound of formula I in which $R^4$ represents H with a compound of formula IXD, $$L^1C(R^{10a})(R^{10b})R^{14} \qquad \text{IXD}$$

wherein $R^{14}$ represents $OC(O)R^{11}$, $NHC(O)OR^{12}$ or $OC(O)N(H)R^{12}$, and $R^{10a}$, $R^{10b}$, $R^{11}$ and $R^{12}$ are as defined in claim 1 and $L^1$ is as defined above;

(ix) for compounds of formula I in which $R^1$ includes a $S(O)$ or a $S(O)_2$ group, oxidation of a corresponding compound of formula I wherein $R^1$ includes a S group;

(x) deprotection of a protected derivative of a compound of formula I as defined in claim 1; or (xi) introduction or interconversion of a substituent on an aromatic, a non-aromatic, a carbocyclic or a heterocyclic ring in a compound of formula I as defined in claim 1.

* * * * *

UNITED STATES PATENT AND TRADEMARK OFFICE
CERTIFICATE OF CORRECTION

PATENT NO. : 6,599,894 B1
DATED : July 29, 2003
INVENTOR(S) : Inghardt et al.

It is certified that error appears in the above-identified patent and that said Letters Patent is hereby corrected as shown below:

<u>Title page</u>,
Item [73], Assignee, please delete "AstŕaZeneca" and insert -- AstraZeneca --;

<u>Column 1</u>,
Line 42, please delete "improvements m" and insert -- improvements in --;
Line 57, please delete "fibrinogen Aa" and insert -- fibrinogen A$\alpha$ --;

<u>Column 3</u>,
Line 66, please delete "$C_{6-8}$, alkyl" and insert -- $C_{1-8}$ alkyl --;

<u>Column 8</u>,
Line 19, please delete "$R^1$ represents" and insert -- $R^a$ represents --;

<u>Column 11</u>,
Line 54, please delete "IVA" and insert -- XIVA --;

<u>Column 13</u>,
Line 17, please delete "methanouwater" and insert -- methanol/water --;

<u>Column 20</u>,
Lines 9 and 26, please delete "sub-tide" and insert -- sub-title --;

<u>Column 23</u>,
Line 46, please delete "4.704.81" and insert -- 4.70-4.81 --;
Line 47, please delete "3.904.44" and insert -- 3.90-4.44 --;

<u>Column 27</u>,
Line 9, please delete "(100$\mu$L)" and insert -- (100 ml) --;

<u>Column 28</u>,
Line 30, please delete "tide" and insert -- title --;

<u>Column 33</u>,
Line 33, please delete "dimethy14-oxo-1,3-dioxolane" and insert
-- dimethyl-4-oxo-1,3-dioxolane --;

<u>Column 36</u>,
Line 20, please delete "dioxolane" and insert -- dioxolane --;
Line 47, please delete "sub-tide" and insert -- sub-title --;

UNITED STATES PATENT AND TRADEMARK OFFICE
CERTIFICATE OF CORRECTION

PATENT NO. : 6,599,894 B1
DATED : July 29, 2003
INVENTOR(S) : Inghardt et al.

It is certified that error appears in the above-identified patent and that said Letters Patent is hereby corrected as shown below:

Column 38,
Line 13, please delete "4.254.15" and insert -- 4.25-4. 15 --;

Column 41,
Line 22, please delete "sub-tide" and insert -- sub-title --;

Column 42,
Line 31, please delete "sub-tide" and insert -- sub-title --;

Column 44,
Line 67, please delete "Celite" and insert -- Celite® --;

Column 45,
Line 46, please delete "Celite" and insert -- Celite® --;

Column 49,
Line 10, please delete "represents 3- to" and insert -- represents a 3- to --;
Line 35, please delete "$C(R^{10a})(R^{10b})OC(O)R^{12}$" and insert
-- $C(R^{10a})(R^{10b})OC(O)N(H)R^{12}$ --;

Column 53,
Line 17, please delete "represent" and insert -- represents --.

Signed and Sealed this

Twenty-second Day of June, 2004

JON W. DUDAS
*Acting Director of the United States Patent and Trademark Office*